(12) United States Patent
Sætrom

(10) Patent No.: US 9,885,046 B2
(45) Date of Patent: Feb. 6, 2018

(54) METHODS OF INDUCING INSULIN PRODUCTION

(71) Applicant: MINA THERAPEUTICS LIMITED, London (GB)

(72) Inventor: Pål Sætrom, Trondheim (NO)

(73) Assignee: MiNA THERAPEUTICS LIMITED, London (GB)

(*) Notice: Subject to any disclaimer, the term of this patent is extended or adjusted under 35 U.S.C. 154(b) by 15 days.

(21) Appl. No.: 14/547,317

(22) Filed: Nov. 19, 2014

(65) Prior Publication Data

US 2015/0176008 A1 Jun. 25, 2015

Related U.S. Application Data

(63) Continuation of application No. 13/877,968, filed as application No. PCT/GB2011/051942 on Oct. 10, 2011, now Pat. No. 8,916,534.

(30) Foreign Application Priority Data

Oct. 8, 2010 (GB) .................................. 1016989.4
Mar. 7, 2011 (GB) .................................. 1103745.4

(51) Int. Cl.
| A61K 31/70 | (2006.01) |
| C07H 21/02 | (2006.01) |
| C07H 21/04 | (2006.01) |
| C12N 15/113 | (2010.01) |
| C12N 15/11 | (2006.01) |
| C12N 5/00 | (2006.01) |

(52) U.S. Cl.
CPC .......... *C12N 15/1136* (2013.01); *C12N 15/11* (2013.01); *C12N 15/113* (2013.01); *C12N 15/1135* (2013.01); *C12N 15/1138* (2013.01); *C12N 2310/11* (2013.01); *C12N 2310/113* (2013.01); *C12N 2310/14* (2013.01); *C12N 2310/3519* (2013.01)

(58) Field of Classification Search
None
See application file for complete search history.

(56) References Cited

U.S. PATENT DOCUMENTS

| 8,193,330 B2 | 6/2012 | German |
| 8,785,184 B2 | 7/2014 | Xu |
| 2009/0269763 A1 | 10/2009 | Eilertsen et al. |
| 2012/0322853 A1* | 12/2012 | Collard .............. A61K 31/7088 514/44 A |

FOREIGN PATENT DOCUMENTS

| EP | 2363467 | 9/2011 |
| WO | 2006113246 | 10/2006 |
| WO | 2007086990 | 8/2007 |
| WO | 2007087113 | 8/2007 |
| WO | 2008109449 | 9/2008 |
| WO | 2008109556 | 9/2008 |
| WO | 2008150814 | 12/2008 |
| WO | 2009046397 | 4/2009 |
| WO | 2009086428 | 7/2009 |
| WO | 2009126250 | 10/2009 |
| WO | 2009126927 | 10/2009 |
| WO | 2010047216 | 4/2010 |
| WO | 2010057045 | 5/2010 |
| WO | 2010108126 | 9/2010 |
| WO | 2010135329 | 11/2010 |
| WO | 2011085066 | 7/2011 |
| WO | 2011161460 | 12/2011 |

OTHER PUBLICATIONS

Morris, K. et al., Bidirectional transcription directs both transcriptional gene activation and suppression in human cells, PLOS Genetics, 2008, vol. 4, No. 11, p. E1000258.
Long-Cheng, L et al. Small dsRNAs induce transcriptional activation in human cells, Proceedings of the National Academy of Sciences USA, 2006, vol. 103, No. 46, pp. 17337-17342.
Place, R et al., MicroRNA-373 induces expression of genes with complementary promoter sequences, Proceedings of the National Academy of Sciences USA, 2008, vol. 105, No. 5, pp. 1608-1613.
Xu, N. et al., MicroRNA-145 regulates OCT4, SOX2, and KLF4 and represses pluripotency in human embryonic stem cells, Cell, 2009, vol. 137, No. 4, pp. 647-658.
Janowski, B. et al., Activating gene expression in mammalian cells with promoter-targeted duplex RNAs, Nature Chemical Biology, 2007, vol. 3 No. 3, pp. 166-173.
Elmen, J. et al., Antagonism of microRNA-122 in mice by systemically administered LNA-antimiR leads to up-regulation of a large set of predicted taret mRNAs in the liver, Nucleic Acid Research, 2007, vol. 36, No. 4, pp. 1153-1162.
Tian, Y. et al., MicroRNA-10b promotes migration and invasion through KLF4 in human esophageal cancer cell lines, Journal of Biological Chemistry, 2010, vol. 285, No. 11, pp. 7986-7994.

(Continued)

*Primary Examiner* — Sean McGarry
(74) *Attorney, Agent, or Firm* — DT Ward, PC; Donna T. Ward; Heng Zhu

(57) ABSTRACT

The present invention provides a method of inducing insulin production in a cell by up-regulating a target gene involved in insulin production in said cell using an saRNA (short activating ribonucleic acid) which specifically down-regulates a target antisense RNA transcript present in said cell, wherein
(i) said target RNA transcript is complementary to a sequence located on the coding strand of the target gene between 1000 nucleotides upstream and 1000 nucleotides downstream of the transcription start site of the target gene; and
(ii) said sRNA is a single or double stranded RNA molecule up to 30 nucleotides in length comprising a sequence of at least 13 nucleotides which has at least 95% complementarity to a region of the target transcript. Also provided are certain saRNA molecules and uses thereof, particular medical uses, and induced cells and uses thereof.

12 Claims, 15 Drawing Sheets

(56) References Cited

OTHER PUBLICATIONS

Figure 1:
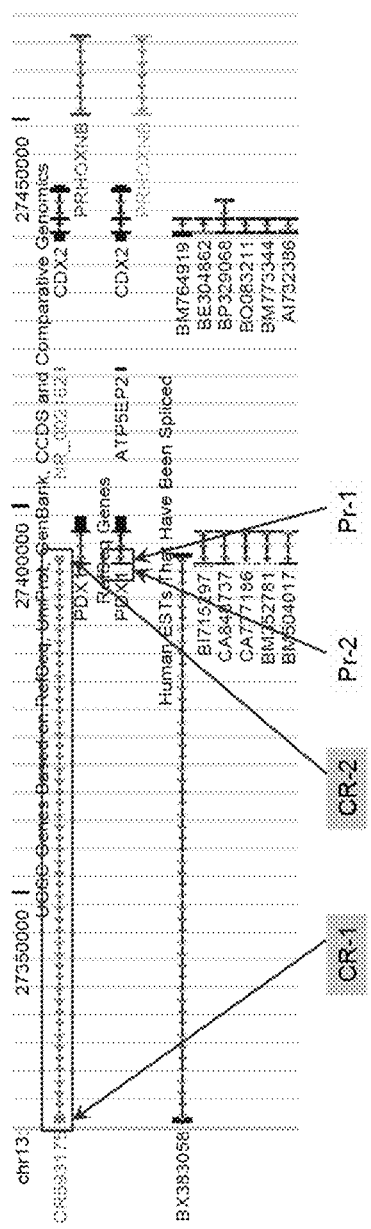

Napoli, S. et al., Promoter-specific transcriptional interference and c-myc gene silencing by siRNAs in human cells, The EMBO Journal, 2009, vol. 28, No. 12, pp. 1708-1719.
International Search Report for PCT/GB2011/051185, dated Dec. 19, 2011.
Search Report dated May 16, 2011, from the UK Patent Office in Application No. GB1010557.5.
Li, Y. et al., miR-375 enchances palmitate-induced lipoapoptosis in insulin-secreting NIT-1 cells by repressing myotrophin (V1) protein expression, International Journal of Clinical and Experimental Pathology, 2010, vol. 3, No. 3, pp. 254-264.
Tang, X. et al., Role of microRNAs in diabetes, Biochimica et Biophysica Acta, 2008, vol. 1779, No. 1, pp. 697-701.
Schwartz, J. et al., Antisense transcripts are targets for activating small RNAs, Nature Structural & Molecular Biology, 2008, vol. 15, No. 8, pp. 842,848.
Place, R. et al., Defining features and exploring chemical modifications to manipulate RNAa activity, Current Pharmaceutical Biotechnology, 2010, vol. 11, No. 5, pp. 518-526.
Wahlestedt, C., Natural antisense and noncoding RNA transcripts as potential drug targets, Drug Discovery Today, 2006, vol. 11, No. 11/12, pp. 503-508.
International Search Report for PCT/GB2011/051942, dated Feb. 15, 2012.
International Search Report for PCT/GB2011/051940, dated Jul. 18, 2012.

* cited by examiner

METHODS OF INDUCING INSULIN PRODUCTION

CROSS-REFERENCE TO RELATED APPLICATIONS

This application is a continuation of U.S. patent application Ser. No. 13/877,968 filed on Jul. 18, 2013, which is a national stage entry of PCT Application No. PCT/GB11/51942 filed Oct. 10, 2011, which claims benefit of G.B. Provisional Application No. GB 1016989.4 filed Oct. 8, 2010 and G.B. Provisional Application No. GB 1103745.4 filed Mar. 7, 2011. The entire contents of these applications are hereby incorporated by reference.

REFERENCE TO SEQUENCE LISTING

The present application is being filed along with a Sequence Listing in electronic format. The sequence listing filed, entitled 20581006USCONSEQLST, was created on Nov. 17, 2014 and is 20,823 bytes in size. The information in electronic format of the Sequence Listing is incorporated herein by reference in its entirety.

FIELD OF THE INVENTION

The present invention relates to inducing insulin production in a cell by up-regulating a target gene involved in insulin production in said cell using an saRNA (short activating ribonucleic acid).

BACKGROUND OF THE INVENTION

The present invention relates to methods of generating specialised cells, particularly cells capable of producing insulin. The methods involve the use of short RNA molecules capable of modulating, particularly increasing, the expression of target genes involved in insulin production. The invention also relates to the design and synthesis of such short RNA molecules and their use in therapy.

Diabetes mellitus affects at least 200 million people worldwide. Diabetes arises when the body is incapable of producing sufficient quantities of insulin, the hormone that regulates the levels of glucose in the blood. In healthy individuals, insulin is produced by the pancreas, more particularly by pancreatic beta-cells. Type I diabetes is typically caused by the destruction of the β-cells of the pancreas by T-cells of the immune system, so an autoimmune disorder is often the underlying cause, although infections, especially viral infections, or injury can also cause the destruction or malfunction of pancreatic beta-cells. This results in a severe deficiency of insulin production.

Current treatment options mainly rely on the administration of exogenous insulin. The drawbacks include inconvenience for the patient, and this approach is difficult to fine-tune, typically resulting in excess insulin at some instances and too little insulin at other times.

The world wide prevalence of type I diabetes is increasing and concomitantly the clinical challenge to maintain a constant source of active insulin secretion in these patients has pushed considerable efforts into finding alternative mechanisms to achieve this. However, current attempts to regenerate islet cells or transplant islets cells are not entirely effective, so there remains a need for the generation of insulin-producing cells.

Diabetes is by far not the only disease that is caused by a lack of specialized cells carrying out important physiological functions. Many other diseases are characterised by the absence or malfunction of specialised cells, and there is a need to generate such specialised cells for the treatment of these disorders. Further diseases that can benefit from increased insulin production include type II diabetes, fatty liver, obesity, especially morbid obesity and any other disorders associated with defects of glucose and/or insulin production, uptake and/or utilisation.

The pancreas is composed of two compartments, the exocrine and the endocrine, each with distinct functions. The endocrine compartment consists of islets of Langerhans which are composed of clusters of four cell types that synthesise the peptide hormones insulin (β-cells), glucagon (α-cells), somatostatin (δ-cells) and pancreatic polypeptide (γ-cells). These cells have been shown to differentiate from ductal epithelial stem cells through sequential differentiation during embryogenesis (10-12). The pancreas originates from distinct embryonic outgrowths of the dorsal and ventral regions of the foregut endoderm where these outgrowths give rise to both endocrine and exocrine cells (13). The expression of the earliest known pancreatic markers include Hlxb9 and PDX1 homeobox protein (14-16). These transcription factors respond to the primary signals for pancreatic specification and denote the pancreatic stem cell, prior to morphogenesis. PDX1 is necessary for the morphogenesis and differentiation of the pancreatic epithelium. Glucagon and insulin expression are initiated at the downstream bud stage (16, 17). PDX1 furthermore gives rise to neurogenin 3 (Ngn3) positive cells as progenitors of the endocrine lineage (18, 19). Subsequently activation of Ngn3 initiates the expression of additional transcriptional factors including NeuroD1, Rfx6 and MafA which then directs the differentiation of cells into mature islet cells (20, 21). Betacellulin overexpression has been shown to induce insulin secretion.

Proinsulin is synthesized in the endoplasmic reticulum, where it is folded and its disulfide bonds are oxidized. It is then transported to the Golgi apparatus where it is packaged into secretory vesicles, and where it is processed by a series of proteases to form mature insulin. Mature insulin has 35 fewer amino acids; 4 are removed altogether, and the remaining 31 form the C-peptide. The C-peptide is abstracted from the centre of the proinsulin sequence; the two other ends (the B chain and A chain) remain connected by disulfide bonds. Thus, proinsulin and insulin are encoded by the same gene, so any reference herein to the "insulin" gene should be understood to mean the gene encoding proinsulin, and any reference to the "proinsulin" gene should be understood to mean the gene which codes for a protein that ultimately becomes insulin.

The present inventor has set out to develop a way of up-regulating a target gene to yield cells which have a desired specialisation, preferably which are capable of producing insulin, most preferably in a glucose-responsive manner.

By "specialised" cell is meant a cell which performs or is capable of performing a specific function, preferably a tissue-specific function. Specialisation is characterised by the expression of one or more specific proteins, which may inter alia be a marker protein, or a secreted protein such as insulin. Any reference herein to "specialisation" or a "specialised cell" is preferably insulin production or a cell capable of producing insulin.

Current methods of up-regulating the expression of a gene of interest require the introduction of extra copies of the gene into a cell, either by using viruses to introduce extra copies of the gene into the host genome or by introducing plasmids that express extra copies of the target gene. Thus, for up-regulation invasive transient transfection or stable viral transduction of expression vectors into cells is currently required, which raises safety concerns. The current methods typically involve the non-transient application of up-regulatory agents. A limitation of these methods is that the effects are similarly non-transient.

RNA interference (RNAi) is an important gene regulatory mechanism that causes sequence-specific down-regulation of target mRNAs. RNAi is mediated by "interfering RNA" (iRNA); an umbrella term which encompasses a variety of short double stranded RNA (dsRNA) molecules which function in the RNAi process.

Exogenous dsRNA can be processed by the ribonuclease protein Dicer into double-stranded fragments of 19 to 25 base pairs, preferably 21-23 base pairs, with several unpaired bases on each 3' end forming a 3' overhang. Preferably, each 3' overhang is 1-3, more preferably 2, nucleotides long. These short double-stranded fragments are termed small interfering RNAs (siRNAs) and these molecules effect the down-regulation of the expression of target genes.

Since the elucidation of their function, siRNAs have been used as tools to down-regulate specific genes. They can give transient suppression or, when stably integrated as short hairpins RNAs (shRNAs), stable suppression. siRNAs and shRNAs have been used widely in "knockdown" or "loss of function" experiments, in which the function of a gene of interest is studied by observing the effects of the decrease in expression of the gene. RNAi is considered to have potential benefits as a technique for genomic mapping and annotation. Attempts have also been made to exploit RNA interference in therapy.

A protein complex called the RNA-induced silencing complex (RISC) incorporates one of the siRNA strands and uses this strand as a guide to recognize target mRNAs. Depending on the complementarity between guide RNA and mRNA, RISC then destroys or inhibits translation of the mRNA. Perfect complementarity results in mRNA cleavage and destruction and as result of the cleavage the mRNA can no longer be translated into protein. Partial complementarity—particularly with sites in the mRNA's 3' untranslated region (UTR)—results in translational inhibition. RNAi is conserved in most eukaryotes and can, by introducing exogenous siRNAs, be used as a tool to down-regulate specific genes.

Recently it has been discovered that although RISC primarily regulates genes post transcription, RNAi can also modulate gene transcription itself. In fission yeast, small RNAs regulate chromatin through homologues of the RISC complex. The RNA-loaded RISC complexes apparently bind non-coding RNAs (ncRNA) and thereby recruit histone-modifying proteins to the ncRNAs' loci. Plants, flies, nematodes, ciliates, and fungi also have similar mechanisms. In mammals, much of the exact mechanism remains unclear, but it is believed that short RNAs regulate transcription by targeting for destruction transcripts that are sense or antisense to the regulated RNA and which are presumed to be non-coding transcripts. Destruction of these non-coding transcripts through RNA targeting has different effects on epigenetic regulatory patterns depending on the nature of the RNA target. Destruction of ncRNA targets which are sense to a given mRNA results in transcriptional repression of that mRNA, whereas destruction of ncRNA targets which are antisense to a given mRNA results in transcriptional activation of that mRNA. By targeting such antisense transcripts, RNAi can therefore be used to up-regulate specific genes.

DETAILED DESCRIPTION

The present inventor has developed new short RNA molecules which achieve up-regulation of target genes and preferably yield specialised cells, and which overcome many of the problems associated with the methods of the prior art. In particular, the molecules of the present invention do not raise the safety concerns associated with the administration of genetic elements that may integrate into the genome of the host cell.

The inventor has used an advantageous method/algorithm for the identification of suitable RNA target transcripts and for the design of these short RNA molecules. The inventor has therefore provided novel short RNA molecules which target RNA transcripts in the host cell in order to modulate target genes and in particular target genes which are specialization-inducing genes. The short RNAs of the invention are smaller molecules than the expression vectors of the prior art and so are therefore less invasive. The fact that the molecules of this invention use the host's own regulatory systems to modulate genes may be less invasive than introducing into the host extra copies of the genes.

The present inventor has developed short RNAs which can induce insulin production by up-regulating a target gene involved in insulin production. It is believed that this up-regulation is via down-regulation of an antisense RNA transcript.

The short RNAs of the present invention can up-regulate mRNA and protein levels of the target genes, which can lead to the up-regulation of downstream targets. The short RNAs of the invention are also referred to herein as "specialisation-inducing" RNAs. The specialisation-inducing RNAs of the present invention (such as PDX1-activating, Neurogenin-3-activating Rfx6-activating and MafA-activating RNAs) are an effective, and safe alternative for generating specialised (insulin producing) cells to be used in regenerative medicine.

A major advantage of the present invention is that it concerns the transient application of gene-activating small RNAs, whose effects are also transient. This permits the generation of induced cells (i.e. cells which have been induced to specialise using the methods disclosed herein) which are able to react to stimuli, for example to produce insulin in response to glucose.

Put in the most general terms, in one aspect the present invention provides a method of inducing a cell into a specialised cell by up-regulating a target gene in said cell, wherein said target gene is a specialisation-inducing gene and wherein said method comprises contacting said cell with a short RNA molecule which specifically down-regulates a target RNA transcript present in said cell, wherein said target RNA transcript:
  i) is transcribed from
    a) either strand of a locus up to 100 kb upstream of the target gene's transcription start site,
    b) either strand of a locus up to 100 kb downstream of the target gene's transcription stop site; or
    c) either strand of a locus which interacts physically with the target gene; and
  ii) comprises a sequence which is antisense to a genomic sequence located between 100 kb upstream of the target gene's transcription start site and 100 kb downstream of the target gene's transcription stop site.

By "inducing a cell into a specialised cell" is meant that a specialised cell is generated.

Alternatively viewed, the present invention provides a method of inducing cell specialisation by up-regulating a target gene in a starting cell, wherein said target gene is a specialisation-inducing gene and wherein said method comprises contacting said starting cell with a short RNA molecule which specifically down-regulates a target RNA transcript present in said cell, wherein said target RNA transcript:

i) is transcribed from
  a) either strand of a locus up to 100 kb upstream of the target gene's transcription start site,
  b) either strand of a locus up to 100 kb downstream of the target gene's transcription stop site; or
  c) either strand of a locus which interacts physically with the target gene; and
ii) comprises a sequence which is antisense to a genomic sequence located between 100 kb upstream of the target gene's transcription start site and 100 kb downstream of the target gene's transcription stop site.

Alternatively viewed, the present invention provides a method of inducing or increasing the production of a target protein by cell or a population of cells through up-regulating a target gene in said cell(s), wherein said target gene is a specialisation-inducing gene and wherein said method comprises contacting said cell(s) with a short RNA molecule which specifically down-regulates a target RNA transcript in said cell(s), wherein said target RNA transcript:

i) is transcribed from
  a) either strand of a locus up to 100 kb upstream of the target gene's transcription start site,
  b) either strand of a locus up to 100 kb downstream of the target gene's transcription stop site; or
  c) either strand of a locus which interacts physically with the target gene; and
ii) comprises a sequence which is antisense to a genomic sequence located between 100 kb upstream of the target gene's transcription start site and 100 kb downstream of the target gene's transcription stop site.

Viewed another way, the present invention provides a method of maintaining or increasing the expression of a specialisation-inducing target gene by a cell or population of cells through up-regulating said target gene in said cell(s), wherein said method comprises contacting said cell(s) with a short RNA molecule which specifically down-regulates a target RNA transcript in said cell(s), wherein said target RNA transcript:

i) is transcribed from
  a) either strand of a locus up to 100 kb upstream of the target gene's transcription start site,
  b) either strand of a locus up to 100 kb downstream of the target gene's transcription stop site; or
  c) either strand of a locus which interacts physically with the target gene; and
ii) comprises a sequence which is antisense to a genomic sequence located between 100 kb upstream of the target gene's transcription start site and 100 kb downstream of the target gene's transcription stop site.

More particularly, the present invention provides in one aspect a method of inducing insulin production in a cell by up-regulating a target gene involved in insulin production in said cell using a short RNA which specifically down-regulates a target antisense RNA transcript present in said cell, wherein said target RNA transcript is complementary to a sequence located on the coding strand of the target gene between 2000, 1000, 900, 800, 700, 600, 500, 400, 300, 200 or 100 nucleotides upstream and 2000, 1000, 900, 800, 700, 600, 500, 400, 300, 200 or 100 nucleotides downstream of the transcription start site of the target gene.

Preferably, there is provided a method of inducing insulin production in a cell by up-regulating a target gene involved in insulin production in said cell using an saRNA (short activating ribonucleic acid) which specifically down-regulates a target antisense RNA transcript present in said cell, wherein (i) said target RNA transcript is complementary to a sequence located on the coding strand of the target gene between 1000 nucleotides upstream and 1000 nucleotides downstream of the transcription start site of the target gene; and (ii) said sRNA is a single or double stranded RNA molecule up to 30 nucleotides in length comprising a sequence of at least 13 nucleotides which has at least 95% complementarity to a region of the target transcript.

The present inventor has not only achieved insulin expression by the induced cells. As shown in the Examples, the methods of the invention may also lead to the secretion of insulin, which is desirable for many applications. If the cells are intended for the in vitro production of insulin, then secretion of insulin avoids time-consuming insulin extraction procedures. If the cells are intended for transplantation, or if the methods are used in vivo, it is vital that the induced cells can secrete insulin.

The methods of the invention can also achieve insulin production in a glucose-responsive manner. As shown in the examples, the induced cells produce significantly more insulin in the presence of glucose than in the absence of glucose. This is clearly highly advantageous for in vivo applications.

To the best of our knowledge, this is the first report of a method of inducing cells to produce and secrete insulin in a glucose-responsive manner.

The methods/uses of the invention preferably yield cells which produce/are capable of producing insulin in a glucose-responsive manner. The expression "glucose-responsive" is well known in the art, so the skilled person is aware that "glucose-responsive" means that insulin production and/or secretion is greater in the presence of glucose than in the absence of glucose. It is to be understood that at least in an in vivo context, the "presence of glucose" means a physiologically significant concentration of glucose and the "absence of glucose" means concentrations of glucose that are too low to be physiologically significant, as well as the complete absence of glucose. Preferably, a glucose-responsive cell produces at least 20, 30, 40, 50, 60, 70, 80, 90, 95 or 100% more insulin in the presence of glucose than in the absence of glucose. Preferably, insulin production correlates positively with glucose concentration, i.e. when exposed to a high glucose concentration, the cell produces more insulin than when exposed to a low glucose concentration. Preferably, increasing glucose concentrations in the extracellular environment result in a concomitant increase in insulin production. Preferably, the cells show a glucose-responsiveness which mimics that of healthy pancreatic beta cells.

Thus, preferably, the cell is induced to produce insulin in a glucose-responsive manner. Also preferably, the cell is induced to secrete insulin.

Insulin production may be assayed using standard protocols such as immunofluorescence, ELISA or Western blotting. Appropriate assays are described in the Examples. For example, the sample may be contacted with an anti-insulin antibody, and bound antibody may be detected using a labelled secondary antibody. Insulin production may also be assayed at the RNA level, for example using (reverse transcriptase) PCR, preferably semi-quantitative or quantitative PCR. The skilled person is aware that ELISA may be used to assay insulin secretion. Glucose-responsiveness may be determined by comparing insulin production of cells exposed to glucose to cells not exposed to glucose.

As mentioned above, a specialised cell is a cell which performs or is capable of performing a specific function, preferably a tissue-specific function. By "tissue specific function" is meant a function that is characteristic of a particular tissue. For example, insulin production is pancreas-specific and dopamine production is nervous tissue-specific. Another example of a tissue-specific function is be the ability of heart cells to beat. Preferably, the specialised cell is capable of insulin production; in this embodiment it may be referred to as an insulin-producing cell.

Thus, the specific function is one which is typically carried out by a differentiated cell. In one embodiment, the specialised cell is a differentiated cell, but in another embodiment the specialised cell is multipotent or pluripotent.

"Inducing specialisation" means that the cell is induced to become specialised. This may involve differentiation, i.e. pushing the cell towards a particular lineage and reducing the cell's potency. Thus, a multipotent or pluripotent cell may be induced to differentiate into a specialised cell of a particular lineage, such as a beta cell. Inducing specialisation may involve transdifferentiation, i.e. a cell of a particular lineage may be induced to adopt a specific function characteristic of a different lineage. For example, a differentiated cell, e.g. an epithelial cell, may be induced to produce a target protein characteristic of another cell type, e.g. insulin. Alternatively, inducing specialisation may induce the cell to adopt a specialised characteristic whilst retaining a pluripotent or multipotent phenotype. Thus, inducing a stem cell to specialise may result in the generation of a pancreatic beta cell which can produce insulin, but alternatively it may result in a pluripotent cell capable of producing insulin, or a somatic non-pancreatic cell capable of producing insulin.

The specialised cell produced by the methods disclosed herein has been generated by inducing specialisation, so it may be referred to as an "induced" cell.

A specialisation-inducing gene is a gene which when up-regulated induces a cell to become specialised in one of more respects. As explained below, the effect of the specialisation-inducing gene may be direct or indirect, and if indirect it may be downstream.

In the method of the invention, up-regulation of the target gene may affect the production of the target protein directly or indirectly. The target gene may encode the target protein (direct effect), or it may encode a factor which immediately or ultimately regulates the production of the target protein (indirect effect). Regulation of production may inter alia involve activation of transcription of the gene encoding the target protein, or inhibition of a repressor of transcription of the gene encoding the target protein. The target gene may also affect production of the target protein by modulating a cascade of events, which may be referred to as "downstream" regulation. Downstream regulation may involve up-regulation of the target gene which modulates a second gene which may regulate the target protein, or the second gene may modulate a third gene and this cascade eventually leads to the upregulation of the target protein production.

A "target gene" or "gene of interest" is a gene whose expression is desired to be modulated, preferably increased, although the target gene is preferably different from the gene encoding the final target protein of interest. The target gene is preferably a gene involved in insulin production, and the target protein is preferably insulin. Thus, any reference to a "target gene" should be understood to mean preferably a gene involved in insulin production and any reference to a "target protein" should be understood to mean preferably insulin. The target gene is sometimes referred to herein as a "specialisation-inducing" gene. Any reference herein to a "specialisation gene" or a "specialisation-inducing gene" is preferably a reference to a gene involved in insulin production.

The target gene is preferably a gene involved in insulin production. In the human body, insulin producing cells must be able to generate and secrete the active form of insulin. By "insulin production" is therefore meant not only the synthesis of insulin, but also the processing of insulin into its active form, as well as the secretion of insulin. A "gene involved in insulin production" may be any gene that affects insulin production. The effect may be indirect or direct as explained above. Thus, the gene may be a transcription factor, which may directly or indirectly regulate the transcription of the insulin gene. Insulin production is affected by glucose levels—glucose uptake/metabolism is particularly important for insulin secretion to take place—, so the gene involved in insulin production may be a gene involved in the recognition, transport or metabolism of glucose, such as a glucose transporter or glucokinase. The gene may be a gene involved in the secretion of insulin, including genes involved in the transport of insulin.

The term target gene includes any nucleotide sequence, which may or may not contain identified gene(s), including, but not limited to, coding region(s), non-coding region(s), untranscribed region(s), intron(s), exon(s) and transgenes(s). Preferably, the target gene is an identified gene. The target gene can be a gene derived from a cell, an endogenous gene, a transgene or exogenous genes such as genes of a pathogen, which is present in the cell after infection thereof. The cell containing the target gene can be derived from or contained in any organism but is preferably human. A "target mRNA" sequence is an mRNA sequence derived from a target gene.

For example, if the target protein is insulin, the target gene may for example be the gene encoding (pro)insulin (direct effect), or it may be a gene which affects insulin production (indirect effect), for example selected from PDX1, Neurogenin 3 (Ngn3), Rfx6, MafA, GLP1 receptor, FOXA2, HNF1A, Hlxb9, Hnf6, Ptf1a, Neuro D, betacellulin, ABCC8, glucokinase (GCK), GLUT2 and/or Nkx6-1, more preferably PDX1, Ngn3, Rfx6, and/or MafA. MafA is especially preferred.

PDX1 is the transcription factor Pancreatic and Duodenal homeoboX 1. It is important for downstream activation of various genes involved in regulating insulin expression. These factors include somatostatin, glucokinase and GLUT2. GLUT2 is a glucose transporter. NGN3 is the basic helix-loop-helix transcription factor Neurogenin 3 which together with NEUROD (Neurogenic differentiation factor) regulates expression of insulin. Nkx6-1 is the NK6 homeobox 1 transcription factor required for development of β-cells. GCK is a hexokinase enzyme which phoshoporylates glucose in the initial steps of glucose metabolism. GCK activity serves as a principal control for the secretion of insulin. ABCC8 (ATP-binding cassette—sub-family C, member 8) is a member of the superfamily of ATP binding cassette transporters. ABCC8 functions in ATP sensitive potassium channels for insulin release. GLP1 is the Glucagon-Like Peptide 1 which regulates insulin secretion. MAFA (v-maf musculoaponeurotic fibrosarcoma oncogene homologue A) is a β-cell specific transcription factor that binds to RIPE3b—a conserved enhancer element that regulates expression of the insulin gene (INS) during maturation of β-cells. FOXA2 is a forkhead transcription factor which regulates insulin secretion. Hepatic Nuclear Factor 1 Alpha (HNF1A) is a transcription factor.

Two or more different short RNA molecules may be used together in the methods of the present invention. They may down-regulate the same target RNA transcript or each short RNA molecule may down-regulate different RNA transcripts. In embodiments where two or more different short RNA molecules down-regulate different RNA transcripts, they may up-regulate the same or different target genes.

In some embodiments, two or more target genes involved in insulin production, including secretion, are up-regulated using the methods of the invention. Preferably, one of these target genes is MafA. The other target gene(s) may preferably be selected from PDX1, Neurogenin 3 (Ngn3), Rfx6, GLP1 receptor, FOXA2, HNF1A, Hlxb9, Hnf6, Ptf1a, Neuro D, betacellulin, insulin, ABCC8, glucokinase (GCK), GLUT2 and/or Nkx6-1.

In some embodiments, one or more target genes involved in glucose or glucose metabolism are up-regulated using the methods of the invention. These target genes may preferably be selected from Glut1, Glut2 and glucokinase.

In some embodiments, one or more target genes involved directly or indirectly in insulin secretion are up-regulated using the methods of the invention. These target genes may preferably be selected from transport proteins such as sodium/potassium pump ($Na^+/K^+$-ATPase), e.g. ABCC8.

In some embodiments, one or more target genes involved in transcription, cell survival and/or proliferation are up-regulated using the methods of the invention. These target genes may preferably be selected from v-myc, bcl2, telomerase and NFkB.

v-myc myelocytomatosis viral oncogene homolog (v-myc) is a transcription factor which plays a role in cell cycle progression, apoptosis and cellular transformation. B-cell CLL/lymphoma 2 (bcl2) is a membrane protein which regulates cell death by controlling the mitochondrial membrane permeability.

In some embodiments, one or more target genes involved in the post-transplantational integration of cells, such as cell signalling and/or adhesion are up-regulated using the methods of the invention. These target genes may preferably be selected from the integrin family.

Any combinations of the target genes discussed above are contemplated.

Preferred sequences of suitable short RNA molecules which may be used to up-regulate many of these target genes are provided in the Tables.

The methods of the invention may be carried out using a totipotent, pluripotent multipotent or somatic cell, i.e. any of these cells may be used as a starting cell which is induced to specialise. The methods disclosed herein generate a specialised cell from a starting cell. The specialised cell generated via these methods differ from the starting cell at least in one characteristic. Preferably, the specialised cell expresses a target protein which the starting cell does not express. As mentioned above, the target protein is preferably insulin and the specialised cell is preferably a cell producing/capable of producing insulin.

Suitable starting cells are discussed in more detail below. A totipotent cell has the ability to differentiate into every type of cell found in an organism, and of forming the entire organism. A pluripotent cell is a cell that has the potential to differentiate into any of the three germ layers: endoderm (interior stomach lining, gastrointestinal tract, the lungs), mesoderm (muscle, bone, blood, urogenital), or ectoderm (epidermal tissues and nervous system). Differentiation potential is the extent to which a cell may differentiate into a cell of different types. A pluripotent cell has a greater differentiation potential than a multipotent cell. Within a population of cells, individual cells may possess different differentiation potentials. A population of multipotent cells may, after time, comprise some cells which have differentiated into somatic cells and some cells which have not differentiated and are still multipotent. Similarly, a population of pluripotent cells, after time, may contain multipotent cells and somatic cells as well as pluripotent cells. Thus, the methods of the invention may be used in connection with a population of totipotent, pluripotent, multipotent or somatic cells. The cells may be adult or embryonic, e.g. adult stem cells, embryonic stem cells or carcinoma-derived stem cells, adult stem cells being preferred.

The cells are preferably animal cells, more preferably mammalian, e.g. from a mouse, rat, monkey, dog, cow, sheep, most preferably human, although optionally the cell is non-human.

The pluripotent cell may be an induced pluripotent stem cell (abbreviated as iPSC or iPS cell), i.e. a type of pluripotent stem cell artificially derived from a non-pluripotent cell, typically an adult somatic cell, by inducing a "forced" expression of certain genes.

WO2005/059113 discloses a particularly advantageous type of pluripotent stem cell. This stem cell can be directly isolated from bone marrow and/or blood, e.g. peripheral blood, or from material taken from the umbilical cord or placenta, and has the unique ability to differentiate into ectodermal, mesodermal and endodermal cells. These cells are thus clearly multipotent or pluripotent, if not totipotent. Therefore, the stem cells described in WO2005/059113 provide a useful source of cells for tissue transplantation that may be used in an autologous (self-to-self) manner.

The cells disclosed in WO2005/059113 are known in the art as "OmniCytes". The teachings of WO2005/059113 are incorporated herein in their entirety by reference. OmniCytes are stem cells which are CD34+, capable of self regeneration and capable of differentiation into ectodermal, mesodermal and endodermal cells, including haemopoietic cells. As mentioned above, they can be directly isolated from bone marrow and/or blood. They are further characterised by their ability to adhere to plastic (e.g. the plastic of standard tissue culture vessels) during culturing. Suitable vessels are those manufactured by Corning Incorporated, New York, USA.

OmniCytes may be further characterised by the fact that they do not require feeder layers, i.e. cells (typically inactivated by gamma irradiation which supply important metabolites without further growth or division of their own) which support the growth of the stem cells.

OmniCytes can be further characterised as obtainable by:
a) enrichment of a tissue or blood sample for $CD34^+$ cells;
b) contacting the sample with a solid support and harvesting the cells which adhere to said solid support.

Suitable tissue or blood samples include, bone marrow, peripheral blood, umbilical cord blood or tissue, placenta and samples obtained from liposuction.

More particularly, they are obtainable by:
subjecting a tissue or blood sample (preferably haemopoietic tissue such as blood or a bone marrow sample) to density gradient separation;
exposing low density cells to an affinity ligand for CD34 (preferably attached to paramagnetic beads);

recovering cells attached to said CD34 ligand;
exposing the CD34+ subpopulation to tissue culture grade plastic; and
recovering CD34+ cells adherent to the plastic.

Omnicytes are preferably adult, so non-foetal.

A sample of OmniCytes was deposited with ECACC at Porton Down, Salisbury, SP4 0JG on 24 Sep. 2004 under accession number 04092401. The deposit was made by Professor Myrtle Gordon of Willow Tree Cottage, Spinning Wheel Lane, Binfield, Berkshire RG42 5QH, Great Britain and the cell line was given the name "Stem Cell OmniCyte".

The methods of the present invention are preferably carried out on a cell selected from OmniCytes, haematopoietic stem cells (HSC) and mesenchymal stem cells (MSC), OmniCytes being especially preferred.

A multipotent cell is a cell which has the potential to give rise to cells from multiple, but a limited number of lineages. An example of a multipotent cell is a hematopoietic cell, a blood stem cell that can develop into several types of blood cells, but cannot develop into brain cells or other types of cells. Mesenchymal stem cells, or MSCs, are multipotent stem cells that into a variety of cell types including osteoblasts (bone cells), chondrocytes (cartilage cells) and adipocytes (fat cells).

A somatic cell is any type of cell forming the body of an organism with the exception of germ line cells (gametes), the cells from which gametes are made (gametocytes), multipotent cells and pluripotent cells. The somatic cell can be derived from any animal but is preferably a mammalian cell, most preferably a human cell. Suitable examples include liver cells such as hepatocytes, pancreatic cells such as beta cells, epithelial cells and fibroblasts, hepatocytes and pancreatic cells being preferred.

It must be appreciated that the methods of the inventions may not, and indeed need not, achieve the induction of all of the cells within a population of cells that is contacted with a short RNA of the invention. Thus, out of a population of cells subjected to the method of the present invention, i.e. contacted with a short RNA of the invention, preferably at least 10, 20, 30, 35, 38, 40, 42 or 45%, e.g. about 25-55%, 30-50%, 35-45%, may be induced to produce insulin, although in some embodiments at least 50, 60, 70, 80 or 90% are induced to produce insulin.

As used herein, the term "RNA" means a molecule comprising at least one ribonucleotide residue. By "ribonucleotide" is meant a nucleotide with a hydroxyl group at the 2' position of a beta-D-ribo-furanose moiety. The terms include double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the RNA or internally, for example at one or more nucleotides of the RNA. Nucleotides in the RNA molecules of the present invention can also comprise non-standard nucleotides, such as non-naturally occurring nucleotides or chemically synthesized nucleotides or deoxynucleotides. These altered RNAs can be referred to as analogs or analogs of naturally-occurring RNA.

The term "double stranded RNA" or "dsRNA" as used herein refers to a ribonucleic acid duplex, including but not limited to, endogenous and artificial siRNAs, short hairpin RNAs (shRNAs) and micro RNAs (miRNAs).

The term "short interfering RNA" or "siRNA" as used herein refers to a nucleic acid molecule capable of modulating gene expression through RNAi via sequence-specific-mediated cleavage of one or more target RNA transcripts. Typically in RNAi the RNA transcript is mRNA and so cleavage of this target results in the down-regulation of gene expression. In this invention however, up-regulation or down-regulation of the target gene can be achieved by cleavage of RNA transcripts which are antisense or sense to the target gene of interest respectively.

siRNAs are double-stranded RNA molecules of 19 to 25 base pairs in length with several unpaired bases on each 3' end forming a 3' overhang. Preferably, each 3' overhang is 1-3 nucleotides in length, more preferably 2. siRNAs contain one strand with a sequence of perfect or near perfect complementarity to a region of a target RNA transcript. A protein complex known as the RNA-induced silencing complex (RISC), incorporates this strand of the siRNA duplex (the guide strand) and uses it as a template to recognize the target RNA transcript. RISC is then involved in the cleavage of the target RNA transcript with perfect or near-perfect complementarity to the incorporated strand. The other strand of the siRNA molecule, which does not possess complementarity to a region of the target RNA transcript is termed the passenger strand.

Single stranded or double stranded RNA molecules which are not siRNA molecules but which are capable of down-regulating a target RNA transcript to which they have perfect or near-perfect complementarity by RISC-associated cleavage, are said to have siRNA-like activity. The short RNA molecules of the present invention have this activity.

In one embodiment, the short RNA molecules of the present invention may have miRNA-like complementarity to a region of the target transcript; that is, perfect complementarity between nucleotides 2-6 from the 5' end of the guide strand in the saRNA duplex and a region of the target transcript. Other nucleotides of the short RNA molecule may, in addition, have at least 70, 80, 90, 95, 99 or 100% complementarity to a region of the target transcript. For example, nucleotides 7 (counted from the 5' end) until the 3' end may have least 70, 80, 90, 95, 99 or 100% complementarity to a region of the target transcript.

By "complementarity" and "complementary" are meant that a first nucleic acid can form hydrogen bond(s) with a second nucleic acid for example by Watson-Crick base pairing. A nucleic acid which can form hydrogen bond(s) with another nucleic acid through non-Watson-Crick base pairing also falls within the definition of having complementarity. A percent complementarity indicates the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary).

"Perfectly complementary" or "perfect complementarity" means that all sequential residues of a first nucleic acid sequence will form hydrogen bonds with the same number of sequential residues in a second nucleic acid sequence. "Near-perfect" complementary means that essentially all sequential residues of a first nucleic acid sequence will form hydrogen bonds with the same number of sequential residues in a second nucleic acid sequence, however, due to the fact that the first nucleic acid is prepared by an imperfect process such as transcription or a molecular biological process involving the use of biological molecules, the first sequence may not be 100% complementary to the second sequence. However, the number of residues in the first sequence incapable of forming hydrogen bonds with the corresponding residues in the second sequence is sufficiently low that the two nucleic acid sequences are still bonded via hydrogen bonds to the extent required for the desired purpose. Typically, "near-perfect complementarity" means that a first nucleic acid sequence has at least 95% complementarity with a second nucleic acid sequence.

By "identity", "identical" or "sequence identity" is meant that a first nucleic acid is identical in sequence to a second nucleic acid sequence. A percent identity indicates the percentage of residues in a first nucleic acid molecule that are identical to a second nucleic acid sequence (e.g., 5, 6, 7, 8, 9, 10 out of 10 being 50%, 60%, 70%, 80%, 90%, and 100% identical).

"Perfect identity" or "perfectly identical" means that all sequential residues of a first nucleic acid sequence are identical to the same number of sequential residues in a second nucleic acid sequence. "Near-perfect" identity means that essentially all sequential residues of a first nucleic acid sequence are identical to the same number of sequential residues in a second nucleic acid sequence, however, due to the fact that the first nucleic acid is prepared by an imperfect process such as transcription or a molecular biological process involving the use of biological molecules, the first sequence may not be 100% identical to the second sequence. However, the number of residues in the first sequence which are not identical to the corresponding residues in the second sequence is sufficiently low that the two nucleic acid sequences are still sufficiently identical for the given purpose. Typically, "near-perfect identity" means that a first nucleic acid sequence has at least 95% identity with a second nucleic acid sequence.

All references to sequence complementarity or identity used herein refer to the whole length of the short RNA molecule unless specifically stated otherwise.

The short RNA may include a very short 3' or 5' sequence which is not complementary to the target RNA transcript. Preferably, such a sequence is 3'. Said sequence may be 1-5 nucleotides in length, preferably 2-3, e.g. 2 or 3. Said sequence preferably comprises or consists of uracil, so most preferably it is a 3' stretch of 2 or 3 uracils. This non-complementary sequence may be referred to as "tail". Thus, the short RNA preferably consists of (i) a sequence having at least 95% complementarity to a region of the target RNA; and (ii) a 3' tail of 1-5 nucleotides, which preferably comprises or consists of uracil residues. The short RNA will thus typically have complementarity to a region of the target RNA transcript over its whole length, except for the 3' tail, if present.

Any of the short RNA sequences disclosed herein may optionally include such a 3' tail. Thus, any of the sequences disclosed in the Tables may optionally include such a 3' tail.

Sequence alignments and percent identity or percent complementarity calculations may be determined using any method or tool known in the art including but not limited to the Megalign program of the LASARGENE bioinformatics computing suite (DNASTAR Inc., Madison, Wis.), the Clustal V method of alignment (Higgins and Sharp (1989) CABIOS. 5:151-153) and the BLAST 2.0 suite of programs. Software for performing BLAST analyses is publicly available, e.g., through the National Center for Biotechnology Information. The skilled man will be able to set the parameters of these tools to suit his desired purpose.

When assessing the identity or complementarity of a first and second nucleic acid sequence wherein one sequence is a DNA sequence and the other is an RNA sequence, it must be borne in mind that RNA sequences comprise uracil whereas DNA sequences would comprise thymine instead. Therefore, in these instances when assessing sequence identity, a uracil residue is considered to be identical to a thymine residue and when assessing complementarity a uracil residue is considered to be complementary to/capable of forming hydrogen bonds with an adenine residue.

By "inhibition" or "down-regulation" of a gene is meant a reduction of the level of expression of a gene(s), or levels of the polypeptide(s) encoded by a gene or the activity thereof, or levels of the RNA molecule(s) transcribed from a gene below that observed in the absence of the short RNA molecules of the present invention. If an RNA molecule is said to be "down-regulated" this means that the level of the RNA molecule is reduced below that observed in the absence of the short RNA molecules of the present invention.

By "activation" or "up-regulation" of a gene is meant an increase in the level of expression of a gene(s), or levels of the polypeptide(s) encoded by a gene or the activity thereof, or levels of the RNA molecule(s) transcribed from a gene above that observed in the absence of the short RNA molecules of the present invention.

Preferably all of the methods of the present invention are performed in vitro or ex vivo, although in vivo methods are also contemplated. Thus, they may be performed on cells or tissue samples that have previously been isolated from a subject. They may be performed on cells from established cell lines.

Preferably the "short" RNA molecule used in the above methods is from 13 nucleotides to 30 nucleotides in length, preferably from 15 or 17 to 30 nucleotides, more preferably 16 to 25 nucleotides in length, still more preferably 17 to 21 nucleotides in length, most preferably 19, 20, 21 or 22 nucleotides in length. In other words, the short RNA molecules may comprise a first strand of a length discussed above. If a 3' tail is present, the strand may be longer, preferably 19 nucleotides plus a 3' tail, which is preferably UU or UUU.

The short RNA molecule may be single or, preferably, double stranded. Double stranded molecules comprise a first strand and a second strand. If double stranded, preferably each strand of the duplex is at least 14, more preferably at least 18, e.g. 19, 20, 21 or 22 nucleotides in length. Preferably the duplex is hybridised over a length of at least 12, more preferably at least 15, more preferably 17, still more preferably at least 19 nucleotides. Each strand may be exactly 19 nucleotides in length. If a 3' tail is present, the strand may be longer, preferably 19 nucleotides plus a 3' tail, which is preferably UU or UUU.

Preferably the duplex length is less than 30 nucleotides since duplexes exceeding this length may have an increased risk of inducing the interferon response. The strands forming the dsRNA duplex may be of equal or unequal lengths.

Most preferably the short RNA molecule is a short interfering RNA (siRNA) molecule.

Optionally the short RNA molecules are dsRNA molecules which consist of the two strands stably base-paired together with a number of unpaired nucleotides at the 3' end of each strand forming 3' overhangs. The number of unpaired nucleotides forming the 3' overhang of each strand is preferably in the range of 1 to 5 nucleotides, more preferably 1 to 3 nucleotides and most preferably 2 nucleotides. The 3' overhang may be formed of the 3' tail mentioned above, so the 3' tail may be the 3' overhang.

The short RNA molecule must effectively and specifically down-regulate a target RNA transcript. As mentioned above, this can be achieved by the short RNA having a high degree of complementarity to a sequence within the target RNA transcript. The short RNA will have no more than 5, preferably no more than 4 or 3, more preferably no more than 2, still more preferably no more than 1, most preferably no mismatches with a region of a target RNA transcript.

The determination of the degree of complementarity of two or more sequences can be performed by any method known in the art. Preferably, the method used is that set out in Hossbach et al. (supra). In accordance with this method, the Perl script accessible at http://www.mpibpc.mpg.de/groups/luehrmann/siRNA is used.

In addition, various tools for the design and analysis of short RNA molecules are well-known, which permit one of ordinary skill in the art to determine those RNA molecules which can achieve effective and specific down-regulation of a target RNA transcript. Established methods include, for example, the GPboost and Reynolds algorithms (PMIDs: 15201190, 14758366). In addition, the ability of a short RNA to cause effective down-regulation of a target RNA can be evaluated using standard techniques for measuring the levels of RNA or protein in cells. For example, a short RNA of the invention can be delivered to cultured cells, and the levels of target RNA can be measured by techniques including but not limited to Northern blot or dot blotting techniques, or by quantitative RT-PCR.

Preferably the short RNAs possess none of the motifs aaaa, cccc, gggg, or uuuu. Preferably the short RNAs have a GC-percentage of at least 20% and no more than 75%, i.e. between 20% and 75%, preferably between 20% and 55%. The short RNAs of the above methods are ideally thermodynamically stable duplexes, in which case the GC percentage of each strand is at least 25% and no more than 75%, i.e. between 25% and 75%, preferably between 20% and 55%.

Tools and algorithms for determining whether or not RNAs possess the motifs aaaa, cccc, gggg or uuuu and for determining the percentage GC content of the molecules/strands are well known to the skilled artisan. Such tools include those described and referenced in Saetrom and Snove, (2004) *Biochem Biophys Res Commun* 321: 247-253 and Vert et al., (2006) *BMC Bioinformatics* 7: 520 (17 pages).

Short RNAs can induce down-regulation of non-target transcripts that have a limited number of mismatches to the short RNA strand which is incorporated into the RISC protein complex. This reduces the efficiency of the short RNA molecule and is therefore not desired. Consequently, short RNA molecules should have limited complementarity to transcripts other than the intended target to prevent unintended off-target effects. The probability of a short RNA candidate having cleavage-based off-target effects is a function of its complementarity to non-target RNA sequences and can be determined by any known method in the art. Optionally, an ungapped Smith-Waterman method (T F Smith & M S Waterman (1981) *Journal of molecular biology* 147: 195-197) can be used to screen the candidate short RNA against the Ensembl (Flicek, P., et al. (2008) Ensembl 2008. *Nucleic Acids Res* 36: D 707-714) human transcriptome database (Snøve, O., Jr., et al. (2004) *Biochem Biophys Res Commun* 325: 769-773) to identify a short RNA's potential off-target transcripts. Alternatively, the short RNA can be screened against a population of chosen RNA sequences, for example a selection of GenBank sequences, which do not encompass the entire Ensembl human transcriptome database. Alternatively a Hamming distance measure can be used.

Preferably, the short RNA molecules have more than two mismatches to the identified off-target transcripts. Alternatively viewed, preferably the short RNA molecules have a Hamming distance of 2 or greater to all potential off-target transcripts. If the short RNA is double stranded then preferably both strands satisfy this requirement.

Optionally, the short RNA molecules have characteristics in common with known highly effective standard siRNAs. Preferably, the short RNA, or if double stranded one or both strands of the short RNA, has a GPboost score of more than 0.1. GPboost is a known genetic programming-based prediction system of siRNA efficacy and the methods used for determining the GPboost score of siRNA strands is disclosed in "Predicting the efficacy of short oligonucleotides in antisense and RNAi experiments with boosted genetic programming", Pål Saetrom (2004) *Bioinformatics* 20(17): 3055-3063, the content of which is incorporated here by reference. Alternatively or in addition, the short RNA molecules possess specific sequence features which are associated with highly effective siRNAs. The algorithm described by Reynolds [Reynolds et al. (2004) *Nature biotechnology* 22(3):326-330], which is incorporated here by reference permits the determination of whether or not short RNAs possess sufficient features of this type. One of ordinary skill in the art would be able to define and refine his threshold for his particular purpose.

Optionally, the short RNA molecules contain position-specific sequence motifs which are associated with highly effective siRNAs. siRNA efficacy prediction algorithms are well-known in the art and motifs which are associated with highly-effective siRNAs are discussed in Saetrom and Snove, (2004) *Biochem Biophys Res Commun* 321: 247-253, the content of which is incorporated here by reference.

Preferably the short RNA molecule is capable of direct entry into the RNAi machinery of a cell or is capable of being processed by Dicer before entry into the RNAi machinery of a cell. Methods of determining whether or not a short RNA molecule is capable of being processed by Dicer before entry into the RNAi machinery of a cell are well-known in the art, for instance in vitro Dicer assays such as that disclosed in Tiemann et al. (2010) *RNA* 16(6): 1275-1284 and Rose et al. (2005) *Nucleic Acid Research* 33(13):4140-4156.

If the short RNA molecule is double stranded and if only one strand within the molecule is capable of effectively and specifically down-regulating the target RNA transcript then preferably that strand is preferentially loaded into RISC. The design of double-stranded RNA molecules in which one strand is preferentially loaded into RISC is within the competence of one of ordinary skill in the art. For instance, the 5' end of the strand of the short RNA molecule which targets the target RNA transcript can be made or selected to be less thermodynamically stable than the 5' end of the other strand. Preferably there is a large difference in duplex thermodynamic end stability such that the 5' end of the strand of the short RNA molecule which targets the target RNA transcript is less thermodynamically stable than the 5' end of the other strand. The absolute value of the difference in duplex thermodynamic end stability ($\Delta\Delta G$) can be calculated in accordance with any method standard in the art. Optionally, the absolute value of the difference in duplex thermodynamic end stability is calculated by RNAfold (Hofacker et al., (2003) *Nucleic Acids Research* Vol. 31, No. 13, pp 3429-3431) by considering the 5 closing nucleotides at the ends of the duplex. Preferably the absolute value of the difference in duplex thermodynamic end stability as calculated by RNAfold is more than 0 kcal/mol, more preferably more than 1 kcal/mol, more preferably more than 3 kcal/mol.

Many standard tools for short RNA design, such as those described above, provide means for assessing this property of the molecules. For instance, double-stranded molecules can be selected if they have thermodynamic properties which favour the incorporation of one strand over the other into the RNAi machinery. Alternatively, the preferential loading of one strand can be achieved by using dsRNAs which contain RNA that differs from naturally-occurring RNA by the addition, deletion, substitution and/or alteration of one or more nucleotides. Such modifications are well-known to the skilled man and are discussed further below.

Dicer is a ribonuclease protein which cleaves exogenous dsRNA into double-stranded fragments of 19 to 25 base pairs with several unpaired bases on each 3' end forming a 3' overhang. The short RNAs used in the above-methods may be Dicer-substrate siRNAs (D-siRNAs). siRNAs designed as Dicer substrates can have increased potency compared to standard length siRNAs and shRNAs.

D-siRNAs are asymmetric siRNA-duplexes in which the strands are between 22 and 30 nucleotides in length. Typically, one strand (the passenger strand) is 22 to 28 nucleotides long, preferably 25 nucleotides long, and the other strand (the guide strand) is 24 to 30 nucleotides long, preferably 27 nucleotides long, such that the duplex at the 3' end of the passenger strand is blunt-ended and the duplex has an overhang on the 3' end of the guide strand. The overhang is 1 to 3 nucleotides in length, preferably 2 nucleotides. The passenger strand may also contain a 5' phosphate.

Typically in D-siRNAs, the two nucleotides at the 3' end of the passenger strand are deoxyribonucleic acids (DNAs) rather than ribonucleic acids (RNAs). The DNAs and the blunt-ended duplex ensure that the enzyme Dicer processes the duplex into a 21mer duplex consisting of the 21 nucleotides at the 5' and 3' ends of the original D-siRNA's passenger and guide strands respectively.

Methods of extending standard 19mer siRNA molecules into D-siRNAs are well-known in the art, for instance as described in Hefner et al. (2008) *J. Biomol. Tech.* 19(4): 231-237.

When extended to 27mer/25mer D-siRNAs, many siRNA molecules have an end structure where the predicted number of unpaired bases at the 3' end of the passenger strand is less than or equal to the predicted number of unpaired bases at the 5' end of the guide strand. Based on the structure of known miRNAs and the binding requirements of the Dicer PAZ-domain, this structure is most likely suboptimal for Dicer processing and so, while useful as siRNA molecules, such duplexes are less useful when extended to Dicer-substrate siRNA molecules. Therefore, preferably the short RNAs of the present invention do not possess such a structure and rather the predicted number of unpaired bases at the 3' end of the passenger strand is greater than the predicted number of unpaired bases at the 5' end of the guide strand.

Optionally the short RNA molecules used in the above method can comprise modifications, i.e. RNA that differs from naturally-occurring RNA by the addition, deletion, substitution and/or alteration of one or more nucleotides. For instance, if the short RNA is double stranded, the two strands of the dsRNA molecule may be linked by a linking component such as a chemical linking group or an oligonucleotide linker with the result that the resulting structure of the dsRNA is a hairpin structure. The linking component must not block or otherwise negatively affect the activity of the dsRNA, for instance by blocking loading of strands into the RISC complex or association with Dicer. Many suitable chemical linking groups are known in the art. If an oligonucleotide linker is used, it may be of any sequence or length provided that full functionality of the dsRNA is retained. Preferably, the linker sequence contains higher amounts of uridines and guanines than other nucleotide bases and has a preferred length of about 4 to 9, more preferably 8 or 9 residues.

Modifications can be included in the short RNA, provided that the modification does not prevent the RNA composition from serving as a substrate for Dicer. One or more modifications can be made that enhance Dicer processing of the dsRNA, that result in more effective RNAi generation, that support a greater RNAi effect, that result in greater potency per each dsRNA molecule to be delivered to the cell and/or that are helpful in ensuring dsRNA stability in a therapeutic setting.

Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the RNA. Where multiple modifications are present, they may be the same or different. Modifications to bases, sugar moieties, the phosphate backbone, and their combinations are contemplated. Either 5'-terminus can be phosphorylated.

Short dsRNA molecules can be modified for Dicer processing by suitable modifiers located at the 3' end of the passenger strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddl), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). Deoxynucleotides can be used as the modifiers. When nucleotide modifiers are utilized, 1-3 nucleotide modifiers, or 2 nucleotide modifiers are substituted for the ribonucleotides on the 3' end of the passenger strand. When sterically hindered molecules are utilized, they are attached to the ribonucleotide at the 3' end of the passenger strand. Thus, the length of the strand does not change with the incorporation of the modifiers. Optionally two DNA bases are substituted in the dsRNA to direct the orientation of Dicer processing. Optionally, two terminal DNA bases are located on the 3' end of the passenger strand in place of two ribonucleotides forming a blunt end of the duplex on the 5' end of the guide strand and the 3' end of the passenger strand, and a two-nucleotide RNA overhang is located on the 3'-end of the guide strand. This is an asymmetric composition with DNA on the blunt end and RNA bases on the overhanging end.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like.

Locked nucleic acids, or LNA's, could also be incorporated. Many other modifications are known and can be used so long as the above criteria are satisfied.

The short RNAs of the invention can also comprise partially purified RNA, substantially pure RNA, synthetic RNA, or recombinantly produced RNA. Other possible alterations to the short RNAs include addition of non-nucleotide material to the end(s) of the short RNA or to one or more internal nucleotides of the short RNA; modifications that make the short RNA resistant to nuclease digestion (e.g., the use of 2'-substituted ribonucleotides or modifications to the sugar-phosphate backbone); or the substitution of one or more nucleotides in the short RNA with deoxyribonucleotides.

If the short RNA is double stranded, preferably both strands are capable of effectively and specifically down-regulating a target RNA transcript as defined above. Methods of designing such multi-functional siRNA molecules are disclosed in Hossbach et al., (2006) *RNA Biology* 3 (2): 82-89, the content of which is incorporated here by reference.

If the short RNA is double stranded and both strands are capable of effectively and specifically down-regulating a target RNA transcript as defined above then preferably there is not a large difference in duplex thermodynamic end stability. The absolute value of the difference in duplex thermodynamic end stability ($\Delta\Delta G$) can be calculated in accordance with any method standard in the art. Optionally, the absolute value of the difference in duplex thermodynamic end stability is calculated by RNAfold (Hofacker et al., (2003) *Nucleic Acids Research* Vol. 31, No. 13, pp 3429-3431) by considering the 5 closing nucleotides at the ends of the duplex. Preferably the absolute value of the difference in duplex thermodynamic end stability as calculated by RNAfold is less than 3 kcal/mol, more preferably less than 1 kcal/mol.

In the methods of the present invention, the induction of specialisation is achieved by up-regulating, i.e. activating, a target specialisation-inducing gene(s). The up-regulation is "cis" up-regulation. In this context "cis" up-regulation means that the target RNA transcript is transcribed from a locus which is associated with the locus of the target gene. Such "association" can be in one of three ways:

Firstly, the target RNA transcript can be transcribed from a locus up to 100 kb upstream of the target gene's transcription start site. Secondly, the target RNA transcript can be transcribed from a locus up to 100 kb downstream of the target gene's annotated transcription stop site. Thirdly, the target RNA transcript can be transcribed from a locus which interacts physically with the target gene. In this latter case, the target RNA transcript may be transcribed from a locus of any distance from the target gene's transcription start site or even on a different chromosome. It is well-known in the field that different regions of DNA are capable of long-range interactions either within the same chromosome or within different chromosomes [Lieberman-Aiden et al. (2009) Science 326: 289-293]. The first two ways are preferred.

In contrast, "trans" up-regulation would occur if the target RNA transcript was not transcribed from a locus which was either within 100 kb upstream of the target gene's transcription start site or within 100 kb downstream of the target gene's transcription stop site and was not transcribed from a locus which interacts physically with the target gene. In the methods of the present invention "trans" up-regulation is not contemplated.

Thus, the target RNA transcripts of the above methods are transcribed from a locus up to 100, 80, 60, 40, 20 or 10 kb upstream of the target gene's transcription start site, from a locus up to 100, 80, 60, 40, 20 or 10 kb downstream of the target gene's transcription stop site, or from a locus which interacts physically with the target gene. Optionally, the RNA transcripts are transcribed from a locus up to 1 kb upstream of the target gene's transcription start site or from a locus up to 1 kb downstream of the target gene's transcription stop site. Optionally, the RNA transcripts are transcribed from a locus up to 500, 250 or 100 nucleotides upstream of the target gene's transcription start site or from a locus up to 500, 250 or 100 nucleotides downstream of the target gene's transcription stop site, more preferably the locus is no more than 500 nucleotides upstream or downstream from the target gene's transcription start site. Most preferably the target RNA transcript is transcribed from a locus up to 500 nucleotides upstream or up to 500 nucleotides downstream of the target gene's transcription start site.

The term "is transcribed from [a particular locus]" in the context of the target RNA transcripts of the invention means "the transcription start site of the target RNA transcript is found [at the particular locus]". The transcription start site of the target RNA transcript may be found on either strand of the chromosome containing the target gene, provided that the other essential features of the target RNA transcript are present. Preferably, the target RNA transcript of the present invention has its transcription start site and its transcription stop site within one of the regions i)a) or i)b) defined above. In other words, preferably both of the transcription start site and the transcription stop site of the target RNA transcript are, separately, located either up to 100 kb upstream of the target gene's transcription start site or up to 100 kb downstream of the target gene's transcription stop site. The preferred embodiments described above in relation to the location from which the target RNA transcript is transcribed apply mutatis mutandis to the location of the target RNA transcript's transcription stop site.

In the above methods, the target RNA transcript comprises a sequence which is antisense to a genomic sequence located between 100, 80, 60, 40, 20 or 10 kb upstream of the target gene's transcription start site and 100, 80, 60, 40, 20 or 10 kb downstream of the target gene's transcription stop site. More preferably, the target RNA transcript comprises a sequence which is antisense to a genomic sequence located between 1 kb upstream of the target gene's transcription start site and 1 kb downstream of the target gene's transcription stop site. More preferably, the target RNA transcript comprises a sequence which is antisense to a genomic sequence located between 500, 250 or 100 nucleotides upstream of the target gene's transcription start site and ending 500, 250 or 100 nucleotides downstream of the target gene's transcription stop site. Optionally the target RNA transcript comprises a sequence which is antisense to a genomic sequence which includes the coding region of the target gene.

The target RNA transcript is preferably at least 1 kb, more preferably at least 2, 3, 4, 5, 6, 7, 8, 9 or 10, e.g. 20, 25, 30, 35 or 40 kb long. Preferably, the sequence of the target RNA transcript which is antisense to a genomic sequence located between 100 kb upstream of the target gene's transcription start site and 100 kb downstream of the target gene's transcription stop site is at least 1 kb, more preferably at least 2, 3, 4, 5, 6, 7, 8, 9 or 10, e.g. 20, 25, 30, 35, 40, 50, 70 or 80 kb long.

The term "sense" when used to describe a nucleic acid sequence in the context of the present invention means that the sequence has identity to a sequence on the coding strand of the target gene. The term "antisense" when used to describe a nucleic acid sequence in the context of the present invention means that the sequence is complementary to a sequence on the coding strand of the target gene.

The "coding strand" of a gene is the strand which contains the coding sequence for the gene's mRNA. The "template strand" of a gene is the strand which does not contain the coding sequence for the gene's mRNA.

The terms "complementary" and "complementarity" are defined above. Preferably the target RNA transcript comprises a sequence which is at least 75%, preferably at least 85%, more preferably at least 90%, still more preferably at least 95% complementary along its full length to a sequence on the coding strand of the target gene. Preferably the target RNA transcript comprises a sequence which has perfect or near-perfect complementarity along its full length to a sequence on the coding strand of the target gene.

Alternatively, the target RNA transcript comprises one or more, usually several (e.g. at least 3 or at least 6), un-gapped sequences which have perfect or near-perfect complementarity to a sequence on the coding strand of the target gene, said un-gapped sequence being at least 16 nucleotides, more preferably at least 25 nucleotides, more preferably at least 50 nucleotides, still more preferably at least 75 nucleotides, most preferably at least 100 nucleotides in length.

In several aspects of the present invention the target RNA transcript may comprise a sequence which is sense to a sequence within the target gene, i.e. the target RNA transcript may comprise a sequence with identity to a sequence on the coding strand of the target gene. The terms "identity" and "identical" are defined above. Preferably the target RNA transcript comprises a sequence which is at least 75%, preferably at least 85%, more preferably at least 90%, still more preferably at least 95% identical along its full length to a sequence on the coding strand of the target gene. Preferably the target RNA transcript comprises a sequence which has perfect or near-perfect identity along its full length to a sequence on the coding strand of the target gene.

Alternatively, the target RNA transcript comprises one or more, usually several (e.g. at least 3 or at least 6), un-gapped sequences which have perfect or near-perfect identity to a sequence on the coding strand of the target gene, said un-gapped sequence being at least 16 nucleotides, more preferably at least 25 nucleotides, more preferably at least 50 nucleotides, still more preferably at least 75 nucleotides, most preferably at least 100 nucleotides in length.

When assessing identity/complementarity between the RNA transcript(s) and the above-mentioned genomic sequence(s), the coding/template strands are considered to extend upstream and downstream of the gene's transcribed region, i.e. the terms "coding strand" and "template strand" are merely labels for the actual strands and do not indicate any length limitation.

The target RNA transcript is either a coding RNA molecule, i.e. an RNA molecule which codes for an amino acid sequence, or it is a non-coding RNA molecule, i.e. an RNA molecule which does not code for an amino acid sequence. Preferably the target RNA transcript is a non-coding RNA.

The target RNA transcripts are preferably at least 16 nucleotides in length. Preferably however the target RNA transcripts are at least 100, more preferably at least 200 nucleotides in length, most preferably at least 1000 nucleotides in length, possibly at least four thousand nucleotides in length.

In the above methods, the target RNA transcript comprises a sequence which is antisense to a genomic sequence located between 100 kb upstream of the target gene's transcription start site and 100 kb downstream of the target gene's transcription stop site. For the sake of clarity, from herein the term "genomic sequence" is used as a short hand for the term "genomic sequence located between 100 kb upstream of the target gene's transcription start site and 100 kb downstream of the target gene's transcription stop site". In other words, the target RNA transcript comprises a sequence which is complementary to a genomic sequence on the coding strand of the target gene.

Optionally, the genomic sequence to which the target RNA transcript is antisense comprises part of a promoter region of the target gene. In other words, optionally the target RNA transcript comprises a sequence which is antisense to a genomic sequence located between 100 kb upstream of the target gene's transcription start site and 100 kb downstream of the target gene's transcription stop site and which comprises part of a promoter region of the target gene. Another way of describing this feature is that the antisense target RNA transcript "overlaps" a promoter region of the target gene. Genes may possess a plurality of promoter regions, in which case the target RNA transcript may overlap with one, two or more of the promoter regions. Online database of annotated gene loci may be used to identify the promoter regions of genes.

For any given promoter region, the entire promoter region does not have to be overlapped, it is sufficient for a subsequence within the promoter region to be overlapped by the target RNA transcript, i.e. the overlap can be a partial overlap. Similarly, the entire target RNA transcript need not be antisense to the sequence within the promoter region, it is only necessary for the target RNA transcript to comprise a sequence which is antisense to the promoter region.

The region of overlap between the target RNA transcript and the promoter region of the target gene may be as short as a single nucleotide in length, although it is preferably at least 15 nucleotides in length, more preferably at least 25 nucleotides in length, more preferably at least 50 nucleotides in length, more preferably at least 75 nucleotides in length, most preferably at least 100 nucleotides in length. Each of the following specific arrangements are intended to fall within the scope of the term "overlap":

a) The target RNA transcript and the target gene's promoter region are identical in length and they overlap (i.e. they are complementary) over their entire lengths.

b) The target RNA transcript is shorter than the target gene's promoter region and overlaps over its entire length with the target gene's promoter region (i.e. it is complementary over its entire length to a sequence within the target gene's promoter region).

c) The target RNA transcript is longer than the target gene's promoter region and the target gene's promoter region is overlapped fully by it i.e. the target gene's promoter region is complementary over its entire length to a sequence within the target RNA transcript).

d) The target RNA transcript and the target gene's promoter region are of the same or different lengths and the region of overlap is shorter than both the length of the target RNA transcript and the length of the target gene's promoter region.

The above definition of "overlap" applies mutatis mutandis to the description of other overlapping sequences throughout the description. Clearly, if an antisense RNA transcript is described as overlapping with a region of the target gene other than the promoter region then the sequence of the transcript is complementary to a sequence within that region rather than within the promoter region. If referring to a sense target RNA transcript, the term "overlap" means that the target RNA transcript comprises a sequence which is sense to a sequence within the promoter region or other stated region of the target gene. In other words, the sense target RNA transcript comprises a sequence which is identical/has identity with a sequence on the coding strand of the target gene and within the specified region of the target gene.

Preferably the RNA transcript comprises a sequence which is antisense to a genomic sequence which comprises the target gene's transcription start site. In other words, preferably the target RNA transcript comprises a sequence which overlaps with the target gene's transcription start site.

Without wishing to be bound by theory, it is believed that the short RNAs of the present invention achieve modulation of the target gene by inducing the siRNA-like cleavage of the target RNA transcript which is antisense (or, in some cases, sense) to a region of the target gene. Short RNAs of the present invention might also be able to act, in complex with Argonaute proteins, as anchors for regulatory chromatin-modifying proteins. The exact mechanism is unknown, however, it is clear that the target RNA transcript must be present in the cell in order for an effect to be observed.

Methods of determining the target RNA transcripts present in a cell are well-known in the art. For instance, the genomic region around the locus of the gene of interest can be searched for spliced expresses sequence tags. An expressed sequence tag or EST is a short sub-sequence of a transcribed cDNA sequence. ESTs are commonly used to identify gene transcripts. Public databases of ESTs are known in the art, for instance the GenBank database. Alternatively, Reverse Transcriptase PCR (RT-PCR), a well-known tool for identifying RNA, can be used to identify potential target RNA transcripts. Alternatively, high throughput sequencing or other such methods can be used to sequence total, size-fractionated, or other suitable subsets of RNAs and use such sequencing libraries to identify RNA transcripts that originate from the region of interest. Alternatively, a population of known RNA transcripts can be searched to identify suitable transcripts. Any database of RNA transcripts known in the art can be used, for instance the University of California Santa Cruz (UCSC) Spliced EST track. Alternatively the population may be prepared from a population possessed by the skilled man working the invention for his own specific purposes. For instance, if the target gene is known to be expressed in a particular cell type, then the database of transcripts may be those which have been determined to be present in that cell type. The skilled man will be able to determine the population to use for his specific desired purposes.

However, for the purpose of the present invention the positive identification of any RNA transcripts which are antisense to the target gene is not in fact required. Thus, the existence of said non-coding RNA transcript (i.e. the target transcript to be down-regulated) need not be determined. The present inventor found that if the nucleotide sequence of the coding strand of the gene in the region surrounding the gene's transcription start site is obtained, i.e. determined by sequencing or found on a database, and the reverse complementary RNA sequence to that region is determined, then short RNA molecules which are complementary to that latter sequence can be used to up-regulate the target gene. Complementarity requirements are discussed elsewhere herein. The region surrounding the gene's transcription start site is the region located between 100, 200, 300, 400, 500, 800, 1000 or 2000 nucleotides upstream and downstream of the transcription start site.

Without wishing to be bound by theory, it is believed that the saRNA mechanism of action may involve chromatin remodelling, for example, through Polycomb group proteins. Polycomb group proteins can apparently directly interact with ncRNAs, including promoter-associated RNAs, and thereby be recruited to promoters and effect silencing. The saRNAs may therefore, by interfering with such Polycomb-recruiting ncRNAs, reduce Polycomb-levels at promoters and allow "positive" chromatin remodeling complexes such as Trithorax group proteins to establish positive histone marks.

The above-discussed methods require the use of short RNAs to up-regulate a target gene, i.e. at least one target specialisation-inducing gene. The methods therefore permit those specialisation inducing genes not activated by the use of the short RNAs of the invention to be activated by other means known in the art. Preferably, the above methods comprise the up-regulation of 2, 3, 4, 5, 6, 7 or 8 target genes selected from the group consisting of PDX1, Neurogenin 3 (Ngn3), Rfx6, MafA, GLP1 receptor, FOXA2, HNF1A, Hlxb9, Hnf6, Ptf1a, Neuro D, betacellulin, ABCC8, glucokinase (GCK), GLUT2, Nkx6-1 and (pro)insulin, more preferably PDX1, Ngn3, Rfx6 and MafA by using the short RNAs of the invention. Any combination of these target genes is contemplated. Preferably, at least one of the target genes up-regulated by the short RNAs of the present invention is MafA.

Figure 7:
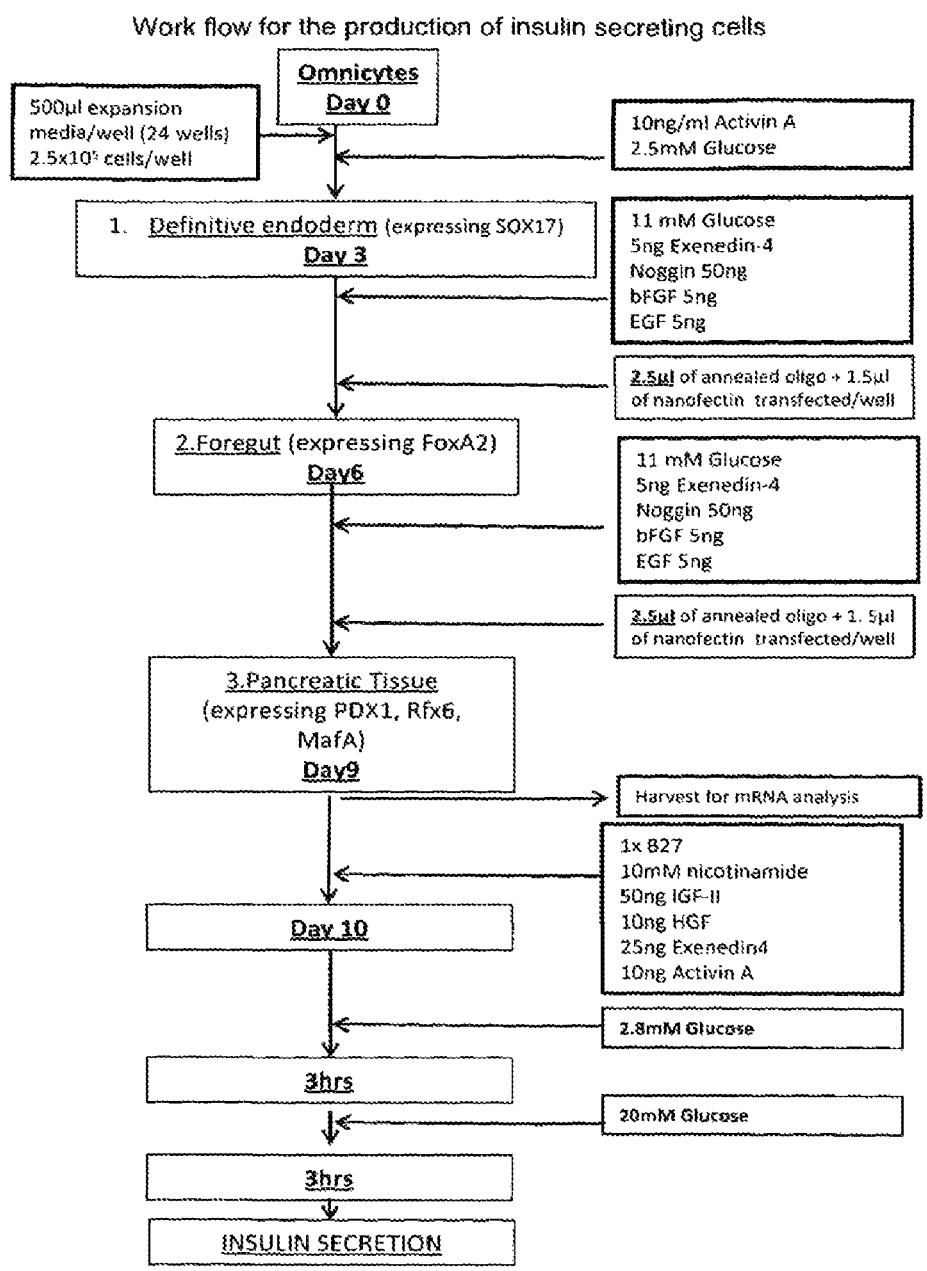
Figure 14:
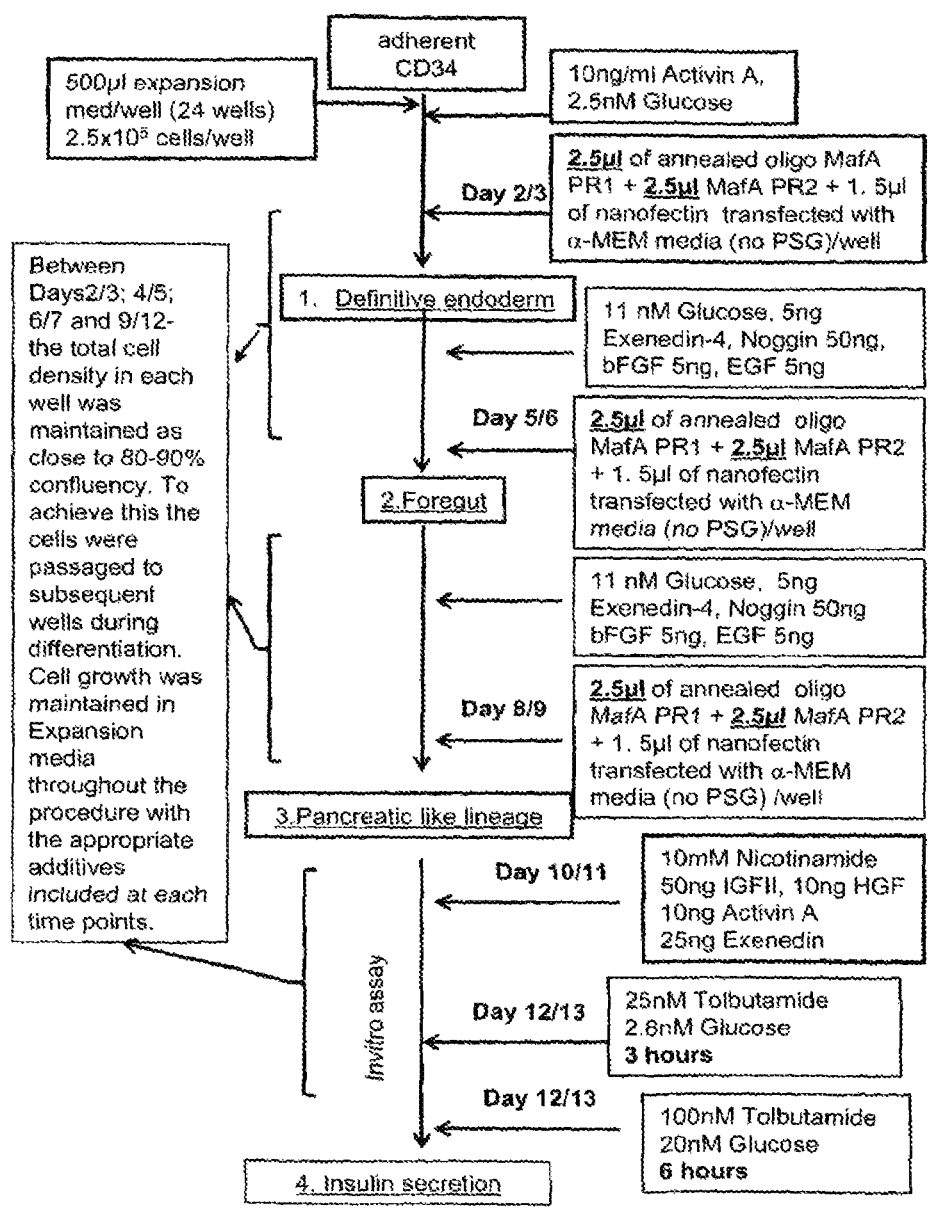

The methods of the present invention may additionally involve contacting the cells with appropriate factors. Appropriate factors may preferably be selected from glucose, activin, exendin (preferably exendin-4), noggin, FGF, nicotinamide, tolbutamine, IGF-II, HGF and/or EGF. In one embodiment, the cells are contacted with glucose, preferably about 2.5 mM or 2.5 nM, and/or activin A, preferably about 10 ng, for at least 1 day, preferably 2-4 days, e.g. 3 days. In one embodiment, the cells are contacted with glucose, preferably about 11 mM or 11 nM, exendin, preferably about 5 ng, noggin, preferably 50 ng, FGF, preferably 5 ng and/or EGF, preferably 5 ng, for about 6 days, e.g. 4-8 days. Said contacting may be repeated at appropriate intervals, e.g. every 3 days. In one embodiment, the cells are first contacted with glucose and activin A for about 3 days, followed by contacting at days 3 and 6 with glucose, exendin, noggin, FGF and EGF. In one embodiment, the cells are contacted, preferably at day 9, with nicotinamide, preferably about 10 mM, IGF-II, preferably about 50 ng, HGF, preferably about 10 ng, exendin-4, preferably about 25 ng, and activin A, preferably about 10 ng. Preferably, pencillin, streptomycin and glutamine and not present during any of these steps. Exemplary workflows are shown in FIGS. 7 and 14. Each step of the workflow shown in these Figures represents a separate embodiment.

In the method of the invention the cell or population of cells is contacted with a short RNA molecule of the present invention. The short RNA molecules can be administered to said cells in vitro or in vivo by using any suitable delivery reagents in conjunction with the present short RNAs. Such suitable delivery reagents include the Mirus Transit TKO lipophilic reagent; lipofectin; lipofectamine; cellfectin; or polycations (e.g., polylysine), virus-based particles, electroporation or liposomes. A preferred delivery reagent is a liposome. A variety of methods are known for preparing liposomes, for example as described in Szoka et al. (1980), *Ann. Rev. Biophys. Bioeng.* 9: 467; and U.S. Pat. Nos. 4,235,871 and 5,019,369, the entire disclosures of which are herein incorporated by reference.

The step of contacting cells with saRNAs may also be referred to as "transfection".

Particularly preferably, the liposomes encapsulating the present short RNAs are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Recombinant plasmids which can express the short RNAs can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express the short RNA and methods for delivering such vectors to a cell are known within the art.

Preferably said contacting step is performed more than once, preferably every 3 days, although it may also be daily, or every 2, 4 or 5 days. The contacting is preferably performed for at least 1, 2, 3, 4, 5, 6, 7, 8, 9, 10, 11, 12, 13, 14 or 15 days, about 6 or 9 days being preferred.

In the methods disclosed herein, if more than one target gene is up-regulated then the short RNAs used to up-regulate the different target genes may be administered at different frequencies and for different lengths of time. The particular administration regimens to be used can be readily determined by one of ordinary skill in the art to suit his desired purpose, particular starting cell type and delivery method. By way of example, picoMolar concentrations of the short RNA molecules of the present may be used.

The short RNA of the invention may be provided alone or in combination with other active agent(s) known to have an effect in the particular method being considered. The other active agent(s) may be administered simultaneously, separately or sequentially with the short RNA of the invention. Thus, it is possible to use a single short RNA of the invention, a combination of two or more short RNAs of the invention or, if applicable, a combination of said short RNA(s) and other active substance(s).

In a further aspect the present invention provides a method of up-regulating a target gene, wherein said target gene is a specialisation-inducing gene and wherein said method comprises contacting a cell comprising said target gene with a short RNA molecule which specifically down-regulates a target RNA transcript present in said cell, wherein said target RNA transcript:
i) is transcribed from
a) either strand of a locus up to 100 kb upstream of the target gene's transcription start site,
b) either strand of a locus up to 100 kb downstream of the target gene's transcription stop site; or
c) either strand of a locus which interacts physically with the target gene; and
ii) comprises a sequence which is antisense to a genomic sequence located between 100 kb upstream of the target gene's transcription start site and 100 kb downstream of the target gene's transcription stop site.

The definitions and description above in relation to the methods of inducing specialisation or maintaining, inducing or increasing the producing of a target protein apply mutatis mutandis to this method of up-regulating a target specialisation-inducing gene.

In a further aspect the present invention provides a method of down-regulating a target gene, wherein said target gene inhibits specialisation and wherein said method comprises contacting a cell comprising said target gene with a short RNA molecule which specifically down-regulates a target RNA transcript present in said cell, wherein said target RNA transcript:
i) is transcribed from
a) either strand of a locus up to 100 kb upstream of the target gene's transcription start site,
b) either strand of a locus up to 100 kb downstream of the target gene's transcription stop site; or
c) either strand of a locus which interacts physically with the target gene; and
ii) comprises a sequence which is sense to a genomic sequence located between 100 kb upstream of the target gene's transcription start site and 100 kb downstream of the target gene's transcription stop site.

The above method can be used in isolation or, if desired, as an additional step in the above-discussed methods.

Unless otherwise stated, the definitions and description above apply mutatis mutandis to this method of down-regulating a target gene which inhibits specialisation.

In this method of down-regulating a target gene which inhibits specialisation, the down-regulation is "cis" down-regulation. The term "cis" in this context is as described above.

In this method of down-regulating a target gene which inhibits specialisation, the target RNA transcript is sense to the target gene. The term "sense" is as described above.

In this method of down-regulating a target gene which inhibits specialisation, the target RNA transcript comprises a sequence which is sense to a genomic sequence located between 100 kb upstream of the target gene's transcription start site and 100 kb downstream of the target gene's transcription stop site. In other words, the target RNA transcript comprises a sequence which is identical/has identity to a sequence on the coding strand of the target gene located between 100 kb upstream of the target gene's transcription start site and 100 kb downstream of the target gene's transcription stop site.

Optionally, the genomic sequence to which the target RNA transcript is sense comprises part of a promoter region of the target gene. In other words, optionally the target RNA transcript comprises a sequence which is sense to a genomic sequence located between 100 kb upstream of the target gene's transcription start site and 100 kb downstream of the target gene's transcription stop site and which comprises part of a promoter region of the target gene. Another way of describing this feature is that the sense target RNA transcript "overlaps" a promoter region of the target gene. Genes may possess a plurality of promoter regions, in which case the target RNA transcript may overlap with one, two or more of the promoter regions. Online database of annotated gene loci may be used to identify the promoter regions of genes.

For any given promoter region, the entire promoter region does not have to be overlapped, it is sufficient for a subsequence within the promoter region to overlapped by the target RNA transcript i.e. the overlap can be a partial overlap. Similarly, the entire target RNA transcript need not be sense to the sequence within the promoter region, it is only necessary for the target RNA transcript to comprise a sequence which is sense to the promoter region. The regions of overlap are as defined above.

Preferably the RNA transcript comprises a sequence which is sense to a genomic sequence which comprises the target gene's transcription start site. In other words, preferably the target RNA transcript comprises a sequence which overlaps with the target gene's transcription start site.

A key feature of all aspects of the present invention is that targeting antisense RNA transcripts with the short RNAs of the present invention leads to up-regulation of the target gene while targeting sense RNA transcripts leads to down-regulation of the target gene.

In a further aspect the present invention provides a short RNA molecule which specifically up-regulates a target gene in a cell by down-regulating a target RNA transcript present in said cell, wherein said target gene is a specialisation-inducing gene and wherein said target RNA transcript:
i) is transcribed from
  a) either strand of a locus up to 100 kb upstream of the target gene's transcription start site,
  b) either strand of a locus up to 100 kb downstream of the target gene's transcription stop site; or
  c) either strand of a locus which interacts physically with the target gene; and
ii) comprises a sequence which is antisense to a genomic sequence located between 100 kb upstream of the target gene's transcription start site and 100 kb downstream of the target gene's transcription stop site.

In a further aspect the present invention provides a short RNA molecule which specifically down-regulates a target gene in a cell by down-regulating a target RNA transcript present in said cell, wherein said target gene is a gene which inhibits specialisation and wherein said target RNA transcript:
i) is transcribed from
  a) either strand of a locus up to 100 kb upstream of the target gene's transcription start site,
  b) either strand of a locus up to 100 kb downstream of the target gene's transcription stop site; or
  c) either strand of a locus which interacts physically with the target gene; and
ii) comprises a sequence which is sense to a genomic sequence located between 100 kb upstream of the target gene's transcription start site and 100 kb downstream of the target gene's transcription stop site.

Unless otherwise stated, the definitions and description above in relation to the methods of the present invention apply mutatis mutandis to the product aspects of the present invention.

Short activating RNAs (saRNA) are preferred. More particularly, the present invention provides an saRNA which is capable of inducing insulin production in a cell by up-regulating a target gene involved in insulin production in said cell by specifically down-regulating a target RNA transcript present in said cell. Preferably, said target RNA transcript is complementary to a sequence located on the coding strand of the target gene between 2000, 1000, or 500 nucleotides upstream and 2000, 1000, or 500 nucleotides downstream of the transcription start site of the target gene. Preferably said saRNA is a single or double stranded RNA molecule up to 30 nucleotides in length comprising a sequence of at least 13 nucleotides which has at least 95% complementarity to a region of the target transcript.

Thus, preferably there is provided an saRNA which is capable of inducing insulin production in a cell by up-regulating a target gene involved in insulin production in said cell by specifically down-regulating a target RNA transcript present in said cell, wherein
(i) said target RNA transcript is complementary to a sequence located on the coding strand of the target gene between 1000 nucleotides upstream and 1000 nucleotides downstream of the transcription start site of the target gene; and
(ii) said sRNA is a single or double stranded RNA molecule up to 30 nucleotides in length comprising a sequence of at least 13 nucleotides which has at least 95% complementarity to a region of the target transcript.

Preferably, the sequence which has at least 95% complementarity to a region of the target transcript is at least 15-20, e.g. at least 15, 16, 17, 18 or 19 nucleotides in length, preferably 18-22 or 19 to 21, most preferably exactly 19. As mentioned above, the saRNA may also comprise a 3' tail.

The short RNA molecules of the invention can be produced by any suitable method, for example synthetically or by expression in cells using standard molecular biology techniques which are well-known to the skilled artisan. For example, the short RNAs can be chemically synthesized or recombinantly produced using methods known in the art, such as the *Drosophila* in vitro system described in U.S. published application 2002/0086356 of Tuschl et al., or the methods of synthesizing RNA molecules described in Verma and Eckstein (1998) *Annu Rev Biochem* 67: 99-134, the entire disclosures of which are herein incorporated by reference. The short RNAs of the invention may be chemically synthesized using appropriately protected ribonucleoside phosphoramidites and a conventional DNA/RNA synthesizer. If the short RNAs are double-stranded RNAs then they can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

The short RNAs can also be expressed from recombinant circular or linear DNA plasmids using any suitable promoter. Suitable promoters for expressing short RNAs of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the short RNA in a particular tissue or in a particular intracellular environment.

The short RNAs expressed from recombinant plasmids can be isolated from cultured cell expression systems by standard techniques. The double stranded short RNAs of the invention can be expressed from a recombinant plasmid either as two separate, complementary RNA molecules, or as a single RNA molecule with two complementary regions.

Selection of plasmids suitable for expressing short RNAs of the invention, methods for inserting nucleic acid sequences for expressing the short RNAs into the plasmid, and methods of delivering the recombinant plasmid to the cells of interest are within the skill in the art. See, for example Tuschl, T. (2002), *Nat. Biotechnol.* 20: 446-448 and Brummelkamp T R et al. (2002), *Science* 296: 550-553, the entire disclosures of which are herein incorporated by reference.

The short RNAs of the invention can also be expressed from recombinant viral vectors intracellularly in vivo. The recombinant viral vectors of the invention comprise sequences encoding the short RNAs of the invention and any suitable promoter for expressing the short RNA sequences. Suitable promoters include, for example, the U6 or H1 RNA pol III promoter sequences and the cytomegalovirus promoter. Selection of other suitable promoters is within the skill in the art. The double stranded short RNAs of the invention can be expressed from a recombinant viral vector either as two separate, complementary RNA molecules, or as a single RNA molecule with two complementary regions. Any viral vector capable of accepting the coding sequences for the dsRNAs molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

Selection of recombinant viral vectors suitable for use in the invention, methods for inserting nucleic acid sequences for expressing the short RNA into the vector, and methods of delivering the viral vector to the cells of interest are within the skill in the art. See, for example, Dornburg R (1995), *Gene Therap.* 2: 301-310, the entire disclosure of which is herein incorporated by reference.

As discussed in the Examples, using the methods disclosed herein, the present inventor has designed specific short RNA molecules which effectively modulate the activity of numerous specialisation genes. Preferred specialisation genes are discussed above. Thus, in a further aspect the present invention provides short RNA molecules, which may be single or double stranded, with the specific sequences shown in Tables 1-7. As mentioned above, any of the sequences listed in the Tables may optionally have a 3' tail, preferably UU or UUU.

Thus, provided are short RNAs having a first strand comprising or consisting of a sequence selected from SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 1, 2, 3 and 4. Optionally, the short RNA may comprise a 3' tail at the 3' end of any of these sequences.

Single stranded short RNA molecules only consist of a first strand, whereas double stranded short RNA molecules also have a second strand. The short RNAs may thus have a second strand comprising or consisting of a sequence selected from SEQ ID NOs 45 to 88, i.e. the sense sequences of Table 7, optionally with a 3' tail.

Short RNAs having a first strand comprising or consisting of a sequence selected from SEQ ID NOs: 1 to 22, optionally with a 3' tail, are preferred.

Short RNAs having a first strand comprising or consisting of a sequence selected from SEQ ID NOs: 5 and 6, optionally with a 3' tail, are especially preferred. In one preferred embodiment, the short RNA has a first strand comprising or consisting of a sequence of SEQ ID NO: 5, optionally with a 3' tail, and a second strand or consisting of a sequence of SEQ ID NO: 49 optionally with a 3' tail. In another preferred embodiment, the short RNA has a first strand comprising or consisting of a sequence of SEQ ID NO: 6, optionally with a 3' tail, and a second strand or consisting of a sequence of SEQ ID NO: 50, optionally with a 3' tail.

In embodiments of any of the aspects disclosed herein, the use of a combination of a saRNA having a first strand comprising or consisting of a sequence of SEQ ID NO: 5 with an saRNA having a first strand comprising or consisting of a sequence of SEQ ID NO: 6 is most preferred.

The invention also provides single-stranded or double-stranded RNA molecules comprising or consisting of the above individual strand sequences.

The invention also provides DNA molecules equivalent to the above mentioned RNA molecules.

The short RNA molecules of the invention may be used directly in therapeutic methods, including methods of regeneration or repair.

In a further aspect the present invention provides a short RNA of the present invention for use in therapy. A preferred embodiment is an saRNA which is capable of inducing insulin production in a cell by up-regulating a target gene involved in insulin production in said cell by specifically down-regulating a target RNA transcript present in said cell for use in therapy, wherein
(i) said target RNA transcript is complementary to a sequence located on the coding strand of the target gene between 1000 nucleotides upstream and up to 1000 nucleotides downstream of the transcription start site of the target gene; and
(ii) said saRNA is a single or double stranded RNA molecule up to 30 nucleotides in length comprising a sequence of at least 13 nucleotides which has at least 95% complementarity to a region of the target transcript.

Also provided is an saRNA comprising or consisting of the sequence of SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 1, 2, 3 and 4, optionally with a 3' tail, for use in therapy.

In a further aspect, the invention provides a method of gene therapy comprising administering to a patient in need thereof a short RNA of the invention.

The present invention provides a short RNA of the invention for use in the treatment of a disease associated with a deficiency of specialised cells, preferably insulin producing cells, in a patient.

In a further aspect the present invention provides a cell or cell line comprising a short RNA of the present invention.

In a further aspect the present invention provides a specialised cell prepared by any one of the methods of the present invention.

As set out in the Examples, the methods of the invention allow the generation of cells capable of secreting insulin. Thus, in a further aspect there is provided a cell capable of producing insulin obtainable by the methods disclosed herein. Preferably, the cell is obtained by inducing a CD34+ stem cell such as an OmniCyte to specialise.

The cell is preferably ex vivo, i.e. not part of a living organism. Optionally, the cell may be referred to as "in vitro" or "isolated".

Uses of such cells in therapy represents a further aspect of the invention.

Optionally, the specialised cell of the present invention and short RNA of the present invention may be used in combination in the therapeutic applications disclosed herein. "In combination" includes separate, simultaneous or sequential administration.

Alternatively viewed, the present invention provides a method of treatment comprising administering to a subject in need thereof a therapeutically effective amount of a specialised cell and/or a therapeutically effective amount of a short RNA as defined herein.

The therapeutic application may be the treatment of any condition, injury or disorder that can benefit from the administration of a specialised cell and/or short RNA molecule of the invention. This may be a condition associated with or characterised by a deficiency of specialised cells.

Preferably, the therapeutic application is regeneration or repair. Optionally the regeneration or repair is of damaged organs, preferably the pancreas or the liver. Alternatively, the regeneration or repair may be of an organ which has not been 'damaged' as such but which has not developed in the normal way. 'Regeneration' should thus be interpreted broadly to include all methods of organ growth or improvement.

The treatment of diabetes is preferred, e.g. diabetes mellitus type I or type II. Other diseases which may conveniently be treated are obesity, particularly morbid obesity; fatty liver, particularly when associated with lipid and glycogen deposition; and any disorders characterised by or associated with a defect of glucose and/or insulin uptake and/or utilisation. Such disorders may be referred to as conditions associated with aberrant insulin production, uptake or utilisation.

Optionally, the present invention provides a short RNA of the invention and/or a specialised cell of the invention for use in the regeneration of at least part of the pancreas of a patient deficient in pancreatic cells, particularly beta-cells. Any patient whose pancreas does not produce sufficient insulin, or indeed any insulin, may benefit from such therapy. Insufficient insulin production includes the production of lower levels of insulin compared to a normal (healthy) subject, but it also includes subjects who produce insulin levels that are comparable to normal (healthy) subjects but who require higher insulin levels, for example due to insulin resistance, excessive food consumption, morbid obesity and the like.

Instead of, or in addition to, targeting the pancreas, the short RNA and/or cell of the invention may be used to target the liver, so that liver cells, or cells of the invention once they have populated the liver, produce insulin.

The short RNA molecules or cells may be administered via injection, e.g. intravenously, subcutaneously, intramuscular or into a target organ. Thus, injection may be systemic or at or into the target site, e.g. a target organ, preferably the pancreas or the liver. Alternatively, administration may be oral or pr (per rectum). Injection of a cell into the pancreas is preferred.

The short RNAs and/or cells of the invention may be administered to a patient in need thereof by any means or delivery vehicle known in the art, for example via nanoparticles, cationic lipids, lipids such as cholesterol or α-tocopherol, liposomes, e.g. positively charged cationic liposomes, polymers, such as polyethyleneimine, dendrimers, aptamers, or as antibody conjugates. The short RNAs may also be administered as viral vector expressed shRNAs or miRNA mimics.

Preferably, the saRNA or cell is associated, e.g. complexed with, linked to, or contained within, a moiety that targets the saRNA or cell to a specific tissue or cell type, e.g. pancreatic cells or liver cells, e.g. hepatocytes or beta cells. Said moiety may be one of the means/delivery vehicles mentioned above.

Aptamers are oligonucleotides or peptides with high selectivity, affinity and stability. They assume specific and stable three-dimensional shapes, thereby providing highly specific, tight binding to target molecules. For any specific molecular target, nucleic acid aptamers can be identified from combinatorial libraries of nucleic acids, e.g. by a technique called systematic evolution of ligands by exponential enrichment (SELEX) (see, for example, Tuerk C and Gold L: Systematic evolution of ligands by exponential enrichment: RNA ligands to bacteriophage T4 DNA polymerase. Science 1990, 249:505-510.). Peptide aptamers may be identified e.g. using a yeast two hybrid system. The skilled person is therefore able to design suitable aptamers for delivering the saRNAs or cells of the present invention to target cells such as liver or pancreatic cells, e.g. beta cells. DNA aptamers, RNA aptamers and peptide aptamers are contemplated. Administration of short RNAs of the invention to the pancreas using pancreas-specific aptamers is particularly preferred.

Also provided is a conjugate of an aptamer and an short RNA of the invention. The conjugate may be formed using any known method for linking two moieties, such as direct chemical bond formation, linkage via a linker such as streptavidin and so on.

Methods of generating antibodies against a target cell surface receptor are well known. The saRNA molecules of the invention may be attached to such antibodies, for example using RNA carrier proteins. The resulting complex may then be administered to a subject and taken up by the target cells via receptor-mediated endocytosis. The cells of the invention may be linked to such antibodies using known means.

The saRNA or cells may be encapsulated in liposomes using methods known in the art. The liposomes may optionally be associated with a target-cell specific moiety such as an antibody or a peptide.

As discussed above, the molecules of the present invention are generated based on sequence analysis of a target gene and methods and products associated with delivery of these short nucleic acid molecules are further aspects of the invention. Thus, the present invention also provides methods and products, including computer-readable storage media and data structures, which may be set out schematically in FIG. 9 and are discussed below with reference to FIG. 9. Unless otherwise stated, the definitions, description and preferred embodiments described above in relation to the methods and products of the present invention apply, mutatis mutandis, to the aspects discussed below.

Figure 9:
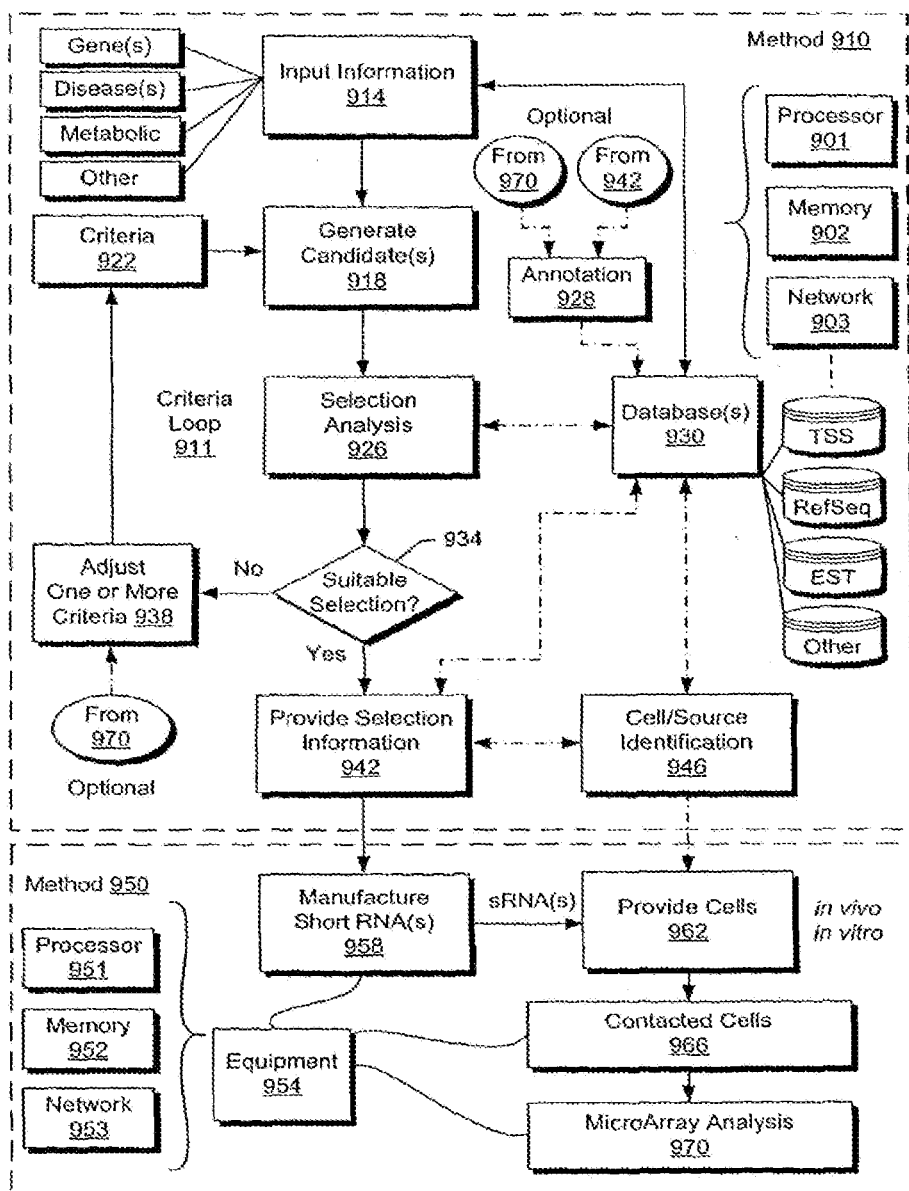

FIG. 9 shows an example of a method 910 that includes selecting information (e.g., as to a sequence for one or more short RNAs) and an example of a method 950 that includes manufacturing one or more short RNAs. The method 910 may include bioinformatic processes that may include computational processes that handle biomedical information and optionally other information. Such a method may include analyzing and managing biomedical information.

As shown in FIG. 9, the method 910 includes an input block 914 for input of information, which may include information for one or more genes, one or more diseases, one or more metabolites or metabolic pathways, or other information. A generation block 918 includes generating one or more candidate sequences based at least in part on the input information of the input block 914 and one or more criteria of a criteria block 922. A selection analysis block 926 includes analyzing the one or more generated sequences of the generation block 918. Such an analysis may include ranking candidates; noting that ranking may optionally occur automatically in the generation block 918, hence, in an example embodiment, the selection analysis block 926 may be optional, for example, implemented upon instruction of a configuration file, receipt of user input via a graphical user interface, etc.

As shown in the example of FIG. 9, the selection analysis block 926 may optionally interact with one or more databases, as represented by a database block 930 and some example databases, which include sequence databases such as a transcription start site (TSS) database, a reference sequence database (e.g., NCBI RefSeq, etc.), and an expressed sequence tags database (ETS) and optionally one or more other databases. Information retrieved from calls to one or more of such databases may be relied on by the selection analysis block 926.

As an example, where input information of the input block 914 is a gene, a TSS database may provide a TSS associated with that gene. In turn, one or more candidates generated by the generation block 918 may target an antisense sequence that is referenced with respect to the TSS (e.g., +/−500 nts). As a quality control or other measure, the selection analysis block 926 may perform an analysis that compares one or more generated candidates to other information, which may be retrieved from one or more databases. In this example, the selection analysis block 926 may optionally retrieve ESTs associated with the gene and compare such information to one or more generated candidates.

In another example, based on input information of the input block 914, an EST database may provide information associated with a gene for generation of one or more candidates by the generation block 918. In such an example, the selection analysis block 926 may optionally retrieve information from a TSS database and compare such information to one or more generated candidates as a quality control or other measure.

In yet another example, the input block 914 may retrieve information from a TSS database and an ETS database and the generation block 918 may generate one or more candidates based at least in part on such information. In such an example, the selection analysis block 926, if implemented, may, per the database block 930, optionally retrieve information from one or more databases for any of a variety of purposes. While various examples mention TSS or ETS databases, it is understood that a RefSeq database (e.g., NCBI RefSeq database) or other database may be accessed for retrieval of information, as appropriate.

Referring again to the method 910 and the selection analysis block 926, a decision block 934 may follow where, upon deciding that a suitable selection exists, the method 910 continues to a provision block 942 for providing selection information. Alternatively, or additionally, the decision block 934 may call upon an adjustment block 938 for adjusting one or more criteria, for example, to implement an optionally criteria loop 911. For example, where a number of generated candidates is large, where a quality measure is considered unacceptably low, etc., the loop 911 may include adjusting one or more criteria per the adjustment block 938 and providing such adjusted criteria to the criteria block 922 for input to the generation block 918.

As an example, consider a motif criterion that was not originally imposed by the generation block 918 being selected by the adjustment block 938 and communicated to the criteria block 922 in an effort to reduce the number of candidates to be generated by the generation block 918. As a specific example, consider a motif criterion for absence of aaaa, cccc, gggg, and uuuu in a RNA sequence. Based on number of candidates generated, a selection analysis, etc., the adjustment block 938 may loosen or impose such a criterion or optionally a portion thereof (e.g., absence of aaaa; absence of aaaa and cccc; absence of cccc; absence of gggg; etc.). While motifs are mentioned as examples of criteria, other criteria may include parameters of a GPBoost algorithm, GC content, Hamming distance, etc.

Referring to the method 910, where the provision block 942 provides information, such information may be relied on, as appropriate, for identification of cell or source information per an identification block 946, which may be configured to receive or access information in one or more of the databases 930. Consider an example embodiment where the method 910 need not necessarily know cell type a priori. While cell type may be a field in a database, generation of one or more candidates by the generation block 918 need not include a requirement that cell type be known. As an example, consider a cross-cell type investigation where all cell types demonstrating some correspondence to a selected candidate wish to be known. Accordingly, the method 910 may optionally be implemented, for example, to generate a database of candidates and corresponding cell types.

As to the provision block 942, it may provide selection information for more than one sequence to form a pool. A pool of sequences may provide for increased likelihood of a desired outcome or outcomes. The method 910 may optionally include a configuration option to provide a pool of sequences, as opposed to a single sequence. Further, the method 910 may include a configuration option to provide for double-stranded functionality where each strand of an RNA sequence is intended to have some effect. With respect to such options, the method 910 may enter the criteria loop 911 where one or more criteria are iteratively adjusted to provide for a proper size pool or at least one RNA sequence for double-stranded functionality. With respect to a learning process (e.g., including the loop 911), one or more relationships between pool size, double-stranded functionality, etc., may be established and relied on for setting initial criteria, for example, to reduce usage of computational resources (e.g., to reduce computation time, memory demands, etc.) for a subsequent implementation of the method 910.

With respect to a single sequence or a pool of sequences, the method 910 may provide selection information that includes, for each sequence, a corresponding likelihood of success indicator (e.g., probability, etc.). Such information may be considered to make decisions as to manufacture, prescribing administration of a treatment, administration of a treatment, etc. In an example embodiment that includes a programmable delivery device to deliver one or more short RNAs, a likelihood of success indicator may be considered to determine an amount of material to deliver, order of materials to deliver, frequency of material delivery, etc. For example, where such a device includes separate supplies for each sequence of a pool of sequences, if feedback indicates an inadequate response to one sequence, another sequence may be selected for delivery based at least in part on a success indicator. Accordingly, in an example embodiment, a data structure includes a sequence and a corresponding success indicator. Such a data structure may be stored in memory (e.g., a solid state memory device or other type of memory device).

More generally, the provision block 942 may provide a sequence with particular relevant information, whether such information stems from a candidate generation process, an analysis process, etc. As an example, consider a source, a service or other information relevant to manufacture of a sequence. Such information may be uncovered via access to a database, parsing information in the database and optionally searching the Internet based on the parsed information. For example, consider accessing the National Center for Biotechnology Information (NCBI) Reference Sequence (RefSeq) database, parsing information in the database for listed publications (e.g., as associated with an entry) and then searching the Internet using the parsed information (e.g., name, journal, affiliation, disease, etc.).

In an example embodiment, the method 910 provides one or more sequences stored to memory in association with other information, for example, germane to a source for at least one sequence (e.g., service, manufacturer, etc.), a type of cell suitable for contacting, a metabolic pathway or pathways associated with at least one sequence, a known side-effect of a hormone concentration in a metabolic pathway (e.g., which may be caused by up or down regulation associated with a short RNA), a known clearance rate for material delivered an organism (e.g., IV, direct to organ, etc.), etc. Such an optional method may be referred to as a co-discovery method, which can provide more than simply a sequence or sequences. Co-discovery can expedite decision making as to one or more downstream processes that may ultimately lead to treatment of an organism and potentially conserve resources (e.g., time, money, limited supplies, test organisms, etc.). Such co-discovery can be synergistic and lead to more successful and economical outcomes.

The method 950 of FIG. 9 may be implemented using one or more types of equipment 954 (e.g., RNA manufacture equipment, cell maintenance equipment, etc.). Such equipment may include one or more processors, ASICs, etc., for operational control. Such equipment may include memory for storage of information such as instructions for operational control. Such equipment may include one or more network interfaces, for example, for purposes of communication, data access, etc.

As shown, the method 950 includes a manufacture block 958 that may receive selection information as provided by the provision block 942. The provision block 942 may provide selection information in a digital form and optionally store such information to memory (e.g., a hard drive, solid-state memory, etc.), communicate such information via an interface (e.g., a network interface), etc. Accordingly, the manufacture block 958 may include receiving data from a data storage or receiving data communicated via wire or wirelessly (e.g., via a wireless network). The method 950 further includes a provision block 962 for providing cells, which may optionally rely on information from the identification block 946. As shown, the method 950 can include contacting short RNAs and cells to provide contacted cells per the contacted cells block 966. An analysis block 970 may perform one or more microarray analyses or other analyses on such cells, fluids, etc. For example, where the contacted cells are in an organism, samples may be taken from the organism and analyzed.

Referring again to the method 910, output information from the analysis block 970 may optionally serve as input information to the adjustment block 938 or to an annotation block 928. As to the annotation block 928, this block may receive selection information from the selection block 942, analysis information from the analysis block 970 or other information for purposes of annotating one or more of the databases 930. As an example, consider the National Center for Biotechnology Information (NCBI) Reference Sequence (RefSeq) database, which includes a collection of taxonomically diverse, non-redundant and richly annotated sequences representing naturally occurring molecules of DNA, RNA, and protein. In an example embodiment, the method 910 can include annotating one or more fields in the RefSeq database based on information such as selection information and analysis information. Such annotations may include private annotations (e.g., in a private copy of the RefSeq database) or public annotations (e.g., in a public copy of the RefSeq database).

With respect to the RefSeq database, an entry can include diverse types of information, including quantitative and qualitative information. As examples, an entry may include fields for publications, description of a gene, description of a gene's transcript variants, etc. In an example embodiment, the selection analysis block 926 may access such information, whether qualitative or quantitative, for purposes of performing a selection analysis. As an example, consider generation of a candidate sequence, accessing publication information associated with an entry in the RefSeq database and searching publications associated with the publication information for the candidate sequence, or a portion thereof. Such an approach may readily ascertain whether a candidate has been previously generated, uncovered, etc., and possibly whether any modicum of success was demonstrated for any particular purpose. In an example embodiment, the method 910 may include a notification block that issues a notification when such information is found. Such information may be communicated and presented for review via a graphical user interface (e.g., visually via a monitor) or other type of user interface (e.g., audio via a speaker) to one or more persons (e.g., via email, text message, etc.), which may, in turn, instruct the method 910 to take particular action such as to dismiss candidate, to accept candidate, to generate more like this candidate, etc.

In the examples of FIG. 9, the methods 910 and 950 are shown along with processors 901, 951, memory 902, 952 and networks 903, 953. The various method blocks may optionally include processor-executable instructions executable by one or more processors (e.g., cores) such as the processors 901 and 951. Such instructions may optionally be stored on one or more processor or computer-readable media, which may be storage media (e.g., consider physical storage media). In an example embodiment, multiple processors may be provided for execution of instructions in any of a variety of manners. Parallel or other types of architectures may be implemented for speed or another purpose.

The method 910 may optionally operate according to an input file that includes information for a series of genes, diseases, metabolites, etc. Accordingly, the method 910 may execute for long periods of time where any selection information may be output to a storage device (e.g., as a library, database, file, etc.). Such an execution process may implement learning processes that hone criteria, associate criteria with information, etc. For example, given input information associated with a hormone, criteria may be honed upon generating candidates favorable for up-regulation of that hormone. As another example, consider generating candidates, uncovering information about such candidates, directly or indirectly via one or more databases, and then analyzing the uncovered information for associations. Such associations may provide for honing one or more criteria, for example, where candidates demonstrate absence of features that were not explicitly set forth. For example, where candidates demonstrate absence of a motif, a corresponding criterion may be implemented that acts to conserve computational resources for subsequent candidate generation.

In an example embodiment, a method can include providing genetic information; providing criteria for short RNA sequences; generating candidate short RNA sequences based on the genetic information and the criteria using a computer; selecting one or more of the sequences; and writing the selected one or more sequences to memory. Such a method may include communicating the selected one or more sequences via a network. For example, where a service or equipment can manufacture sequences, the one or more selected sequences may be communicated to the service (e.g., via the Internet) or to the equipment (e.g., via a network interface). In such a method, the providing genetic information may include providing genetic information associated with hormone regulation. Further such a method may include accessing data stored in a sequence database; analyzing candidate short RNA sequences and the accessed data to output match information; adjusting one or more of the criteria based on the match information and repeating at least the generating to generate additional candidate short RNA sequences and the analyzing to output revised match information; and, based on the revised match information, writing to memory one or more of the additional candidate short RNA sequences. In turn, a method can include reading from memory, one of the one or more additional candidate short RNA sequences to manufacture a short RNA based on the one short RNA sequence. Further, a method can include manufacturing a short RNA based on one of the one or more additional short RNA sequences and contacting the short RNA with a cell of the cell type. As to the criteria, such criteria may include a sequence motif criterion and adjusting may adjust a sequence motif criterion.

In an example embodiment, a manufactured short RNA can include a sequence determined by a computerized process where the sequence conforms to one or more predefined criteria automatically adjusted by the computerized process based at least in part on genetic information related to hormone regulation and data stored in a sequence database, and where the computerized process adjusts the one or more criteria based in part on a model for induction of cleavage of a target RNA transcript. Such a manufactured short RNA may rely on a process that includes a predefined sequence motif criterion, for example, a sequence motif criterion selected from one of aaaa, cccc, gggg, and uuuu. As to the target RNA transcript, such a transcript may be based on data stored in a sequence database.

In an example embodiment, one or more computer-readable storage media can include processor-executable instructions to instruct a computing system to: select a short nucleic acid sequence from a group of short nucleic acid sequences based at least in part on a genetic programming and boosting technique based efficacy predictor for each short nucleic acid sequence germane to regulation of an insulin associated gene; and output a data structure to a computer-readable storage medium where the data structure includes sequence information for the selected short nucleic acid sequence and where the selected short nucleic acid sequence includes a short nucleic acid sequence selected from a group of, for example, a short nucleic acid sequence configured to activate PDX1 expression, a short nucleic acid sequence configured to activate Neurogenin3 expression, a short nucleic acid sequence configured to activate Rfx6 expression, and a short nucleic acid sequence configured to activate MafA expression. In such an example, instructions may be included to select based at least in part on absence of at least one sequence motif, on GC content or on a Hamming distance.

As mentioned, various algorithms may include efficacy information, such as a score, efficacy indicator, efficacy predictor, etc. In an example embodiment, sequence information can include efficacy predictor information. In such an example, instructions may be provided to instruct a computing system to read a data structure output to a computer-readable storage medium and to instruct a machine (e.g., equipment), based at least in part on the sequence information, for example, to manufacture or deliver at least one short nucleic acid. As an example, consider a data structure with a sequence and associated efficacy predictor. In such an example, the efficacy predictor may be read and relied upon by a machine to make decisions as to order of manufacture, order of delivery, etc., especially when the efficacy predictor may be compared to or ranked with respect to one or more other efficacy predictors. Further, in an example embodiment, information may optionally be encrypted. For example, to reduce risk of exposing a sequence, a sequence may be embodied in a storage medium in an encrypted form, which, in turn, may be de-encrypted by an authorized machine (e.g., a machine having a security key). Where transmission may occur, a secure connection may be established and alternatively, or additionally, at least a portion of a sequence may be encrypted. Accordingly, where a sequence or sequences, and possibly accompanying information, may be valuable and proprietary, security techniques such as encryption may be implemented.

In an example embodiment, a data structure embodied in a computer-readable storage medium may be configured to instruct a machine (e.g., equipment) to manufacture or deliver a short nucleic acid sequence. Such a data structure may include sequence information for a short nucleic acid sequence selected from a group, for example, such as a group that includes a short nucleic acid sequence configured to activate PDX1 expression, a short nucleic acid sequence configured to activate Neurogenin3 expression, a short nucleic acid sequence configured to activate Rfx6 expression, and a short nucleic acid sequence configured to activate MafA expression. In such an example embodiment, sequence information may include a genetic programming and boosting technique based efficacy predictor for one or more short nucleic acid sequences (e.g., where each efficacy predictor is germane to regulation of an insulin associated gene, etc.). In various examples, a data structure may include sequence information for multiple short nucleic acid sequences and a corresponding efficacy predictor for each of the multiple short nucleic acid sequences. Or, alternatively, a computer-readable medium may include multiple data structures (e.g., each including sequence information, which may optionally include efficacy information).

Oligonucleotide synthesis includes chemical synthesis of relatively short fragments of nucleic acids with defined chemical structure. Building blocks may be sequentially coupled to form an oligonucleotide chain in an order required by a provided sequence. Oligonucleotide synthesis may be carried out automatically using computerized equipment (e.g., solid-phase oligonucleotide synthesizers that include column, multi-well plate, array or other formats). Examples of commercially available synthesizers include the OligoPilot™ series synthesizers and OligoProcess™ series synthesizers (GE Healthcare, Uppsala, Sweden). Such synthesizers may include or operate in conjunction with, for example, ÄKTA™ systems and UNICORN™ control software (GE Healthcare, Uppsala, Sweden).

In an example embodiment, a computing system for synthesizer control is provided that executes instructions (e.g., embodied on a computer-readable medium) for sequence input, sequence editing, security, manufacture of one or more sequences, audit trail, etc. In this example embodiment, a data structure can include at least one sequence field and, for each sequence field, a corresponding efficacy predictor field where the data structure may be provided via a storage medium, a wired interface or a wireless interface. In this example embodiment, the computing system may access data (e.g., information) in the data structure to synthesize one or more oligonucleotides. Where desired, instructions for control of a synthesizer may optionally access one or more efficacy predictors and control the synthesizer based at least in part on such information (e.g., via automatic data discovery, user selected option, etc.). For example, a highest predicted efficacy sequence may be scheduled for synthesis (or other processing such as purification, etc.) before a lower predicted efficacy sequence. As to a sequence in a sequence field of a data structure, a short nucleic acid sequence may include, for example, a string of informational monikers "CUCAUG". These informational monikers can function, on a moniker-by-moniker basis, to instruct the synthesizer to synthesize an oligonucleotide (e.g., via a series of chemical bonding actions) where, for example, each nucleotide includes a base attached to a ribose where the bases are ordered according to the informational monikers as follows: cytosine (C), uracil (U), cytosine (C), adenine (A), uracil (U) and guanine (G). Further, while each moniker has a function, so does the number of monikers. Further, where multiple sequences are provided, the number of sequences can be functional (e.g., a total number of sequences to instruct a synthesizer to make). In an example embodiment, by accessing a data structure, a computing system can control a synthesizer to manufacture (e.g., to output) one or more oligonucleotides (e.g. short nucleic acids such as short RNA). In such an example, the computing system (e.g., processor, memory, interfaces, etc.) may recognize sequences of monikers (e.g., read from memory or otherwise received) and thereafter cause one or more series of nucleotides to be synthesized. Where, for example, additional information accompanies each sequence of monikers, a functional interrelationship among the sequences may exist and a computing process may be performed utilizing such additional information (e.g., efficacy predictors, off-target risk indicator, probability of success, etc.) to order synthesis, etc.

In another aspect, the present invention provides one or more computer-readable storage media comprising processor-executable instructions to instruct a computing system to: select a short nucleic acid sequence from a group of short nucleic acid sequences based at least in part on a genetic programming and boosting technique based efficacy predictor for each short nucleic acid sequence germane to regulation of an insulin associated gene; and output a data structure to a computer-readable storage medium wherein the data structure comprises sequence information for the selected short nucleic acid sequence and wherein the selected short nucleic acid sequence comprises a short nucleic acid sequence selected from a group comprising or consisting of a short nucleic acid sequence configured to activate MafA expression, a short nucleic acid sequence configured to activate PDX1 expression, a short nucleic acid sequence configured to activate Neurogenin3 expression, a short nucleic acid sequence configured to activate Rfx6 expression, a short nucleic acid sequence configured to activate insulin expression and a short nucleic acid sequence configured to activate NeuroD expression.

Preferably, the instructions to select the short nucleic acid sequence comprise instructions to select based at least in part on absence of at least one sequence motif, on GC content or on a Hamming distance.

Preferably, the sequence information comprises efficacy predictor information and further comprising processor-executable instructions to instruct a computing system to read the data structure output to the computer-readable storage medium and to instruct a machine, based at least in part on the sequence information, to manufacture or deliver at least one short nucleic acid.

Thus, in a further aspect, there is provided a data structure embodied in a computer-readable storage medium to instruct a machine to manufacture or deliver a short nucleic acid sequence, the data structure comprising sequence information for a short nucleic acid sequence selected from a group comprising or consisting of a short nucleic acid sequence configured to activate MafA expression, a short nucleic acid sequence configured to activate PDX1 expression, a short nucleic acid sequence configured to activate Neurogenin3 expression, a short nucleic acid sequence configured to activate Rfx6 expression, a short nucleic acid sequence configured to activate insulin expression and a short nucleic acid sequence configured to activate NeuroD expression.

Preferably, the sequence information further comprises a genetic programming and boosting technique based efficacy predictor for the short nucleic acid sequence germane to regulation of an insulin associated gene.

Preferably, the data structure further comprises sequence information for multiple short nucleic acid sequences and a corresponding efficacy predictor for each of the multiple short nucleic acid sequences.

Various documents including, for example, publications and patents, are recited throughout this disclosure. All such documents are, in relevant part, hereby incorporated by reference. The citation of any given document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Referenced herein are trade names for components including various ingredients utilized in the present invention. The inventor herein does not intend to be limited by materials under a certain trade name. Equivalent materials (e.g., those obtained from a different source under a different name or reference number) to those referenced by trade name may be substituted and utilized in the descriptions herein.

It is specifically intended that the above-disclosed optional and preferred features and embodiments of the present invention may be taken alone or together in any number and in any combination, apart from where features or embodiments are mutually exclusive, where it would be impossible to do so or where doing so would be contrary to the aims of the present invention.

BRIEF DESCRIPTION OF TABLES AND DRAWINGS

The following examples are intended to be illustrative of the present invention and to teach one of ordinary skill in the art to make and use the invention. These examples are not intended to limit the invention in any way. The invention will now be further described in the following Examples and the Tables and Figures in which:

Table 1 shows short RNA molecules designed for activating PDX1 expression. Antisense (guide) sequences are shown on the right, sense (passenger) sequences are shown on the left. RNA sequences contain uracil (U) in place of thymine (T), and these two residues are equivalent in the sequences provided in the Tables.

Table 2 shows short RNA molecules designed for activating Neurogenin expression. Antisense (guide) sequences are shown on the right, sense (passenger) sequences are shown on the left.

Table 3 shows short RNA molecules designed for activating Rfx6 expression. Antisense (guide) sequences are shown on the right, sense (passenger) sequences are shown on the left.

Table 4 shows short RNA molecules designed for activating MafA expression. Antisense (guide) sequences are shown on the right, sense (passenger) sequences are shown on the left.

Table 5 shows short RNA molecules designed for activating insulin expression. Antisense (guide) sequences are shown on the right, sense (passenger) sequences are shown on the left.

Table 6 shows short RNA molecules designed for activating insulin expression.

Table 7 Shows sequences which the short RNAs of the present invention may comprise or consist of. When the short RNA is single-stranded, it preferably comprises or consists of a sequence listed in the antisense column. Double stranded short RNAs are formed of a strand comprising or consisting of a sequence shown in the sense column paired with a strand comprising or consisting of a sequence shown in the same row in the antisense column. In other words, each row of Table 7 shows which sequences may be paired to form a double-stranded RNA. Thus, a double stranded short RNA may comprise SEQ ID NO: 1 and SEQ ID NO: 45; or SEQ ID NO: 5 and SEQ ID NO:49; or SEQ ID NO: 6 and SEQ ID NO: 50 and so on. Table 7 includes all of the sense and antisense sequences of Tables 1-6.

FIG. 1 is a schematic diagram showing the PDX1 locus and potential antisense target candidates. The Figure shows the genomic location of PDX1, the structure of the PDX1 transcript, and spliced ESTs from the surrounding regions (image adapted from the UCSC genome browser). Box outlines the PDX1 promoter region and the closest antisense EST upstream of PDX1 (CR593175). The EST initiates 1.4 kb and terminates 90 kb from PDX1's transcription start site (TSS). Note that the EST is transcribed through and overlaps PDX1's TSS. Arrows indicate potential target sites for small RNA candidates.

Figure 2:
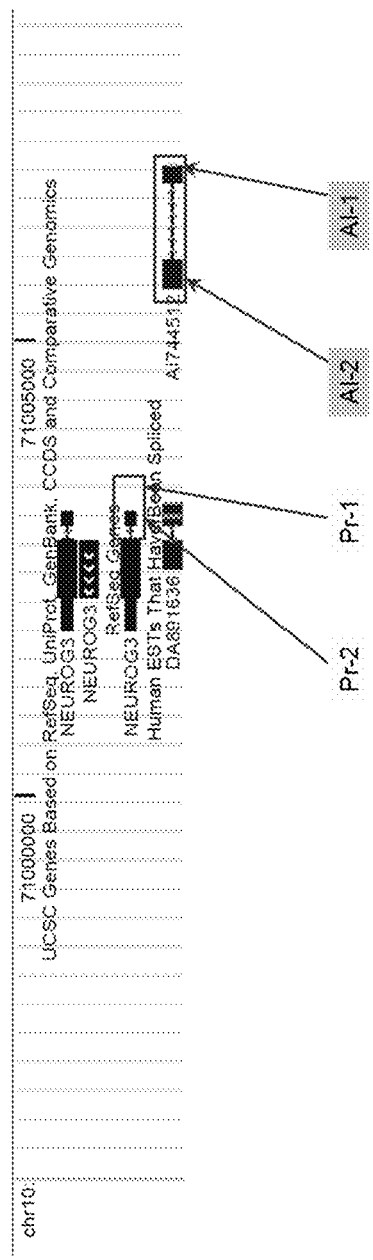

FIG. 2 is a schematic diagram showing the Ngn3 locus and potential antisense target candidates. The figure shows the genomic location of Ngn3, the structure of the Ngn3 transcript, and spliced ESTs from the surrounding regions (image from the UCSC genome browser). Boxes outline the Ngn3 promoter region and the closest antisense transcript upstream of Ngn3 (Al744512). The EST initiates 2.4 kb and terminates 3.7 kb from Ngn3's TSS. Arrows indicate potential target sites for small RNA candidates.

Figure 3:
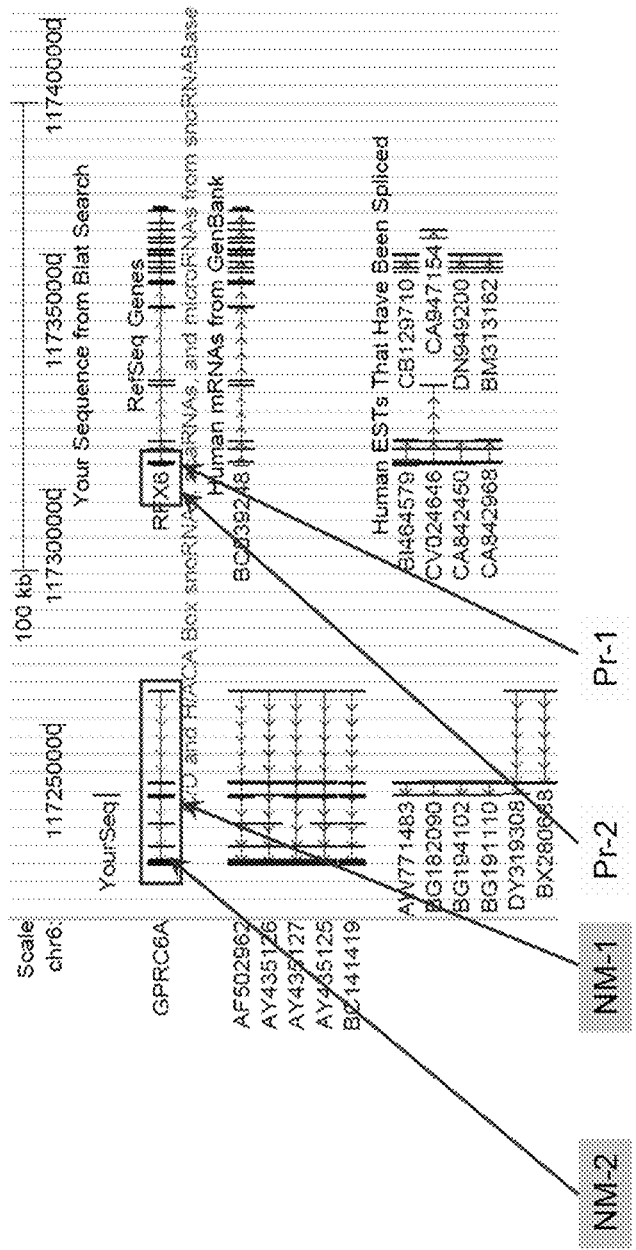

FIG. 3 is a schematic diagram showing the Rfx6 locus and potential antisense target candidates. The figure shows the genomic location of Rfx6, the structure of the Rfx6 transcript, and spliced ESTs from the surrounding regions (image from the UCSC genome browser). Boxes outline the Rfx6 promoter region and a close antisense transcript upstream of Rfx6. The EST is called GPRC6A and it initiates 48 kb and terminates 85 kb from Rfx6's TSS. Arrows indicate potential target sites for small RNA candidates.

Figure 4:
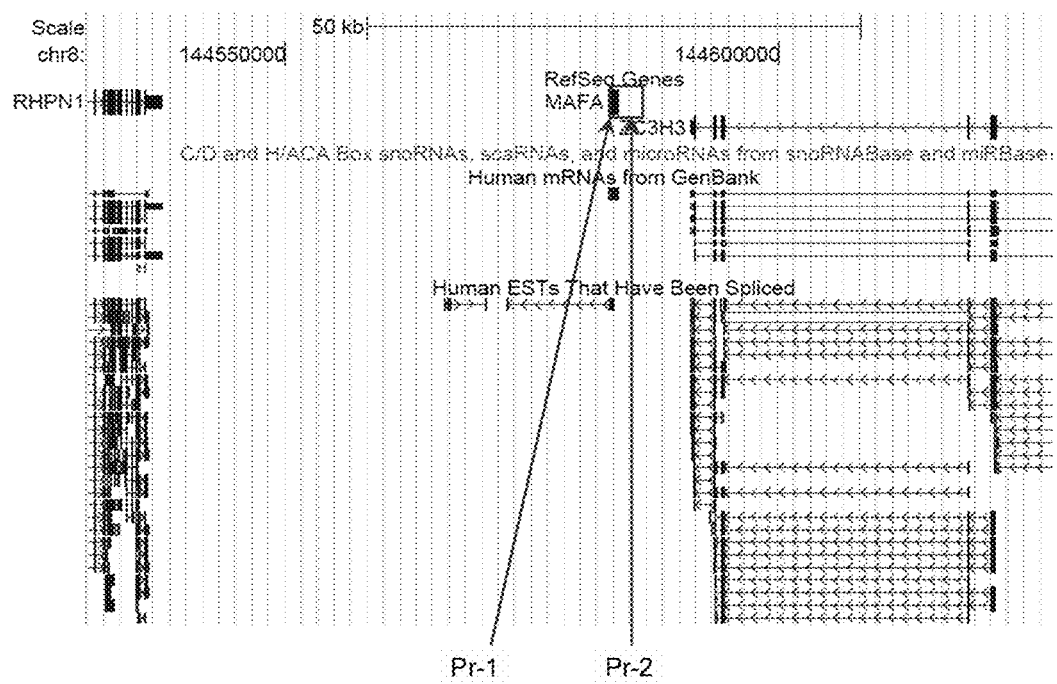

FIG. 4 is a schematic diagram showing the MafA locus and potential antisense target candidates. The figure shows the genomic location of MafA, the structure of the MafA transcript, and spliced ESTs from the surrounding regions (image from the UCSC genome browser). Arrows indicate potential target sites for small RNA candidates.

Figure 5:
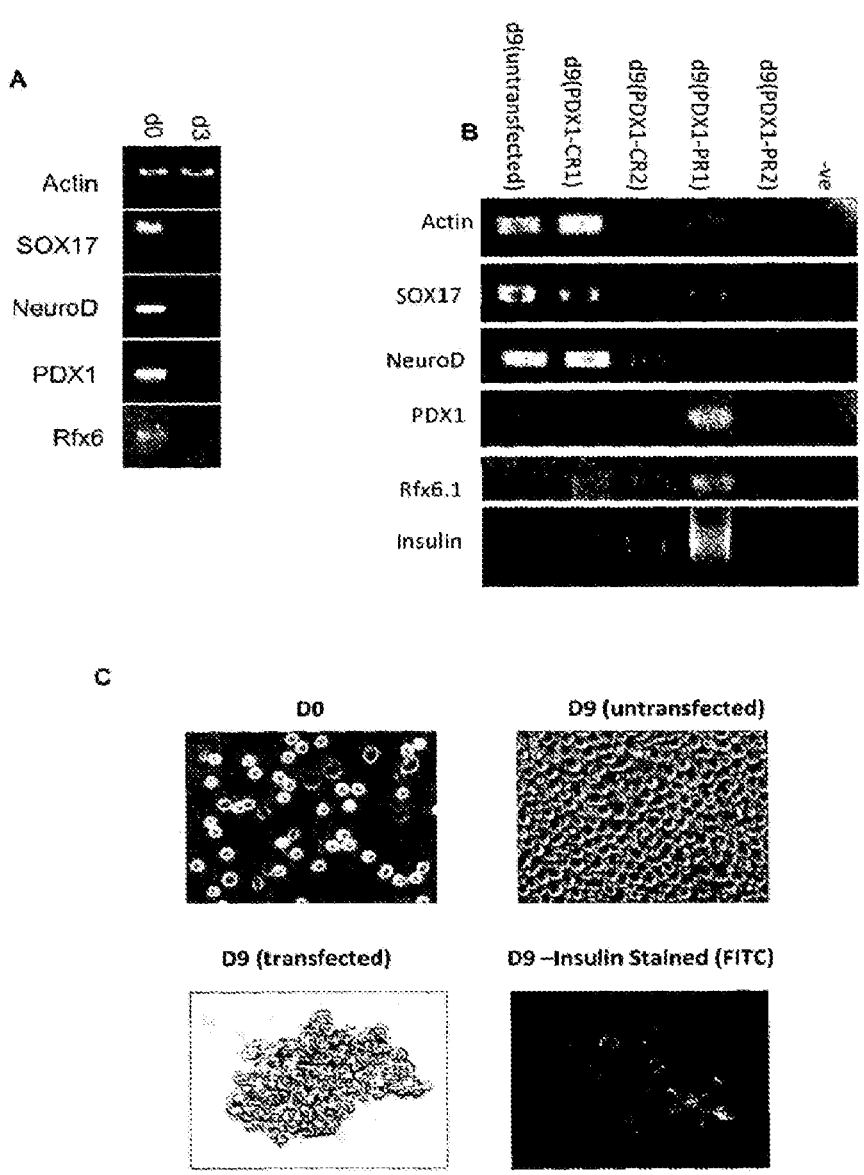

FIG. 5 A. Photograph of a gel showing RNA. Total RNA isolated from freshly isolated omnicytes (day 0) and the cells after 3 days of culture (day 3) were reverse transcribed for mRNA screening. Actin RNA expression was measured as a control. Day 0 cells express mesodermal markers such as SOX17, but these cells also express transcription factors NeuroD, PDX1 and Rfx6 required for specialisation into insulin producing β-cells. Day 3 results show that these factors are downregulated within the first three days of expansion.

B. Photograph of a gel showing RNA. Omnicytes were cultured for 3 days and then transfected with saRNA targeting PDX1. Four possible sets of anneal oligonucleotides (CR1, CR2, PR1 and PR2) were tested. After 9 days (d9) RNA was assayed. CR2 and PR1 enhanced expression of PDX1, Rfx6 and Insulin at day 9.

C. The cells transfected with PDX1 (CR2 and PR1) at day 9 displayed morphological changes reminiscent of islet cell cluster formation. Fluorescent staining using Alexa-488 conjugated secondary antibody against insulin primary antibody demonstrated that these cell cluster expressed insulin. Secondary antibody alone staining did not show auto fluorescence or unspecific binding (data not shown).

Figure 6:
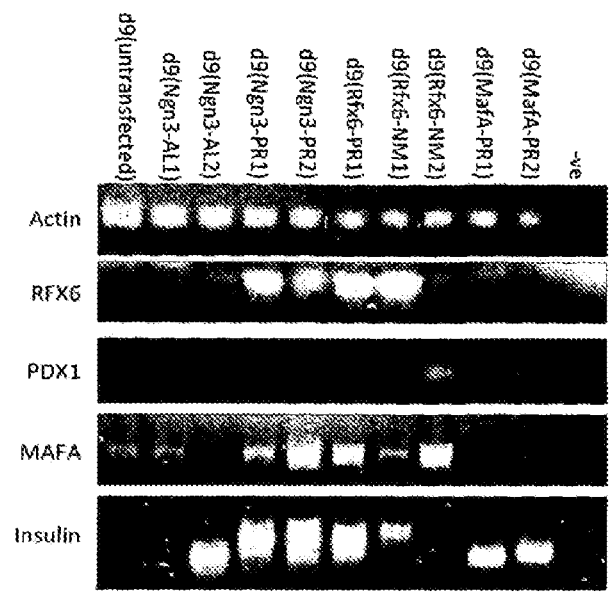
Figure 6:
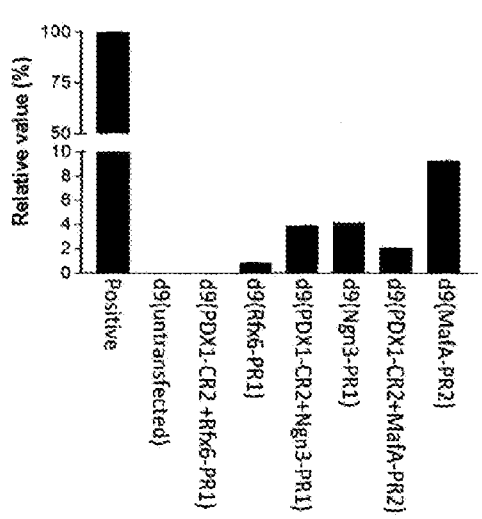

FIG. 6 A. Photograph of a gel showing RNA. Transient transfection of annealed saRNA oligonucleotides targeting transcription factors involved in late stage specialisation of islet cells were carried out at day 3 and day 6 of culture. Neurogenin 3 (AL2), MafA (PR1 and PR2) upregulated expression of pro-insulin whilst Neurogenin 3 (PR1 and PR2), Rfx6 (PR1 and NM1) upregulated expression of pre pro-insulin.

B. Insulin expression following exposure with a glucose gradient was assayed. Cells were transiently transfected with a combination of saRNA oligonucleotides. Rfx6 (PR1), Ngn3 (PR1) and MafA (PR2) were transfected alone or with PDX1 (CR2) at day 3 and day 6 of culture. Cells were pre-treated with αMEM supplemented with 10 mM nicotinamide, 50 ng IGF-II, 10 ng HGF, 25 ng exendin-4 and 10 ng activin A at day 9 for 16 hours followed by addition of 2.8 mM of glucose for 3 hours and 20 mM of glucose for a further 3 hours. The culture media was isolated and processed for a pro insulin ELISA. Results represent percentage relative to a positive control as provided by the kit (7.9 pM of insulin).

FIG. 7 Flow chart illustrating the induction of insulin-producing cells.

Figure 8:
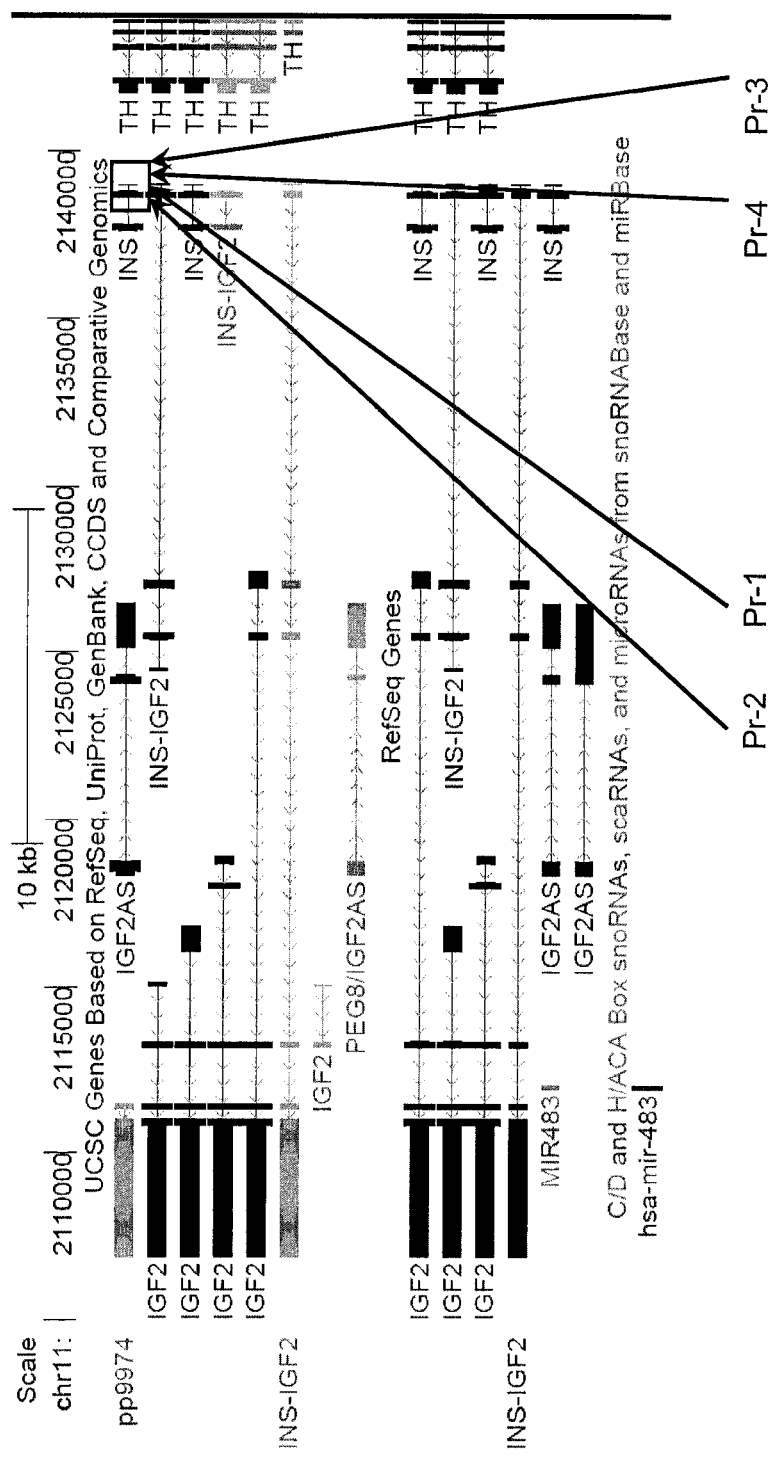

FIG. 8 is a schematic diagram showing the (pro)insulin locus and potential antisense target candidates. The Figure shows the genomic location of (pro)insulin, the structure of the (pro)insulin transcript, and spliced ESTs from the surrounding regions (image adapted from the UCSC genome browser). Box outlines the (pro)insulin promoter region. Arrows indicate potential target sites for small RNA candidates.

FIG. 9 Flow diagram showing a method of selecting information and an example of a method that includes manufacturing one or more short RNAs.

Figure 10:
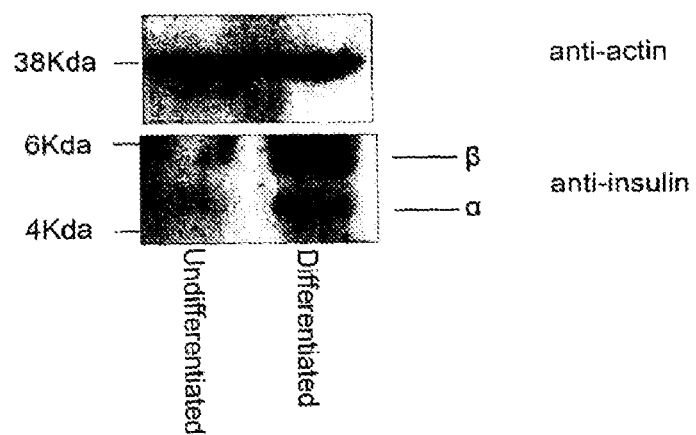

FIG. 10 Western blot of actin and insulin expression of untreated cells (control) and of saRNA treated cells.

Figure 11:
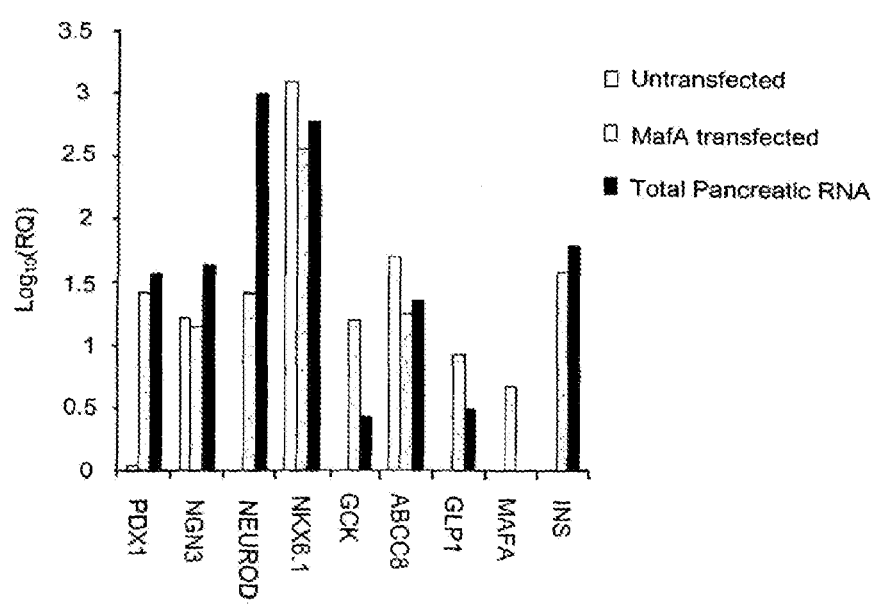

FIG. 11 Graph of quantitative PCR of key transcription factors involved in beta-cell development. Quantitative PCR was carried out on untransfected (control) cells, cells transfected with saRNA which up-regulates MafA expression, and total normal pancreatic RNA.

Figure 12:
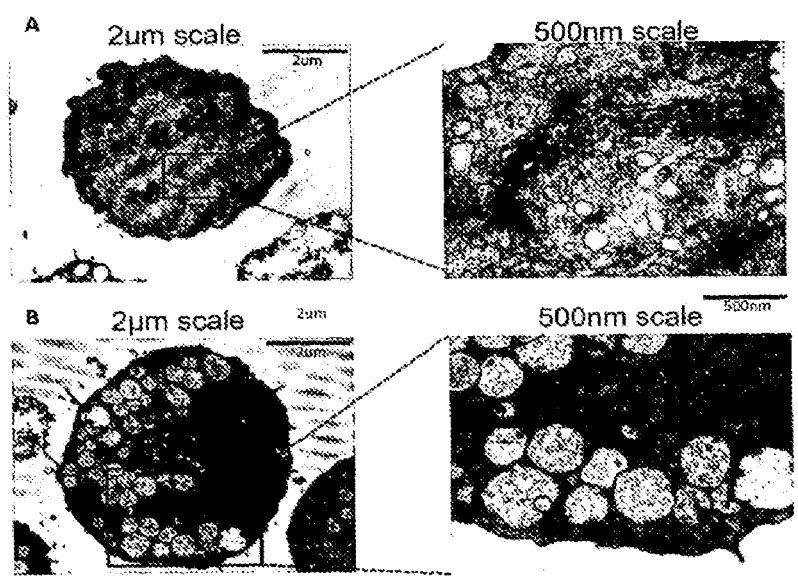

FIG. 12 Electron microscopy image of transfected and untransfected cells (see Example 7)

Figure 13:
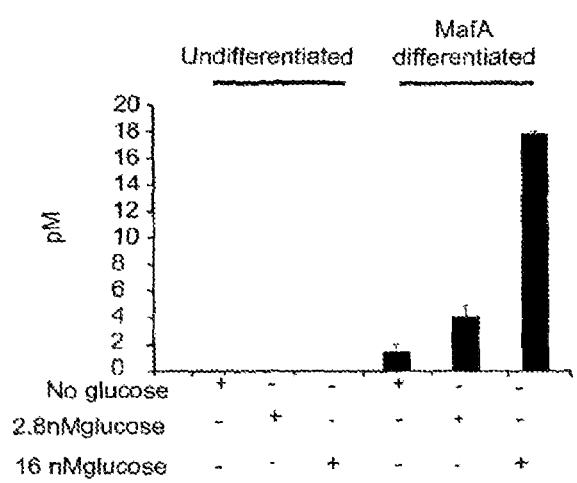
Figure 13:
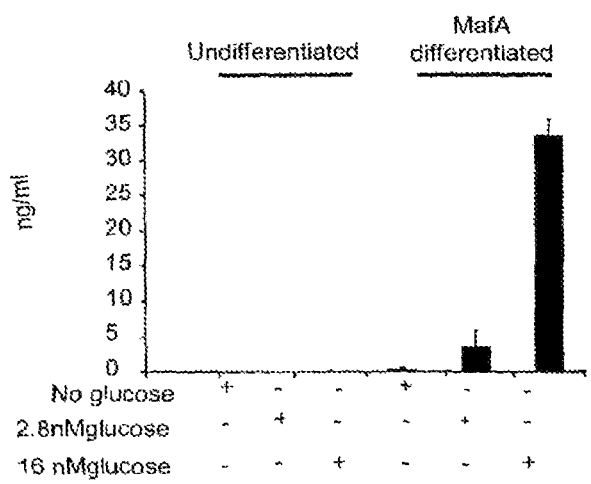

FIG. 13 Graph showing results of ELISA of Insulin and C-peptide

FIG. 14 Flow chart illustrating an optimised protocol for the induction of insulin-producing cells. PSG stands for pencillin, streptomycin and glutamine.

Figure 15:
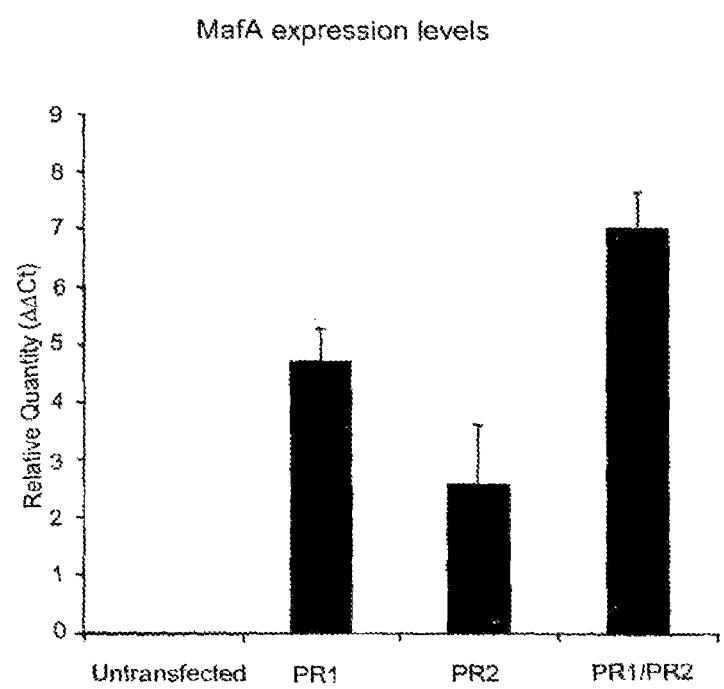

FIG. 15 Graph which shows relative quantitation of MafA in transfected liver epithelial cells relative to untransfected cells and normalised to Actin. Cells were seeded in charcoal stripped phenol red free RPMI for synchronisation. After 16 hours the cells were transfected with saRNA targeted for MafA (PR1, PR2 and a combination of both).

REFERENCES

1. Guz Y, Nasir I, & Teitelman G (2001) Regeneration of pancreatic beta cells from intra-islet precursor cells in an experimental model of diabetes *Endocrinology* 142, 4956-4968.

2. Shapiro A M, Lakey J R, Ryan E A, Korbutt G S, Toth E, Warnock G L, Kneteman N M, & Rajotte R V (2000) Islet transplantation in seven patients with type 1 diabetes mellitus using a glucocorticoid-free immunosuppressive regimen *N Engl J Med* 343, 230-238.
3. Bonner-Weir S, Taneja M, Weir G C, Tatarkiewicz K, Song K H, Sharma A, & O'Neil J J (2000) In vitro cultivation of human islets from expanded ductal tissue *Proc Natl Acad Sci USA* 97, 7999-8004.
4. Halvorsen T & Levine F (2001) Diabetes mellitus-cell transplantation and gene therapy approaches *Curr Mol Med* 1, 273-286.
5. Petersen B E, Bowen W C, Patrene K D, Mars W M, Sullivan A K, Murase N, Boggs S S, Greenberger J S, & Goff J P (1999) Bone marrow as a potential source of hepatic oval cells *Science* 284, 1168-1170.
6. Theise N D, Badve S, Saxena R, Henegariu O, Sell S, Crawford J M, & Krause D S (2000) Derivation of hepatocytes from bone marrow cells in mice after radiation-induced myeloablation *Hepatology* 31, 235-240.
7. Oh S H, Miyazaki M, Kouchi H, Inoue Y, Sakaguchi M, Tsuji T, Shima N, Higashio K, & Namba M (2000) Hepatocyte growth factor induces differentiation of adult rat bone marrow cells into a hepatocyte lineage in vitro *Biochem Biophys Res Commun* 279, 500-504.
8. Gordon M Y, Riley G P, & Greaves M F (1987) Plastic-adherent progenitor cells in human bone marrow *Exp Hematol* 15, 772-778.
9. Gordon M Y (1994) Plastic-adherent cells in human bone marrow generate long-term hematopoiesis in vitro *Leukemia* 8, 865-870.
10. Hellerstrom C (1984) The life story of the pancreatic B cell *Diabetologia* 26, 393-400.
11. Rosenberg L & Vinik A I (1992) Trophic stimulation of the ductular-islet cell axis: a new approach to the treatment of diabetes *Adv Exp Med Biol* 321, 95-104; discussion 105-109.
12. Swenne I (1992) Pancreatic beta-cell growth and diabetes mellitus *Diabetologia* 35, 193-201.
13. Zaret K S (2008) Genetic programming of liver and pancreas progenitors: lessons for stem-cell differentiation *Nat Rev Genet* 9, 329-340.
14. Jonsson J, Carlsson L, Edlund T, & Edlund H (1994) Insulin-promoter-factor 1 is required for pancreas development in mice *Nature* 371, 606-609.
15. Guz Y, Montminy M R, Stein R, Leonard J, Gamer L W, Wright C V, & Teitelman G (1995) Expression of murine STF-1, a putative insulin gene transcription factor, in beta cells of pancreas, duodenal epithelium and pancreatic exocrine and endocrine progenitors during ontogeny *Development* 121, 11-18.
16. Offield M F, Jetton T L, Labosky P A, Ray M, Stein R W, Magnuson M A, Hogan B L, & Wright C V (1996) PDX-1 is required for pancreatic outgrowth and differentiation of the rostral duodenum *Development* 122, 983-995.
17. Ahlgren U, Jonsson J, & Edlund H (1996) The morphogenesis of the pancreatic mesenchyme is uncoupled from that of the pancreatic epithelium in IPF1/PDX1-deficient mice *Development* 122, 1409-1416.
18. Ahlgren U, Pfaff S L, Jessell T M, Edlund T, & Edlund H (1997) Independent requirement for ISL1 in formation of pancreatic mesenchyme and islet cells *Nature* 385, 257-260.
19. Gradwohl G, Dierich A, LeMeur M, & Guillemot F (2000) neurogenin3 is required for the development of the four endocrine cell lineages of the pancreas *Proc Natl Acad Sci USA* 97, 1607-1611.
20. Murtaugh L C (2007) Pancreas and beta-cell development: from the actual to the possible *Development* 134, 427-438.
21. Smith S B, Qu H Q, Taleb N, Kishimoto N Y, Scheel D W, Lu Y, Patch A M, Grabs R, Wang J, Lynn F C, et al. Rfx6 directs islet formation and insulin production in mice and humans *Nature* 463, 775-780.
22. Gordon M Y, Levicar N, Pai M, Bachellier P, Dimarakis I, Al-Allaf F, M'Hamdi H, Thalji T, Welsh J P, Marley S B, et al. (2006) Characterization and clinical application of human CD34+ stem/progenitor cell populations mobilized into the blood by granulocyte colony-stimulating factor *Stem Cells* 24, 1822-1830.
23. Li L C, Okino S T, Zhao H, Pookot D, Place R F, Urakami S, Enokida H, & Dahiya R (2006) Small dsRNAs induce transcriptional activation in human cells *Proc Natl Acad Sci USA* 103, 17337-17342.
24. Janowski B A, Younger S T, Hardy D B, Ram R, Huffman K E, & Corey D R (2007) Activating gene expression in mammalian cells with promoter-targeted duplex RNAs *Nat Chem Biol* 3, 166-173.
25. Huang V, Qin Y, Wang J, Wang X, Place R F, Lin G, Lue T F, & Li L C RNAa is conserved in mammalian cells *PLoS One* 5, e8848.

EXAMPLES

Example 1

Designing Short RNAs for Activating PDX1 Expression

The saRNA design was carried out using the method described above. More specifical details are provided below.

PDX1 is located on chromosome 13 (see FIG. 1), band q12.2. The full gene name of PDX1 is "*Homo sapiens* pancreatic and duodenal homeobox 1". The mRNA accession number is NM_000209. The PDX1 reference sequence mRNA (NM_000209) has 2 exons and it transcribed from the positive strand.

To identify potential antisense transcripts from the PDX1 locus, the genomic region surrounding PDX1 was searched for spliced expressed sequence tags (ESTs) that mapped to the appropriate strand (the negative strand).

Although it is normally difficult to determine the transcriptional orientation of ESTs, orientation can be determined by using splice site signatures of spliced ESTs. EST CR593175 was chosen as a target candidate.

As recent deep sequencing experiments have revealed that antisense RNAs often are found in the region surrounding TSSs, it was decided to design short activating RNAs that targeted potential antisense transcripts from PDX1's promoter region. More specifically, the antisense sequence 500 nts upstream and downstream from PDX1's TSS (abbreviated PDX1_AS_TSS+/−500) was used as a second target candidate.

The aim was to design short RNAs for down-regulating the two candidate sequences. Candidate short RNAs should give effective inhibition of target sequences, and should ideally be as specific as possible such that potential off-target effects are minimized Therefore the GPboost siRNA design algorithm was used to identify potential short RNAs for down-regulating the two candidate sequences. From the lists of predicted siRNA candidates, the two most promising non-overlapping siRNA target sites in exons 1 and 2 of the EST CR593175, and the most promising siRNA target site on each side of the PDX1 TSS within the promoter sequence (PDX1_AS_TSS+/−500) were selected. The candidate siR-NAs were selected based on predicted efficacy score from GPboost; absence of the sequence motifs aaaa, cccc, gggg, and uuuu; moderate GC content of between 20% and 55%; and a Hamming distance of at least two to all potential off-target transcripts. Table 1 shows the resulting candidate short RNAs for activating PDX1 expression. The table shows the sequence of single strands, but the activating RNAs may also be administered as double stranded molecules.

Example 2

Designing Short RNAs for Activating Expression of Neurogenin 3

Design was carried out as in Example 1, with the following differences.

Neurogenin is located on chromosome 10 (see FIG. 2), band q21.3. The full name of the Neurogenin 3 gene is "*Homo sapiens* neurogenin3". The mRNA accession number is NM_020999. The Neurogenin 3 reference sequence mRNA (NM_020999) has 2 exons and is transcribed from the negative strand.

EST AI744512 was chosen as a target candidate. NEUROG3_AS_TSS+/−500) was used as a second target candidate.

Table 2 shows the resulting candidate short RNAs for activating Neurogenin3 expression. The table shows the sequence of single strands, but the activating RNAs may also be administered as double stranded molecules.

Example 3

Designing Short RNAs for Activating Expression of Rfx6

Design was carried out as in Example 1, with the following differences.

Rfx6 is located on chromosome 6 (see FIG. 3), band q22.2. The full name of the Rfx6 gene is "*Homo sapiens* regulatory factor X, 6". The mRNA accession number is NM_173560. The Rfx6 reference sequence mRNA (NM_173560) has 19 exons and is transcribed from the positive strand.

EST NM_148963 was chosen as a target candidate. RFX6_AS_TSS+/−500) was used as a second target candidate.

Table 3 shows the resulting candidate short RNAs for activating Rfx6 expression. The table shows the sequence of single strands, but the activating RNAs may also be administered as double stranded molecules.

Example 4

Designing Short RNAs for Activating Expression of MafA

Design was carried out as in Example 1, with the following differences.

MafA is located on chromosome 8 (see FIG. 4) q24.3. The full name of the MAFA gene is "*Homo sapiens* v-maf musculoaponeurotic fibrosarcoma oncogene homolog A (avian)". The mRNA accession number is NM_201589. The MafA reference sequence mRNA (NM_201589) has 1 exon and is transcribed from the negative strand.

MAFA_AS_TSS+/−500) was used as a target candidate.

Table 4 shows the resulting candidate short RNAs for activating MafA expression. The table shows the sequence of single strands, but the activating RNAs may also be administered as double stranded molecules.

Example 5

Induction of Specialisation—Generation of Insulin Producing Cells

Materials and Methods

Pluripotent cells (omnicytes) were obtained as follows: Granulocyte colony stimulating factor (G-CSF) mobilized peripheral blood cells were obtained from leukaphereses processed by the Stem Cell Laboratory, Hammersmith Hospital, in excess of clinical requirements. Informed consent and local research ethics committee approval were granted in all cases. CD34$^+$ cells were diluted at 1:4 in Hanks' buffer saline solution (HBSS; Gibco, Paisley, U.K) before the monoculear cells (MNCs) were separated by centrifugation over a Lymphoprep (Axis-Shield, Kimbolton, Cambridgeshire, UK) density gradient at 1,800 rpm for 30 minutes (Heraeus, Hanau, Germany). The MNC fraction was collected and washed first in HBSS, then with MACS (magnetic cell sorting) buffer (phosphate-buffered saline) supplemented with 0.5% human serum albumin and 5 mM EDTA, pH 7.2). CD34$^+$ cells were isolated from MNCs using the CD34$^+$ positive cell selection kit (LargeMacs; Miltenyi Biotec, Bergisch Gladbach, Germany). Isolated CD34$^+$ cells were plated on 24 well culture dishes (Corning, USA) at a density of $2.5 \times 10^5$ cells per well with 500 µl of α-minimal essential medium (α-MEM) and incubated for 30 minutes at 37° C. and 5% $CO_2$. After this incubation, the non adherent cell population was removed by washing the plates four times with PBS.

Induction of specialisation was carried out as set out in FIG. 7. Omnicytes (CD34+, adherent) were cultured in serum-free expansion media (Omnicyte Limited) supplemented with 2.5 mM (or 2.5 nM) glucose and 10 ng activin A for three days.

At days 3 and 6, the cells were transfected with saRNA molecules. Paired saRNA oligonucleotides were annealed using 50 mM Tris-HCl, pH8.0, 100 mM NaCl and 5 mM EDTA. A denaturation step at 90° C. was followed by a gradual anneal step to room temperature. Transfection of the annealed saRNA oligonucleotides (0.15 µg/well) was performed using Nanofectamin (PAA) following manufacturer's protocol.

At day 3 and day 6 of 11 mM (or 11 nM) glucose, 5 ng exenedin, 50 ng human noggin, 5 ng FGF, 5 ng EGF were added.

RNA Analysis

For RNA analysis, cells were harvested at day 9 and pelleted by centrifugation. Total RNA was recovered using the RNAqueous-Micro kit (Ambion) following the manufacturer's instructions. The RNA was quantified using a Nanodrop 1000 micro-sample quantitator. 1 µg of total RNA from each sample was reverse transcribed using the One Step RT-PCR kit from Qiagen following the manufacturer's recommendation. Expression of PDX1, Rfx6, MafA and Insulin was measured semi-quantitatively by PCR. Actin was used as a loading control.

Immunofluorescence

Cells were fixed for 20 minutes with 4% paraformaldehyde on to 1 cm glass cover slips followed by permeabilisation with 0.2% TritonX100 for 20 minutes. The coverslips were washed three times followed by blocking with 10% rabbit serum for 45 minutes. Rabbit raised anti-human insulin (1:200) (Sigma) was added to the cells in 10% serum for one hour. Cells were washed three times in PBS followed by the addition of 10% serum for a further 15 minutes prior to incubation with Alexa-488 conjugated anti-rabbit secondary antibody (1:600)(Cell Signalling Technology) for one hour. After five washes in PBS, coverslips were mounted onto glass slides with Vectashield containing 4'6'-diamidino-2-phenylindole (DAPI) (Vector labs). Slides were visualised on a Leica DM4000 at 60× magnification. An average of 5 images was captured and compared to staining with the secondary conjugated antibody alone to confirm no presence of autofluorescence.

Pro-Insulin ELISA

At day 9, cells were transferred to a pre-conditioning α-MEM media supplemented with 10 mM nicotinamide, 50 ng IGF-II, 10 ng HGF, 25 ng exenedin-4 and 10 ng activin A (Appendix E). Cells were incubated for 16 hours at 37° C. and 5% $CO_2$ before addition of a glucose gradient. 2.8 mM (or 2.8 nM) of glucose was added for 3 hours followed by 20 mM (or 20 nM) of glucose for a further 3 hours. The media was isolated and processed for total human proinsulin ELISA (Millipore) following the manufacturer's instructions. The positive control as supplied by the kit contains 7.9 pM of insulin.

Results

Omnicytes Express the Necessary Factors for Pancreatic β Cell Specialisation

The primitive nature of plastic adherent bone marrow derived stem cells were already established by Gordon M Y et al., (1987) and Gordon M Y (1994) (8, 9). We confirmed the presence of transcription factors necessary for specialisation into pancreatic β cell including NeuroD, PDX1 and Rfx6 from freshly isolated omnicytes. Expression of these factors was naturally downregulated within three days of culture (FIG. 5A).

Transfection of Annealed saRNA Oligonucleotides Upregulates Target Genes

To maintain or increase expression of the necessary transcription factors for specialisation into insulin-producing cells, small activating RNA (saRNA) oligonucleotides were generated using bioinformatics and software algorithm as mentioned in materials and methods (i.e. the main body of the description). These oligonucleotides were annealed and transfected at days 3 and 6 before cell harvesting at day 9. mRNA analysis demonstrated that upregulation of PDX1 (FIG. 1) was sufficient to drive the sequential activation of the downstream transcription factor Rfx6.1 that is necessary for islet formation and insulin expression (21) (FIG. 5B). The morphology of the cells transfected with PDX1 at day 9 was characteristic of islet cell clusters formation where immunofluorescent staining demonstrated expression of insulin (FIG. 5C). These cells however did not secrete insulin following exposure to a glucose gradient, suggesting immature islet cells.

Upregulation of Transcription Factors Necessary for Mature β Cell Specialisation To complement the full set of genes necessary for mature β cell specialisation, saRNA targeting neurogenin 3 (FIG. 2), Rfx6 (FIG. 3) and MafA (FIG. 4) were transfected into the cells. mRNA analysis demonstrated that expression of pre pro-insulin and pro-insulin were significantly upregulated by day 9 of cell culture (FIG. 6 A).

Combination of saRNA Targeting PDX1 and Late Transcription Factors for β Cell Specialisation Since targeted upregulation of PDX1, Rfx6 Neurogenin 3 (Ngn3) and MafA were confirmed by mRNA analysis following transfection of saRNA oligonucleotides, we attempted to add a combination of these oligonucleotides to omnicytes to assess if the cells would show signs of developing into more mature insulin secreting β cells. Following a combination of Rfx6, Ngn3 and MafA alone or PDX1+ Rfx6; PDX1+Ngn3 or PDX1+MafA transfected at days 3 and 6, cells were primed for a glucose response test at day 9 as described in materials and methods followed by an ELISA for total pro-insulin secretion. The values shown are percentages relative to a positive control of 7.9 pM insulin as provided by the ELISA kit (Millipore) and represent cells cultured in a single well of a 24-well plate (FIG. 6B).

Discussion

The progress made over the last decade in the understanding and manipulation of stem cells has enabled researchers to use these cells for regenerative therapy. Since embryonic cells carry a risk of tumourigenicity, the ethical constraints against their use for clinical applications has meant more focus on using adult progenitor cells. Research in this area has previously been limited by the reliance on genetically modified components which were not translatable for clinical use. Omnicytes however meets all of the necessary safety criteria for use as replacement stem cells in therapy (22). They can be isolated autologously; they have a robust expansion potential in a serum free environment and display remarkable developmental plasticity since they already express the necessary transcription factors for commitment to different lineages including liver, pancreas, cardiovascular and nerve cells (22). The data shown herein demonstrates that omnicytes can be induced into insulin secreting cells by use of novel small activating RNA molecules. These molecules undoubtedly allow a safer approach when compared to using standard techniques that rely on vectors with a viral based backbone. We have shown that the activation of only a few target transcription factors is sufficient to cause a cascade effect which regulates downstream genes necessary for induction of insulin production.

Example 6

Designing Short RNAs for Activating Expression of (Pro) Insulin

Design was carried out as in Example 1, with the following differences.

(pro)insulin is located on chromosome 11 (see FIG. 8), band p15.5. The full name of the insulin gene is "*Homo sapiens* insulin" The mRNA accession number is NM_000207. The (pro)insulin reference sequence mRNA (NM_000207) has 3 exons and is transcribed from the negative strand.

INS (NM001185098)_AS_TSS+/−500 was used as a target candidate.

Tables 5 and 6 shows the resulting candidate short RNAs for activating (pro)insulin expression.

Example 7

Induction of Insulin Production Using saRNA to Up-Regulate MafA a) Optimised Protocol for the Induction of CD34+ Cells into an Insulin Secreting Phenotype Commencement of the induction protocol involved supplementing the adherent population of CD34+ cells (Omnicytes) with 10 ng/ml of Activin A (Sigma, UK) and 2.5 nM Glucose (Sigma, USA) into serum-free CellGro media (CellGenix, UK) containing Stem Cell Factor (Inivitrogen, USA), 250 ng/ml of Interleukin-3 and Interleukin-6 (Invitrogen, USA) for 72 hours at Day 0. Cells were allowed to expand to 80% confluency before the addition of 11 nM Glucose, 5 ng Exendin-4 (Sigma, USA), 50 ng Noggin (Sigma, USA), 5 ng bFGF (Sigma, USA) and 5 ng EGF (Sigma, USA) at 72 hour intervals together with transfection of 150 ng of double stranded saRNA designed to upregulate MafA using Nanofectamine (PAA, UK) with α-MEM media (without antibiotics) following the manufacturer's instructions. This process was repeated three times at Days 2/3, 5/6 and 8/9 (dependent on establishing the appropriate cell density)—To achieve maximum transfection efficiency, cells were prevented from clustering by gentle pippetting every 24 hours.

A workflow of the optimised protocol is shown in FIG. 14. Two specific saRNAs which can up-regulate MafA were used in combination. The double-stranded form of each saRNA was used. They are designated MafA Pr-1 and MafA Pr-2 (see Table 4, which shows that they have SEQ ID NOs 5 and 6 respectively).

Cells treated with these saRNAs are referred to in this Example as "transfected" cells.

b) Western Blot of Actin and Insulin.

10 μg of total protein extract from undifferentiated CD34+ cells (control) and transfected CD34+ cells (prepared according to the protocol above) were separated on SDS-PAGE (4-12% TrisGlycine denaturing acrylamide gel from Invitrogen). After transfer onto nitrocellulose membrane, the blots were incubated with anti-actin (Sigma)(1:8000) and anti-insulin (Abcam) followed by HRP conjugated secondary antibody (1:10000) (Dako). Insulin is a small peptide with a molecular weight of about 6 kDa (kilo Daltons) comprising of a small α subunit and a larger β subunit. Results are shown in FIG. 10.

c) Quantitative PCR (qPCR) of Key Transcription Factors Involved in β-Cell Development.

The relative quantity (RQ) of transcripts from differentiated (untransfected) CD34+ cells (controls) compared with transfected CD34+ cells (prepared according to the protocol above) and total human adult normal pancreatic RNA was assessed. Results are shown in FIG. 11. Primers for the target genes are validated Quantitect Primers from Qiagen.

d) Electron microscopy analysis was carried out of CD34+ cells that are either (A) Undifferentiated or (B) transfected. Transfected Cells (B) were prepared according to the protocol above. Results are shown in FIG. 12. Compared to (A), granular vesicles are apparent in (B) where the cells have started differentiating towards PDX1 and insulin expression (see qPCR data). Signs of granules clustering together can be seen (arrows). Pronounced and clustered vesicles are seen to be polarising to towards the cell membrane in the transfected cells.

e) Enzyme linked immunoabsorbant assay (ELISA) of Insulin and C-peptide. The culture media from undifferentiated CD34+ cells and from transfected cells were recovered after exposure of cells to low glucose (2.8 nM) followed by high glucose (16 nM) pulse. The media was then transferred onto the immunoabsorbant ELISA plates specific for human insulin and human C-peptide (Millipore) following the manufacturers protocol. The data, shown in FIG. 13, shows that transfected cells are able to respond to a glucose gradient by secreting insulin.

Example 8

MafA upregulation using short RNAs of the invention was also achieved in liver cells. Liver epithelial cells were transfected with saRNAs denoted Pr-1 and PR-2 (see Table 4, and Table 7 shows that Pr-1 is SEQ ID NO: 5 paired with SEQ ID NO:49 and Pr-2 is SEQ ID NO: 6 paired with SEQ ID NO: 50). The results show that each saRNA alone was able to up-regulate MafA expression, and that the combination of both sRNAs achieved greater upregulation than each saRNA alone. See FIG. 15.

Example 9

Further saRNAs were designed according to the principles set out herein, and their sequences are shown in Table 7.

Tables

In the Tables, Loc stands for location and E stands for Exon

TABLE 1

| ID | Target (CR593175) | SEQ ID NO | Loc | E | Antisense (guide) | SEQ ID NO |
|---|---|---|---|---|---|---|
| CR-1 | TCTAGAACTC AGAAATTTA (UCUAGAACUC AGAAAUUUA) | 59 | 433 | 2 | UAAAUUUCUG AGUUCUAGA | 15 |
| CR-2 | CGAATTCGCT TCTCAGATT (CGAAUUCGCU UCUCAGAUU) | 60 | 174 | 1 | AAUCUGAGAA GCGAAUUCG | 16 |

| ID | Target (PDX1 AS TSS+/-500) | | Loc | | | |
|---|---|---|---|---|---|---|
| Pr-1 | GCGCATGGGT CCTTGTAAA (GCGCAUGGGU CCUUGUAAA) | 61 | 324 | | UUUACAAGGA CCCAUGCGC | 17 |
| Pr-2 | GAACCACTCA TTTATAGAA (GAACCACUCA UUUAUAGAA) | 62 | 758 | | UUCUAUAAAU GAGUGGUUC | 18 |

TABLE 2

| ID | Target (AI744512) | SEQ ID NO | Loc | E | Antisense (guide) | SEQ ID NO |
|---|---|---|---|---|---|---|
| A1-1 | CCAGTGTTTG CTAAAATAA (CCAGUGUUUG CUAAAAUAA) | 55 | 450 | 2 | UUAUUUUAGC AAACACUGG | 11 |
| A1-2 | CAGCCTTGCC TGATTTATT (CAGCCUUGCC UGAUUUAUU) | 56 | 111 | 1 | AAUAAAUCAG GCAAGGCUG | 12 |

| ID | Target (NEUROG3 AS TSS+/-500) | | Loc | | | |
|---|---|---|---|---|---|---|
| Pr-1 | GGAGGTGGCT TGTCTGAAA (GGAGGUGGCU UGUCUGAAA) | 57 | 966 | | UUUCAGACAA GCCACCUCC | 13 |
| Pr-2 | GGCTTCTGGT CGCCAAGTT (GGCUUCUGGU CGCCAAGUU) | 58 | 405 | | AACUUGGCGA CCAGAAGCC | 14 |

TABLE 3

| ID | Target (NM_148963) | SEQ ID NO | Loc | E | Antisense (guide) | SEQ ID NO |
|---|---|---|---|---|---|---|
| NM-1 | GUGGAUUGCUAGUGAUAAU | 63 | 3 | | AUUAUCACUAGCAAUCCAC | 19 |
| NM-2 | ACACUAAUCAGACAGAUAU | 64 | 5/6 | | AUAUCUGUCUGAUUAGUGU | 20 |

| ID | Target (RFX6 AS TSS+/-500) | | | | | |
|---|---|---|---|---|---|---|
| Pr-1 | ACUGUUUCUUCCGGAUAGA | 65 | 305 | | UCUAUCCGGAAGAAACAGU | 21 |
| Pr-2 | ACUGUCUUCUGCAGGGAAA | 66 | 829 | | UUUCCCUGCAGAAGACAGU | 22 |

TABLE 4

| ID | Target (MAFA AS TSS+/-500) | SEQ ID NO | Loc | Antisense (guide) | SEQ ID NO |
|---|---|---|---|---|---|
| Pr-1 | CCGCTCATCCAGTACAGAT (CCGCUCAUCAGUACAGAU) | 49 | 138 | AUCUGUACUGGAUGAGCGG | 5 |
| Pr-2 | GTCAATCTCCTGCGGGAAA (GUCAAUCUCCUGCGGGAAA) | 50 | 968 | UUUCCCGCAGGAGAUUGAC | 6 |

TABLE 5

| ID | Target (INS NM_001185098) AS TSS+30/-500 | SEQ ID NO | Loc | Antisense (guide) | SEQ ID NO |
|---|---|---|---|---|---|
| INS-Pr-1 | gacagtgatctgggagaca (gacagugaucugggagaca) | 45 | 270 | UGUCUCCCAGAUCACUGUC | 1 |
| INS-Pr-2 | acaggtgttggttcacaaa (acaggguguugguucacaaa) | 46 | 171 | UUUGUGAACCAACACCUGU | 2 |
| INS-Pr-3 | ggcaaatgtctccaggaga (ggcaaaugucuccaggaga) | 47 | 765 | UCUCCUGGAGACAUUUGCC | 3 |
| INS-Pr-4 | ctgcaatttccggaccatt (cugcaauuuccggaccauu) | 48 | 623 | AAUGGUCCGGAAAUUGCAG | 4 |

TABLE 6

| ID | Sense (passenger) | Antisense (guide) | SEQ ID NO |
|---|---|---|---|
| INS-45 plus Pr-1 UU tail | GACAGUGAUCUGGGAGACAUU | UGUCUCCCAGAUCACUGUCUU | 1 plus UU tail |
| INS-46 plus Pr-2 UU tail | ACAGGUGUUGGUUCACAAAUU | UUUGUGAACCAACACCUGUUU | 2 plus UU tail |
| INS-47 plus Pr-3 UU tail | GGCAAAUGUCUCCAGGAGAUU | UCUCCUGGAGACAUUUGCCUU | 3 plus UU tail |
| INS-48 plus Pr-4 UU tail | CUGCAAUUUCCGGACCAUUUU | AAUGGUCCGGAAAUUGCAGUU | 4 plus UU tail |

TABLE 7

| | SEQ ID NO | sense | anti-sense | SEQ ID NO |
|---|---|---|---|---|
| Insulin | | | | |
| INS-Pr-1 | 45 | GACAGUGAUCUGGGAGACA | UGUCUCCCAGAUCACUGUC | 1 |
| INS-Pr-2 | 46 | ACAGGUGUUGGUUCACAAA | UUUGUGAACCAACACCUGU | 2 |
| INS-Pr-3 | 47 | GGCAAAUGUCUCCAGGAGA | UCUCCUGGAGACAUUUGCC | 3 |
| INS-Pr-4 | 48 | CUGCAAUUUCCGGACCAUU | AAUGGUCCGGAAAUUGCAG | 4 |
| MafA | | | | |
| Pr-1 | 49 | CCGCUCAUCCAGUACAGAU | AUCUGUACUGGAUGAGCGG | 5 |
| Pr-2 | 50 | GUCAAUCUCCUGCGGGAAA | UUUCCCGCAGGAGAUUGAC | 6 |
| NeuroD1 | | | | |
| BQ-1 | 51 | GGCGAAUUGUGGAAGGAAU | AUUCCUUCCACAAUUCGCC | 7 |
| BQ-2 | 52 | GAAUGACUUCCUCAACCUA | UAGGUUGAGGAAGUCAUUC | 8 |

TABLE 7-continued

| | SEQ ID NO | sense | anti-sense | SEQ ID NO |
|---|---|---|---|---|
| Pr-1 | 53 | GAGCAGUGAUAGUCUCAUA | UAUGAGACUAUCACUGCUC | 9 |
| Pr-2 | 54 | CCUUUGUGGCCAGAAGAAA | UUUCUUCUGGCCACAAAGG | 10 |
| Neurogenin3 | | | | |
| AI-1 | 55 | CCAGUGUUUGCUAAAAUAA | UUAUUUUAGCAAACACUGG | 11 |
| AI-2 | 56 | CAGCCUUGCCUGAUUUAUU | AAUAAAUCAGGCAAGGCUG | 12 |
| Pr-1 | 57 | GGAGGUGGCUUGUCUGAAA | UUUCAGACAAGCCACCUCC | 13 |
| Pr-2 | 58 | GGCUUCUGGUCGCCAAGUU | AACUUGGCGACCAGAAGCC | 14 |
| PDX1 | | | | |
| CR-1 | 59 | UCUAGAACUCAGAAAUUUA | UAAAUUUCUGAGUUCUAGA | 15 |
| CR-2 | 60 | CGAAUUCGCUUCUCAGAUU | AAUCUGAGAAGCGAAUUCG | 16 |
| Pr-1 | 61 | GCGCAUGGGUCCUUGUAAA | UUUACAAGGACCCAUGCGC | 17 |
| Pr-2 | 62 | GAACCACUCAUUUAUAGAA | UUCUAUAAAUGAGUGGUUC | 18 |
| Rfx6 | | | | |
| NM-1 | 63 | GUGGAUUGCUAGUGAUAAU | AUUAUCACUAGCAAUCCAC | 19 |
| NM-2 | 64 | ACACUAAUCAGACAGAUAU | AUAUCUGUCUGAUUAGUGU | 20 |
| Pr-1 | 65 | ACUGUUUCUUCCGGAUAGA | UCUAUCCGGAAGAAACAGU | 21 |
| Pr-2 | 66 | ACUGUCUUCUGCAGGGAAA | UUUCCCUGCAGAAGACAGU | 22 |
| Glut2 | | | | |
| Pr-1 | 67 | GUUGGGAGUCCUGUCAAUU | AAUUGACAGGACUCCCAAC | 23 |
| Pr-2 | 68 | GCUUCAUAUAUGUCAAGAA | UUCUUGACAUAUAUGAAGC | 24 |
| GLP-1Receptor | | | | |
| Pr-1 | 69 | CUCGGAGUUUCGUUCAAGU | ACUUGAACGAAACUCCGAG | 25 |
| Pr-2 | 70 | GGCCACUCCUGGAAAGUAU | AUACUUUCCAGGAGUGGCC | 26 |
| Betacellulin | | | | |
| Pr-1 | 71 | UUGCUAGUGUCAUGGAGAA | UUCUCCAUGACACUAGCAA | 27 |
| Pr-2 | 72 | CCAAACGUGUUCUGGAAUU | AAUUCCAGAACACGUUUGG | 28 |
| NFkB, variant1 | | | | |
| Pr-1 | 73 | CCAAGCAUGCCAGAUAUAA | UUAUAUCUGGCAUGCUUGG | 29 |
| Pr-2 | 74 | AUAAAGCUCAUCUGUAUAU | AUAUACAGAUGAGCUUUAU | 30 |
| Fox A2 | | | | |
| Pr-1 | 75 | CUGAGAUUUGUCUCUGAUA | UAUCAGAGACAAAUCUCAG | 31 |
| Pr-2 | 76 | GAAGAAUCCAGGAAUCAAU | AUUGAUUCCUGGAUUCUUC | 32 |
| Bcl2 | | | | |
| Pr-1 | 77 | GAGGAUUUCCAGAUCGAUU | AAUCGAUCUGGAAAUCCUC | 33 |
| Pr-2 | 78 | UCAGCACUCUCCAGUUAUA | UAUAACUGGAGAGUGCUGA | 34 |
| Pr-3 | 79 | GCAGGAAUCCUCUUCUGAU | AUCAGAAGAGGAUUCCUGC | 35 |
| Pr-4 | 80 | GCAGAAGUCCUGUGAUGUU | AACAUCACAGGACUUCUGC | 36 |

TABLE 7-continued

| | SEQ ID NO | sense | anti-sense | SEQ ID NO |
|---|---|---|---|---|
| v-myc | | | | |
| BC-1 | 81 | GUGACUAUUCAACCGCAUA | UAUGCGGUUGAAUAGUCAC | 37 |
| BC-2 | 82 | GAGGAGUUACUGGAGGAAA | UUUCCUCCAGUAACUCCUC | 38 |
| Pr-1 | 83 | AGCAGUACUGUUUGACAAA | UUUGUCAAACAGUACUGCU | 39 |
| Pr-2 | 84 | GAAUUACUACAGCGAGUUA | UAACUCGCUGUAGUAAUUC | 40 |
| Telomerase rt | | | | |
| BF-1 | 85 | GUGAAAUUUCCACAACACA | UGUGUUGUGGAAAUUUCAC | 41 |
| BF-2 | 86 | CAGAGUACUUAUCAUGAAU | AUUCAUGAUAAGUACUCUG | 42 |
| Pr-1 | 87 | GGCGUCUGUGCCCGCGAAU | AUUCGCGGGCACAGACGCC | 43 |
| Pr-2 | 88 | GACGCAGCGCUGCCUGAAA | UUUCAGGCAGCGCUGCGUC | 44 |

---

The invention claimed is:

1. A method of inducing insulin production in a cell by up-regulating a target gene involved in insulin production in said cell, wherein the target gene is selected from the group consisting of insulin, PDX1, Neurogenin 3 (Ngn3), Rfx6, MafA, GLP1 receptor, FOXA2, HNF1A, Hlxb9, Hnf6, Ptf1a, Neuro D, betacellulin, ABCC8, glucokinase (GCK), GLUT2, and Nkx6-1, comprising
- (i) designing an saRNA (short activating ribonucleic acid) which specifically targets a target antisense RNA transcript present in said cell, wherein said target RNA transcript is complementary to a sequence located on the coding strand of the target gene between 500 nucleotides upstream and 500 nucleotides downstream of the transcription start site of the target gene; and said saRNA is a single or double stranded RNA molecule up to 30 nucleotides in length comprising a sequence of at least 13 nucleotides which has at least 95% complementarity to a region of the target transcript;
- (ii) synthesizing said saRNA;
- (iii) administering said saRNA to said cell; and
- (iv) performing analysis to confirm said saRNA up-regulates said target gene.

2. A method according to claim 1, wherein the cell is induced to produce insulin in a glucose-responsive manner.

3. A method according to claim 1, wherein the cell is induced to secrete insulin.

4. A method according to claim 1, wherein said target RNA transcript overlaps the transcription start site and/or a promoter region of the target gene.

5. A method according to claim 1, wherein said saRNA is a double-stranded RNA of 19 to 25 base pairs in length with 1-5 unpaired bases on each 3' end forming a 3' overhang.

6. A method according to claim 1, wherein said saRNA can down-regulate said target RNA transcript by RNA-induced silencing complex (RISC)-associated cleavage.

7. A method according to claim 1, wherein said saRNA possesses none of the motifs aaaa, cccc, gggg, and uuuu and/or has a GC-percentage of at least 20% and no more than 75%.

8. A method according to claim 1, wherein the cell which is induced to produce insulin is an adult or embryonic stem cell, a pluripotent cell, a multipotent cell or a somatic cell.

9. A method according to claim 1, wherein the cell which is induced to produce insulin is a liver cell or a pancreatic cell.

10. A method of treating a condition associated with aberrant insulin production, uptake or utilisation, said method comprising administering to a subject in need thereof a pharmaceutically effective amount of an saRNA, wherein said saRNA is capable of inducing insulin production in a cell by up-regulating a target gene involved in insulin production in said cell by specifically targeting a target RNA transcript present in said cell, wherein the target gene is selected from the group consisting of insulin, PDX1, Neurogenin 3 (Ngn3), Rfx6, MafA, GLP1 receptor, FOXA2, HNF1A, Hlxb9, Hnf6, Ptf1a, Neuro D, betacellulin, ABCC8, glucokinase (GCK), GLUT2, and Nkx6-1, and wherein

- (i) said target RNA transcript is complementary to a sequence located on the coding strand of the target gene between 500 nucleotides upstream and 500 nucleotides downstream of the transcription start site of the target gene;
- (ii) said sRNA is a single or double stranded RNA molecule up to 30 nucleotides in length comprising a sequence of at least 13 nucleotides which has at least 95% complementarity to a region of the target transcript; and
- (iii) an analysis has been performed to confirm that said saRNA up-regulates said target gene.

11. The method of claim 7, wherein the GC-percentage of said saRNA is between 20% and 55%.

12. The method of claim 1, wherein the analysis is mRNA analysis.

* * * * *

SEQUENCE LISTING

<160> NUMBER OF SEQ ID NOS: 96

<210> SEQ ID NO 1
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 1
ugucucccag aucacuguc                                                19

<210> SEQ ID NO 2
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 2
uuugugaacc aacaccugu                                                19

<210> SEQ ID NO 3
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 3
ucuccuggag acauuugcc                                                19

<210> SEQ ID NO 4
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 4
aaugguccgg aaauugcag                                                19

-continued

<210> SEQ ID NO 5
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 5
aucuguacug gaugagcgg                                                    19

<210> SEQ ID NO 6
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 6
uuucccgcag gagauugac                                                    19

<210> SEQ ID NO 7
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 7
auuccuucca caauucgcc                                                    19

<210> SEQ ID NO 8
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 8
uagguugagg aagucauuc                                                    19

<210> SEQ ID NO 9
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 9
uaugagacua ucacugcuc                                                    19

<210> SEQ ID NO 10
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 10
uuucuucugg ccacaaagg                                                    19

<210> SEQ ID NO 11
<211> LENGTH: 19
<212> TYPE: RNA
<213> ORGANISM: Artificial Sequence
<220> FEATURE:

<223> OTHER INFORMATION: Chemically-synthesized antisense sequence

<400> SEQUENCE: 11
uuauuuuagc aaacacugg                                                    19

<210> SEQ ID NO 12
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 12
aauaaaucag gcaaggcug                                                    19

<210> SEQ ID NO 13
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 13
uuucagacaa gccaccucc                                                    19

<210> SEQ ID NO 14
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 14
aacuuggcga ccagaagcc                                                    19

<210> SEQ ID NO 15
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 15
uaaauuucug aguucuaga                                                    19

<210> SEQ ID NO 16
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 16
aaucugagaa gcgaauucg                                                    19

<210> SEQ ID NO 17
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 17
uuuacaagga cccaugcgc                                                    19

```
<210> SEQ ID NO 18
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 18
uucuauaaau gagugguuc                                                    19

<210> SEQ ID NO 19
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 19
auuaucacua gcaauccac                                                    19

<210> SEQ ID NO 20
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 20
auaucugucu gauuagugu                                                    19

<210> SEQ ID NO 21
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 21
ucuauccgga agaaacagu                                                    19

<210> SEQ ID NO 22
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 22
uuucccugca gaagacagu                                                    19

<210> SEQ ID NO 23
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 23
aauugacagg acucccaac                                                    19

<210> SEQ ID NO 24
<211> LENGTH: 19
<212> TYPE: RNA
<213> ORGANISM: Artificial Sequence
<220> FEATURE:
<223> OTHER INFORMATION: Chemically-synthesized antisense sequence
```

```
<400> SEQUENCE: 24
uucuugacau auaugaagc                                              19

<210> SEQ ID NO 25
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 25
acuugaacga aacuccgag                                              19

<210> SEQ ID NO 26
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 26
auacuuucca ggaguggcc                                              19

<210> SEQ ID NO 27
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 27
uucuccauga cacuagcaa                                              19

<210> SEQ ID NO 28
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 28
aauuccagaa cacguuugg                                              19

<210> SEQ ID NO 29
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 29
uuauaucugg caugcuugg                                              19

<210> SEQ ID NO 30
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 30
auauacagau gagcuuuau                                              19

<210> SEQ ID NO 31
<211> LENGTH: 19
```

```
<212> TYPE: RNA
<213> ORGANISM: Artificial Sequence
<220> FEATURE:
<223> OTHER INFORMATION: Chemically-synthesized antisense sequence

<400> SEQUENCE: 31
uaucagagac aaaucucag                                                       19

<210> SEQ ID NO 32
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 32
auugauuccu ggauucuuc                                                       19

<210> SEQ ID NO 33
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 33
aaucgaucug gaaauccuc                                                       19

<210> SEQ ID NO 34
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 34
uauaacugga gagugcuga                                                       19

<210> SEQ ID NO 35
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 35
aucagaagag gauuccugc                                                       19

<210> SEQ ID NO 36
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 36
aacaucacag gacuucugc                                                       19

<210> SEQ ID NO 37
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 37
```

-continued

```
uaugcgguug aauagucac                                            19

<210> SEQ ID NO 38
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 38
uuuccuccag uaacuccuc                                            19

<210> SEQ ID NO 39
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 39
uuugucaaac aguacugcu                                            19

<210> SEQ ID NO 40
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 40
uaacucgcug uaguaauuc                                            19

<210> SEQ ID NO 41
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 41
uguguugugg aaauuucac                                            19

<210> SEQ ID NO 42
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 42
auucaugaua aguacucug                                            19

<210> SEQ ID NO 43
<211> LENGTH: 19
<212> TYPE: RNA
<213> ORGANISM: Artificial Sequence
<220> FEATURE:
<223> OTHER INFORMATION: Chemically-synthesized antisense sequence

<400> SEQUENCE: 43
auucgcgggc acagacgcc                                            19

<210> SEQ ID NO 44
<211> LENGTH: 19
<212> TYPE: RNA
<213> ORGANISM: Artificial Sequence
```

```
<220> FEATURE:
<223> OTHER INFORMATION: Chemically-synthesized antisense sequence

<400> SEQUENCE: 44
uuucaggcag cgcugcguc                                                    19

<210> SEQ ID NO 45
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 45
gacagugauc ugggagaca                                                    19

<210> SEQ ID NO 46
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 46
acagguguug guucacaaa                                                    19

<210> SEQ ID NO 47
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 47
ggcaaauguc uccaggaga                                                    19

<210> SEQ ID NO 48
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 48
cugcaauuuc cggaccauu                                                    19

<210> SEQ ID NO 49
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 49
ccgcucaucc aguacagau                                                    19

<210> SEQ ID NO 50
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 50
gucaaucucc ugcgggaaa                                                    19
```

```
<210> SEQ ID NO 51
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 51
ggcgaauugu ggaaggaau                                              19

<210> SEQ ID NO 52
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 52
gaaugacuuc cucaaccua                                              19

<210> SEQ ID NO 53
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 53
gagcagugau agucucaua                                              19

<210> SEQ ID NO 54
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 54 ccuugugc cagaagaaa                                                19

<210> SEQ ID NO 55
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 55
ccaguguuug cuaaaauaa                                              19

<210> SEQ ID NO 56
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 56
cagccuugcc ugauuuauu                                              19

<210> SEQ ID NO 57
<211> LENGTH: 19
<212> TYPE: RNA
<213> ORGANISM: Artificial Sequence
<220> FEATURE:
<223> OTHER INFORMATION: Chemically-synthesized sense sequence
```

```
<400> SEQUENCE: 57
ggagguggcu ugucugaaa                                              19

<210> SEQ ID NO 58
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 58
ggcuucuggu cgccaaguu                                              19

<210> SEQ ID NO 59
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 59
ucuagaacuc agaaauuua                                              19

<210> SEQ ID NO 60
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 60
cgaauucgcu ucucagauu                                              19

<210> SEQ ID NO 61
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 61
gcgcaugggu ccuuguaaa                                              19

<210> SEQ ID NO 62
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 62
gaaccacuca uuuauagaa                                              19

<210> SEQ ID NO 63
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 63
guggauugcu agugauaau                                              19

<210> SEQ ID NO 64
```

```
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 64
acacuaauca gacagauau                                                    19

<210> SEQ ID NO 65
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 65
acuguuucuu ccggauaga                                                    19

<210> SEQ ID NO 66
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 66
acugucuucu gcagggaaa                                                    19

<210> SEQ ID NO 67
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 67
guugggaguc cugucaauu                                                    19

<210> SEQ ID NO 68
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 68
gcuucauaua ugucaagaa                                                    19

<210> SEQ ID NO 69
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 69
cucggaguuu cguucaagu                                                    19

<210> SEQ ID NO 70
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 70
```

```
ggccacuccu ggaaaguau                                          19

<210> SEQ ID NO 71
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 71
uugcuagugu cauggagaa                                          19

<210> SEQ ID NO 72
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 72
ccaaacgugu ucuggaauu                                          19

<210> SEQ ID NO 73
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 73
ccaagcaugc cagauauaa                                          19

<210> SEQ ID NO 74
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 74
auaaagcuca ucuguauau                                          19

<210> SEQ ID NO 75
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 75
cugagauuug ucucugaua                                          19

<210> SEQ ID NO 76
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 76
gaagaaucca ggaaucaau                                          19

<210> SEQ ID NO 77
<211> LENGTH: 19
<212> TYPE: RNA
```

```
<213> ORGANISM: Artificial Sequence
<220> FEATURE:
<223> OTHER INFORMATION: Chemically-synthesized sense sequence

<400> SEQUENCE: 77
gaggauuucc agaucgauu                                              19

<210> SEQ ID NO 78
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 78
ucagcacucu ccaguuaua                                              19

<210> SEQ ID NO 79
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 79
gcaggaaucc ucuucugau                                              19

<210> SEQ ID NO 80
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 80
gcagaagucc ugugauguu                                              19

<210> SEQ ID NO 81
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 81
gugacuauuc aaccgcaua                                              19

<210> SEQ ID NO 82
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 82
gaggaguuac uggaggaaa                                              19

<210> SEQ ID NO 83
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 83
agcaguacug uuugacaaa                                              19
```

```
<210> SEQ ID NO 84
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 84
gaauuacuac agcgaguua                                              19

<210> SEQ ID NO 85
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 85
gugaaauuuc cacaacaca                                              19

<210> SEQ ID NO 86
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 86
cagaguacuu aucaugaau                                              19

<210> SEQ ID NO 87
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 87
ggcgucugug cccgcgaau                                              19

<210> SEQ ID NO 88
<211> LENGTH: 19
<212> TYPE: RNA
<213> ORGANISM: Artificial Sequence
<220> FEATURE:
<223> OTHER INFORMATION: Chemically-synthesized sense sequence

<400> SEQUENCE: 88
gacgcagcgc ugccugaaa                                              19

<210> SEQ ID NO 89
<211> LENGTH: 21
<212> TYPE: RNA
<213> ORGANISM: Artificial Sequence
<220> FEATURE:
<223> OTHER INFORMATION: Antisense, equivalent to SEQ ID NO:1 with a UU
      tail

<400> SEQUENCE: 89
ugucucccag aucacugucu u                                           21

<210> SEQ ID NO 90
<211> LENGTH: 21
<212> TYPE: RNA
<213> ORGANISM: Artificial Sequence
```

```
<220> FEATURE:
<223> OTHER INFORMATION: Antisense, equivalent to SEQ ID NO:2 with a UU
      tail

<400> SEQUENCE: 90 uugugaacc aacaccuguu u                                              21

<210> SEQ ID NO 91
<211> LENGTH: 21
<212> TYPE: RNA
<213> ORGANISM: Artificial Sequence
<220> FEATURE:
<223> OTHER INFORMATION: Antisense, equivalent to SEQ ID NO:3 with a UU
      tail

<400> SEQUENCE: 91
ucuccuggag acauuugccu u                                             21

<210> SEQ ID NO 92
<211> LENGTH: 21
<212> TYPE: RNA
<213> ORGANISM: Artificial Sequence
<220> FEATURE:
<223> OTHER INFORMATION: Antisense, equivalent to SEQ ID NO:4 with a UU
      tail

<400> SEQUENCE: 92
aaugguccgg aaauugcagu u                                             21

<210> SEQ ID NO 93
<211> LENGTH: 21
<212> TYPE: RNA
<213> ORGANISM: Artificial Sequence
<220> FEATURE:
<223> OTHER INFORMATION: Sense, equivalent to SEQ ID NO:45 with a UU
      tail

<400> SEQUENCE: 93
gacagugauc ugggagacau u                                             21

<210> SEQ ID NO 94
<211> LENGTH: 21
<212> TYPE: RNA
<213> ORGANISM: Artificial Sequence
<220> FEATURE:
<223> OTHER INFORMATION: Sense, equivalent to SEQ ID NO:46 with a UU
      tail

<400> SEQUENCE: 94
acagguguug guucacaaau u                                             21

<210> SEQ ID NO 95
<211> LENGTH: 21
<212> TYPE: RNA
<213> ORGANISM: Artificial Sequence
<220> FEATURE:
<223> OTHER INFORMATION: Sense, equivalent to SEQ ID NO:47 with a UU
      tail

<400> SEQUENCE: 95
ggcaaauguc uccaggagau u                                             21

<210> SEQ ID NO 96
<211> LENGTH: 21
<212> TYPE: RNA
<213> ORGANISM: Artificial Sequence
<220> FEATURE:
```

-continued

```
<223> OTHER INFORMATION: Sense, equivalent to SEQ ID NO:48 with a UU
      tail

<400> SEQUENCE: 96
cugcaauuuc cggaccauuu u                                              21
```